(12) United States Patent
Greenberg et al.

(10) Patent No.: US 9,377,481 B1
(45) Date of Patent: *Jun. 28, 2016

(54) MULTI-PARAMETER SCATTERING SENSOR AND METHODS

(75) Inventors: Paul S Greenberg, Cleve. Hts., OH (US); David G Fischer, Richfield, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 60 days.

This patent is subject to a terminal disclaimer.

(21) Appl. No.: 13/134,959

(22) Filed: Jun. 16, 2011

Related U.S. Application Data

(60) Provisional application No. 61/355,376, filed on Jun. 16, 2010.

(51) Int. Cl.
*G01N 15/02* (2006.01)
*G01P 5/00* (2006.01)
*G01N 21/51* (2006.01)

(52) U.S. Cl.
CPC .......... *G01P 5/001* (2013.01); *G01N 2021/513* (2013.01)

(58) Field of Classification Search
CPC ...... G01P 5/001; B05B 12/082; G01N 21/49; G01N 15/0205; G01N 2021/513
USPC .................. 356/335, 336, 337, 339, 340, 625
See application file for complete search history.

(56) References Cited

U.S. PATENT DOCUMENTS

| | | | | |
|---|---|---|---|---|
| 3,624,835 A | * | 11/1971 | Wyatt | 356/343 |
| 4,490,042 A | * | 12/1984 | Wyatt | 356/340 |
| 4,541,719 A | * | 9/1985 | Wyatt | 356/343 |
| 5,681,752 A | * | 10/1997 | Prather | 436/173 |
| 6,774,994 B1 | * | 8/2004 | Wyatt et al. | 356/337 |
| 2004/0083064 A1 | * | 4/2004 | Wyatt | 702/28 |
| 2004/0144935 A1 | * | 7/2004 | Xu | 250/573 |
| 2006/0238757 A1 | * | 10/2006 | Silcott | 356/338 |
| 2007/0155017 A1 | * | 7/2007 | Wyatt | 436/45 |
| 2007/0299561 A1 | * | 12/2007 | Montaser et al. | 700/283 |
| 2009/0079981 A1 | * | 3/2009 | Holve | 356/336 |
| 2009/0222218 A1 | * | 9/2009 | Chamberlin et al. | 702/23 |

* cited by examiner

*Primary Examiner* — Tarifur Chowdhury
*Assistant Examiner* — Isiaka Akanbi
(74) *Attorney, Agent, or Firm* — Robert E. Earp, III

(57) ABSTRACT

Methods, detectors and systems detect particles and/or measure particle properties. According to one embodiment, a detector for detecting particles comprises: a sensor for receiving radiation scattered by an ensemble of particles; and a processor for determining a physical parameter for the detector, or an optimal detection angle or a bound for an optimal detection angle, for measuring at least one moment or integrated moment of the ensemble of particles, the physical parameter, or detection angle, or detection angle bound being determined based on one or more of properties (a) and/or (b) and/or (c) and/or (d) or ranges for one or more of properties (a) and/or (b) and/or (c) and/or (d), wherein (a)-(d) are the following: (a) is a wavelength of light incident on the particles, (b) is a count median diameter or other characteristic size parameter of the particle size distribution, (c) is a standard deviation or other characteristic width parameter of the particle size distribution, and (d) is a refractive index of particles.

17 Claims, 34 Drawing Sheets

FIG. 2B

Figure 1:
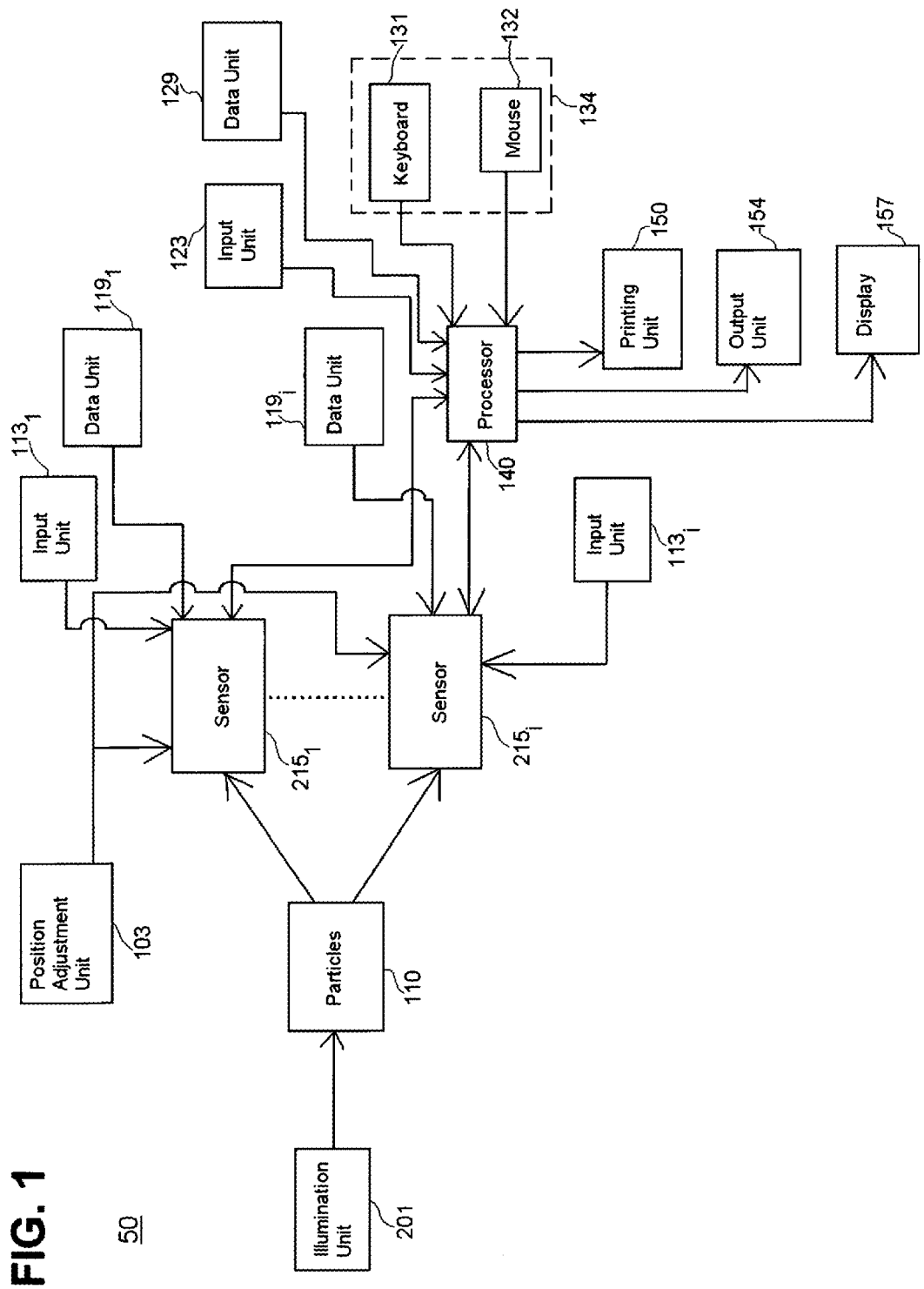

Input a parameter range for an aerosol distribution —S431

Select aerosol moment to be measured —S432

Use computational model to determine the angle with respect to an input beam for a detector to minimize the error of measurement of the selected moment —S433

Arrange detector at the determined angle with respect to an input beam —S434

Send input beam to the aerosol distribution —S435

Output aerosol moment value and uncertainty in measurement of the aerosol moment —S436

FIG. 2C

Specify one or more ranges for particle properties for an aerosol — S450

Specify either a range for a desired uncertainty of measurement of an aerosol moment by the detector or a range for a detection angle for detecting the aerosol with the detector — S452

Using the computational model, determine at least one of the following : a range for uncertainty of measurement of the aerosol moment, a range for an optimized detection angle for detecting the aerosol, and a range for an optical design parameter of the detector to optimize the moment measurement — S454

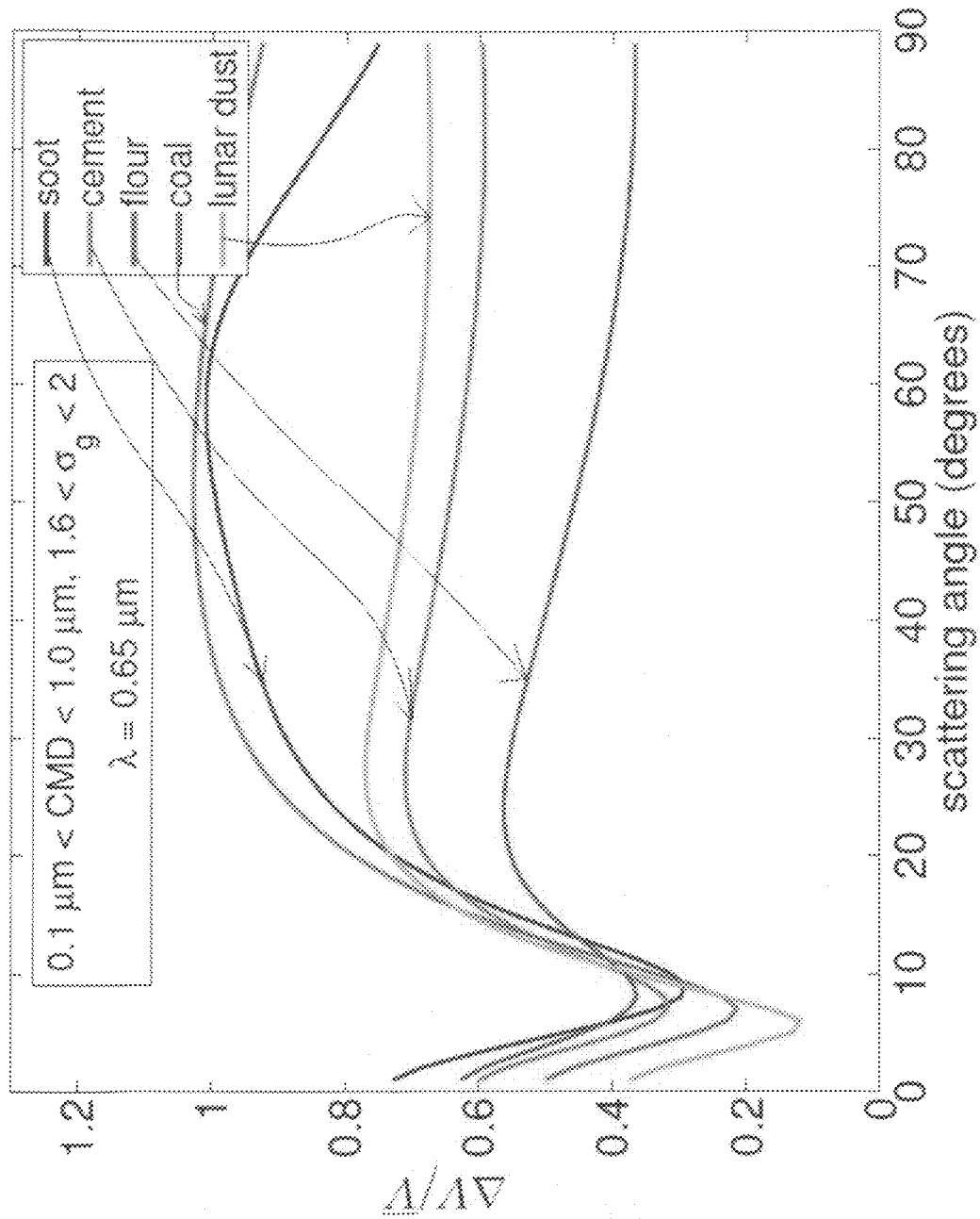

MULTI-PARAMETER SCATTERING SENSOR AND METHODS

CROSS REFERENCE TO RELATED APPLICATION

This application claims the benefit from U.S. Provisional Application No. 61/355,376, entitled "Multi-Parameter Aerosol Scattering Sensor" filed on Jun. 16, 2010, incorporated by reference herein in its entirety.

ORIGIN OF THE INVENTION

The invention described herein was made by an employee of the United States Government and may be manufactured and used by or for the Government for Government purposes without the payment of any royalties thereon or therefore.

COMPACT DISKS

The present specification incorporates by reference the entire contents of the attached two compact disks labeled Copy1 and Copy2, whereby Copy1 and Copy2 are duplicate disks. Each of Copy1 and Copy2 disks includes the following files: Fig_4A.txt (Jun. 14, 2011, 8 KB), Fig_4B.txt (Jun. 14, 2011, 8 KB), Fig_5.txt (Jun. 14, 2011, 2 KB), Fig_6A.txt (Jun. 14, 2011, 4 KB), Fig_6B.txt (Jun. 14, 2011, 4 KB), Fig_6C.txt (Jun. 14, 2011, 4 KB), Fig_6D.txt (Jun. 14, 2011, 4 KB), Fig_6E.txt (Jun. 14, 2011, 4 KB), Fig_6F.txt (Jun. 14, 2011, 4 KB), Fig_6G.txt (Jun. 14, 2011, 4 KB), Fig_6H.txt (Jun. 14, 2011, 4 KB), Fig_6I.txt (Jun. 14, 2011, 4 KB), Fig_6J.txt (Jun. 14, 2011, 4 KB), Fig_6K.txt (Jun. 14, 2011, 4 KB), Fig_6L.txt (Jun. 14, 2011, 4 KB), Fig_6M.txt (Jun. 14, 2011, 2 KB), Fig_6N.txt (Jun. 14, 2011, 2 KB), Fig_6O.txt (Jun. 14, 2011, 2 KB), Fig_6P.txt (Jun. 14, 2011, 2 KB), Fig_6Q.txt (Jun. 14, 2011, 2 KB), Fig_6R.txt (Jun. 14, 2011, 2 KB), Fig_11A.txt (Jun. 14, 2011, 1 KB), and Fig_11B.txt (Jun. 14, 2011, 1 KB). The table in each file includes the numerical data that was used to generate FIGS. 4A, 4B, 5, 6A-6R, 11A and 11B, and title of each table (file) indicates the figure to which the table pertains. The .txt files are to be read in notepad with 8 pt. Times New Roman Font. In these tables, "sg" represents the standard deviation, $\sigma_g$, indicated in the specifications. Also, "Delta_V/V" represents $\Delta V/V$ and "Delta_SA/SA" represents $\Delta SA/SA$. Each of Copy1 and Copy2 disks also includes the files: Fig_4A.xlsx (Jun. 14, 2011, 26 KB), Fig_4B.xlsx (Jun. 14, 2011, 26 KB), Fig_5.xlsx (Jun. 14, 2011, 13 KB), Fig_6A.xlsx (Jun. 14, 2011, 19 KB), Fig_6B.xlsx (Jun. 14, 2011, 19 KB), Fig_6C.xlsx (Jun. 14, 2011, 19 KB), Fig_6D.xlsx (Jun. 14, 2011, 19 KB), Fig_6E.xlsx (Jun. 14, 2011, 18 KB), Fig_6F.xlsx (Jun. 14, 2011, 19 KB), Fig_6G.xlsx (Jun. 14, 2011, 19 KB), Fig_6H.xlsx (Jun. 14, 2011, 19 KB), Fig_6I.xlsx (Jun. 14, 2011, 19 KB), Fig_6J.xlsx (Jun. 14, 2011, 18 KB), Fig_6K.xlsx (Jun. 14, 2011, 18 KB), Fig_6L.xlsx (Jun. 14, 2011, 19 KB), Fig_6M.xlsx (Jun. 14, 2011, 13 KB), Fig_6N.xlsx (Jun. 14, 2011, 13 KB), Fig_6O.xlsx (Jun. 14, 2011, 13 KB), Fig_6P.xlsx (Jun. 14, 2011, 13 KB), Fig_6Q.xlsx (Jun. 14, 2011, 13 KB), Fig_6R.xlsx (Jun. 14, 2011, 13 KB), Fig_11A.xlsx (Jun. 14, 2011, 11 KB), and Fig_11B.xlsx (Jun. 14, 2011, 11 KB). These are duplicate data tables in Microsoft Excel format.

BACKGROUND OF THE INVENTION

1. Field of the Invention

The present invention relates to a particle detection and analysis technique and apparatus, and more particularly to a method and apparatus for detecting a distribution of particles and providing integrated moment information about the distribution.

2. Description of the Related Art

Fire safety is of considerable interest in everyday activities. It is also of great concern in the context of remote, confined spaces such as on an aircraft, spacecraft, submarine and the like. In any of these situations, the occurrence of fires can jeopardize lives and crew safety, equipment and infrastructure, flight systems, mission objectives, etc. If suitable provisions are not afforded for fire prevention and mitigation, the hazards can be considerable. Early warning fire detection is one way to mitigate such hazards.

However, designing suitable particulate sensors is challenging. Conventional state of the art fire detectors suffer from significant detection errors, and the simple strategy of increasing detection sensitivity to decrease response time leads to the problematic likelihood of false alarms. Existing standards for alarms levels are mass-based, and remain somewhat primitive in their approach and performance. Furthermore, conventional fire detection systems are, at best, poorly suited to detect reduced-gravity fire signatures such as signatures that may occur on a spacecraft.

Conventional particulate sensors for fire detection thus suffer from poor accuracy and the inability to measure specific properties or multiple properties simultaneously, and typically have a physical package that is unsuitably large, massive, power consumptive, or not mechanically robust for field deployment. In addition, accurate particulate sensors for detecting particles produced by industrial processes or environmental processes are not currently available.

Disclosed embodiments of this application address these and other issues by providing methods and apparatuses for early and accurate detection of fires or other environmental events by analyzing characteristics of radiation scattered by ensembles of particles produced by fires or by other events. Sensors described in the present application measure specific aerosol properties. For example, the sensors described herein measure light that is scattered from an ensemble of particles and provide useful integrated information about this distribution of particles. The information includes integrated moment distributions, such as, for example, total surface area, total mass, total volume, etc., or mathematical combinations of these moment distributions. Embodiments of the present application disclose a computational tool to design and optimize such sensors, as well as implementation and use of these sensors in actual practice.

SUMMARY OF THE INVENTION

The present invention is directed to methods and apparatuses for detecting and measuring particles. According to a first aspect of the present invention, a method of measuring surface area by ensemble optical scattering comprises: receiving radiation scattered by an ensemble of particles, and measuring surface area of the ensemble of particles using the scattered radiation.

According to an aspect of the invention, the radiation scattered by the ensemble of particles includes photons scattered by the ensemble of particles.

According to a second aspect of the present invention, a detector based on optical scattering for measuring surface area by ensemble scattering comprises: a sensor for measuring radiation scattered by an ensemble of particles; and a processing unit for determining surface area of the ensemble of particles from a moment or an integrated moment for the ensemble of particles.

According to an aspect of the invention, the scattered radiation measured by the sensor includes photons scattered by the ensemble of particles.

According to an aspect of the invention, the detector is a scattering photometer.

According to a third aspect of the present invention, a method of detecting particles comprises: receiving radiation scattered by an ensemble of particles; determining a surface area for the ensemble of particles using the scattered radiation; and determining a characteristic of the ensemble of particles, or presence of the ensemble of particles, based on the determined surface area.

According to an aspect of the invention, the determining step includes determining a voltage value which is related to the surface area.

According to a fourth aspect of the present invention, a detector based on optical scattering for measuring surface area by ensemble scattering comprises: a sensor for measuring radiation scattered by an ensemble of particles; and a processing unit for determining a surface area for the ensemble of particles using the scattered radiation, and determining a characteristic of the ensemble of particles, or presence of the ensemble of particles, based on the determined surface area.

According to a fifth aspect of the present invention, a method for reporting and/or bounding a characteristic of a distribution of aerosols comprises: reporting and/or bounding an accuracy or confidence bound for measuring aerosols with one or more properties (a) and/or (b) and/or (c) and/or (d), and/or characterized by ranges for one or more properties (a) and/or (b) and/or (c) and/or (d), wherein (a)-(d) are the following: (a) is a wavelength of light incident on aerosols, (b) is a count median diameter or other characteristic size parameter of the aerosol size distribution, (c) is a standard deviation or other characteristic width parameter of the aerosol size distribution, and (d) is a refractive index of aerosol particles.

According to an aspect of the invention, the bounding step determines bounds for measurement uncertainty based on specified ranges for one or more modal properties and/or optical properties for the aerosol.

According to a sixth aspect of the present invention, a particle detector comprises: a sensor for measuring radiation scattered by an ensemble of aerosols; and a processor for reporting and/or bounding an accuracy or confidence bound for measuring the aerosols with one or more properties (a) and/or (b) and/or (c) and/or (d), and/or characterized by ranges for one or more properties (a) and/or (b) and/or (c) and/or (d), wherein (a)-(d) are the following: (a) is a wavelength of light incident on aerosols, (b) is a count median diameter or other characteristic size parameter of the aerosol size distribution, (c) is a standard deviation or other characteristic width parameter of the aerosol size distribution, and (d) is a refractive index of aerosol particles.

According to a seventh aspect of the present invention, a method of detecting particles comprises: receiving radiation scattered by an ensemble of particles; and determining a physical sensor parameter, or an optimal detection angle for the sensor, or a bound for an optimal detection angle for measuring at least one moment or integrated moment of the ensemble of particles, wherein the physical sensor parameter, or detection angle, or detection angle bound is determined based on one or more properties (a) and/or (b) and/or (c) and/or (d), and/or ranges of one or more properties (a) and/or (b) and/or (c) and/or (d), wherein (a)-(d) are the following: (a) is a wavelength of light incident on the particles, (b) is a count median diameter or other characteristic size parameter of the particle size distribution, (c) is a standard deviation or other characteristic width parameter of the particle size distribution, and (d) is a refractive index of particles.

According to an aspect of the invention, the method further comprises adjusting a sensor detection angle within the bound, to set an uncertainty for detection of the at least one moment or integrated moment within a predetermined range, for an anticipated range of particles parameters.

According to an aspect of the invention, the detection angle is within 10% of an optimum angle for measurement of a particles' moment average for an anticipated range of specific particle parameters.

According to an aspect of the invention, the physical sensor parameter and/or the detection angle for the sensor is/are adjusted to bound a measurement uncertainty for a moment of the ensemble of particles within 15% of a minimum measurement uncertainty achievable for an anticipated range of specific particle parameters.

According to an aspect of the invention, the at least one moment includes at least one of the $0^{th}$, $2^{nd}$, and $3^{rd}$ moment distributions of the ensemble of particles.

According to an aspect of the invention, the optimal detection angle is different from 90°, and the bound for an optimal detection angle does not include 90°.

According to an aspect of the invention, the particles are aerosols, and the determining step includes: specifying a range for one or more aerosols properties (a) and/or (b) and/or (c) and/or (d), and determining at least one of
   a range for uncertainty of measurement of the at least one moment or integrated moment,
   a range for an optimized detection angle for detecting scattered radiation from the aerosol, and
   a range for an optical design parameter of a detector to detect the aerosol, based on at least one of the other of
      a range for uncertainty of measurement of the aerosol moment by the detector, and
      a range for a detection angle for detecting scattered radiation with the detector.

According to an aspect of the invention, the particles are aerosols, and an output corresponding to the at least one moment or integrated moment for the ensemble of aerosols is related to an aerosol described by specific values of (a) and/or (b) and/or (c) and/or (d) and/or specific bounds of values of (a) and/or (b) and/or (c) and/or (d), by a method other than a direct calibration to the aerosol.

According to an aspect of the invention, the particles are aerosols, and the method further comprises calibrating a sensor to a reference aerosol, before the sensor receives the radiation scattered by the ensemble of aerosols. According to an aspect of the invention, the calibrating step calibrates an optical collection and electrical conversion efficiency for the sensor using the reference aerosol for which a moment or an integrated moment quantity has been accurately characterized, wherein the reference aerosol is different from the ensemble of aerosols receiving the radiation, and the method further comprises measuring with the sensor a value for the moment or integrated moment for the ensemble of aerosols, without recalibrating the sensor to the ensemble of aerosols.

According to an aspect of the invention, the method further comprises: selecting, before the determining step, the at least one moment or integrated moment to be measured.

According to an aspect of the invention, the method further comprises selecting a distribution for a parameter of the particles, based on a type of the particles.

According to an aspect of the invention, the method further comprises adjusting a plurality of detection angles for a plurality of moveable sensors, to measure multiple moments and/or integrated moments for the ensemble of particles. According to an aspect of the invention, the plurality of detection angles are adjusted based on preset confidence bounds for a measurement of each of the moments and integrated moments by the sensors.

According to an aspect of the invention, the method further comprises selecting, from among a plurality of fixed sensors, a sensor arranged at an angle closer to the optimal detection angle than the other of the fixed sensors, and measuring, using the selected sensor, the moment or integrated moment for the ensemble of particles.

According to an aspect of the invention, a formalism based on Mie scattering is used in the determining step.

According to an aspect of the invention, the properties (b) and (c) are determined based on a particle distribution which is Gaussian, lognormal or Rosin-Rammler.

According to an aspect of the invention, the method weights the distribution of the ensemble of particles and normalizes the distribution to provide a constant value of the moment or integrated moment.

According to an aspect of the invention, the determining step calculates scattering from a family of particle distributions which are characterized by one or more properties (a) and/or (b) and/or (c) and/or (d) or ranges of one or more properties (a) and/or (b) and/or (c) and/or (d), and which have the same moment of integrated moment.

According to an aspect of the invention, the physical sensor parameter describes an optical configuration of a sensor used to detect ensemble of particles, and the method sets the physical sensor parameter so as to optimize the optical configuration for the sensor.

According to an aspect of the invention, a method of detecting particles comprises: providing a detector having a physical sensor parameter which is determined for measuring at least one moment or integrated moment of the ensemble of particles, wherein the physical sensor parameter, or detection angle, or detection angle bound is determined based on one or more properties (a) and/or (b) and/or (c) and/or (d), and/or ranges of one or more properties (a) and/or (b) and/or (c) and/or (d), wherein (a)-(d) are the following: (a) is a wavelength of light incident on the particles, (b) is a count median diameter or other characteristic size parameter of the particle size distribution, (c) is a standard deviation or other characteristic width parameter of the particle size distribution, and (d) is a refractive index of particles; and detecting particles by collecting radiation scattered by the particles using the detector.

According to an eighth aspect of the present invention, a detector for detecting particles comprises:

a sensor for receiving radiation scattered by an ensemble of particles;

a processor for determining a physical parameter for the detector, or an optimal detection angle or a bound for an optimal detection angle, for measuring at least one moment or integrated moment of the ensemble of particles, the physical parameter, or detection angle, or detection angle bound being determined based on one or more of properties (a) and/or (b) and/or (c) and/or (d) or ranges for one or more of properties (a) and/or (b) and/or (c) and/or (d), wherein (a)-(d) are the following:

(a) is a wavelength of light incident on the particles,
(b) is a count median diameter or other characteristic size parameter of the particle size distribution,
(c) is a standard deviation or other characteristic width parameter of the particle size distribution, and
(d) is a refractive index of particles.

According to an aspect of the invention, the particles are aerosols, and the processor relates a detector output corresponding to the at least one moment or integrated moment for the ensemble of aerosols, for a desired aerosol described by one or more specific value of (a) and/or (b) and/or (c) and/or (d) and/or one or more specific bound of values of (a) and/or (b) and/or (c) and/or (d), without using direct calibration to the aerosol.

According to an aspect of the invention, the detector selects, before determining an optimal angle, the at least one moment or integrated moment to be measured.

According to an aspect of the invention, the particles are one of solid phase organic or inorganic particles, liquid droplets, pyrolysis products and/or condensed polycyclic hydrocarbons.

According to an aspect of the invention, the particles are aerosols.

According to an aspect of the invention, the detector includes a plurality of moveable sensors whose detection angles with respect to an axis of the radiation is changeable, and the processor adjusts the detection angles for the plurality of sensors to measure multiple moments and/or integrated moments for the ensemble of particles. The detection angles for the plurality of sensors may be adjusted based on desired confidence bounds for a measurement of each of the moments and integrated moments by the plurality of sensors.

According to an aspect of the invention, the detection angles for the sensors may be adjusted iteratively for measurement of multiple moments, and the processor outputs confidence bounds for the measurement of each of the moments by the sensors.

According to an aspect of the invention, the detector includes a plurality of fixed sensors, and the processor selects, from among the plurality of fixed sensors, a sensor arranged at an angle which most closely matches the optimal detection angle among the fixed sensors, and the selected sensor is used to measure the moment or integrated moment for the ensemble of particles.

According to an aspect of the invention, the detector includes a plurality of fixed sensors and moveable sensors, and the processor selects a plurality of the moveable and fixed sensors, for measuring a plurality of moments and/or integrated moments for the ensemble of particles, and/or for measuring characteristics of one or more types of particles, and for bounding an uncertainty for the measurement(s).

According to an aspect of the invention, the placement and/or detection angles of multiple sensors are adjusted to reduce resulting uncertainty in the measurement of total mass of the ensemble of particles with one sensor, and resulting uncertainty in the measurement of total surface area of the ensemble of particles.

According to an aspect of the invention, the particles are aerosols, and the sensor is calibrated to a reference aerosol, before the sensor receives the radiation scattered by the ensemble of aerosols. According to an aspect of the invention, an optical collection and electrical conversion efficiency for the sensor is calibrated using the reference aerosol for which a moment or an integrated moment quantity has been accurately characterized, wherein the reference aerosol is different from the ensemble of aerosols receiving the radiation, and the sensor measures a value for the moment or integrated moment for the ensemble of aerosols without being recalibrated to the ensemble of aerosols.

According to an aspect of the invention, the ensemble of particles measured by the sensor may include aerosols produced by a fire, environmental aerosols, industrial aerosols, and particles suspended in a liquid medium.

According to an aspect of the invention, the detector detects solid phase organic and inorganic particles, liquid droplets, pyrolysis products and condensed polycyclic hydrocarbons, within predetermined confidence bounds for the measurements for each of the solid phase organic and inorganic particles, liquid droplets, pyrolysis products and condensed polycyclic hydrocarbons.

According to an aspect of the invention, the particles measured by the detector are airborne, or are present in a low gravity environment, or in a void, or outer space, or in a fluid.

According to an aspect of the invention, the detector provides integrated information about the distribution of particles, wherein the information provides a value for a moment or combination of moments for the distribution of particles.

According to an aspect of the invention the integrated information provided by the detector includes at least one of
 total particle mass,
 total particle volume,
 total particle surface area,
 value for a fourth moment which is proportional to the total projected area of a material sedimenting as particles, from a stationary fluid, and
 value for a fifth moment which is proportional to the mass flux of the material sedimenting as particles
  and/or a combination of at least two of
  total particle mass,
  total particle volume,
  total particle surface area,
  value for a fourth moment which is proportional to the total projected area of a material sedimenting as particles, from a stationary fluid, and
  value for a fifth moment which is proportional to the mass flux of the material sedimenting as particles.

According to an aspect of the invention, the processor uses physical, optical or geometrical characteristics of the ensemble of particles determined based on assumptions regarding the ensemble of particles, to perform at least one of the following:
 determine sensor placement and/or angle,
 determine optical configuration for the sensor when measuring the ensemble of particles,
 control the sensor to perform at least one measurement to determine spatial and/or temporal evolution as the ensemble of particles ages,
 control the sensor to perform at least one measurement for characterizing at least one modal property of the ensemble of particles,
 control the sensor to determine a moment for the ensemble of particles and to bound an uncertainty in the measurement of the moment, and
 calculate scattered power and/or surface area of the ensemble of particles.

According to an aspect of the invention, bi-directional communication is established between the processor and sensor, and/or between the processor and a user.

According to an aspect of the invention, the bi-directional communication is accomplished wirelessly.

According to an aspect of the invention, the detection angle for the sensor is adjusted within ±10% of an optimum angle for measurement of the particles' moment average, for an anticipated range of specific particle parameters.

According to an aspect of the invention, the physical sensor parameter or the detection angle for the sensor is adjusted to bound a measurement uncertainty for a moment of the ensemble of particles within ±10% of a minimum measurement uncertainty (confidence bound), for an anticipated range of specific particle parameters.

According to an aspect of the invention, after the sensor has been calibrated using a first aerosol, responsivity of the sensor exposed to a second aerosol different from the first aerosol is measured in real-time, without additional calibration of the sensor to the second aerosol. Modal parameters and/or refractive index or other properties of the second aerosol may be specified within some ranges. A bound for the uncertainty in the resulting measurement of the second aerosol with the sensor may also be output.

According to an aspect of the invention, a measurement for an ensemble of aerosols is performed at a detection angle which reduces or minimizes a measurement error for a moment of the ensemble of particles, wherein the detection angle is significantly different from 90°.

According to an aspect of the invention, the sensor is used to determine various moments of an aerosol distribution.

According to an aspect of the invention, the sensor uses a dependence of a scattering signature of the ensemble of particles on a detection angle and/or on a wavelength of radiation incident on the ensemble of particles, to extract compositional information about the particles.

According to an aspect of the invention, the sensor outputs a value for the at least one moment or integrated moment for the ensemble of particles, the at least one moment or integrated moment being based on total scattered power by the ensemble of particles, and the sensor also outputs an uncertainty in the resulting measurement of the at least one moment or integrated moment.

According to an aspect of the invention, the processor is normalized to a fixed moment integral or mathematical combinations of moment integrals, and the processor adjusts at least one of optical collection aperture for the sensor and detector angle for the sensor, based on one or more range and/or one or more value of at least one of incident radiation wavelength, optical collection aperture of the sensor, detector angle for the sensor, polarization state of radiation incident on the ensemble of particles, characteristic size parameter of the particle size distribution, characteristic width parameter of the particle size distribution and refractive index of the particles.

According to an aspect of the invention, the processor selects a class of particles to be detected by the sensor, by selecting one or more ranges for properties of the particles to be detected, and determines a value or range for sensor detection angle for detection of one or more moments or combination of moments for the distribution of particles, and an uncertainty in the resulting measurement of the one or more moments or combination of moments.

According to an aspect of the invention, modal conditioning is applied to the input beam of incident radiation directed to the ensemble of particles.

According to an aspect of the invention, stray light is suppressed by confocal detection, whereby matched spatial apertures precede the sensor. The apertures may be embodied as the entrance face of an optical fiber, and the fiber characteristics specify the lateral dimensions of the optical sample volume of the ensemble of particles and the F-number or Numerical Aperture of the collection optics of the sensor.

According to an aspect of the invention, the sensor is recessed in a cavity, from the sample volume of the ensemble of particles.

According to an aspect of the invention, transmitting and receiving optics are located around a cavity, through which the aerosol sample passes. The aerosol may be actively sampled (i.e. using a pump), or can enter the cavity passively. The optics themselves may be located behind secondary cavities.

According to an aspect of the invention, the processor adjusts placement and/or detection angles of multiple sensors to detect different moments or combinations of moments for the ensemble of particles.

According to an aspect of the invention, the processor provides to the sensor aerosol-specific data which includes a list of optimal angles or ranges around optimal angles for a plurality of particle types.

According to an aspect of the invention, the processor provides to the sensor predetermined detection angles for measuring different distribution moments for different ensembles of particles, the predetermined detection angles being included in a database.

According to an aspect of the invention, a sensor detection angle is adjusted within ±5%, or ±10%, or ±15%, or ±20% of an optimum angle for measurement of a particles' moment average or combination of moments for an anticipated range of specific particle ensemble parameters.

According to an aspect of the invention, the physical sensor parameter or the detection angle for the sensor is adjusted to bound a measurement uncertainty for a moment of the ensemble of particles within ±5%, or ±10%, or ±15%, or ±20% of a minimum measurement uncertainty that is achievable for an anticipated range of specific particle ensemble parameters.

BRIEF DESCRIPTION OF THE DRAWINGS

Further aspects and advantages of the present invention will become apparent upon reading the following detailed description in conjunction with the accompanying drawings, in which:

FIG. 1 is a general block diagram of a system including a multi-parameter particle scattering sensor for detecting and analyzing ensembles of particles, according to an embodiment of the present invention;

FIG. 2A is a flow diagram illustrating the design and operation of a sensor for providing accurate measurement for an ensemble of particles for fire detection, environmental monitoring, industrial processes and other applications, according to a first embodiment of the present invention;

FIG. 2B is a flow diagram illustrating the design and operation of a sensor for determining an aerosol moment with minimum measurement uncertainty, according to a second embodiment of the present invention;

FIG. 2C is a flow diagram illustrating the design and operation of a sensor for optimizing an aerosol moment measurement or determining measurement uncertainty bounds, according to a third embodiment of the present invention;

FIG. 3 illustrates a schematic optical geometry of a Multi-Parameter Aerosol Scattering Sensor (MPASS), according to an embodiment of the present invention;

FIG. 4A illustrates an exemplary scattered power versus scattering angle for constant aerosolized volume, according to an embodiment of the present invention;

FIG. 4B illustrates an exemplary volume concentration versus scattering angle for constant scattered power, according to an embodiment of the present invention;

FIG. 5 illustrates an exemplary graph showing relative error in volume concentration vs. angle, according to an embodiment of the present invention;

FIGS. 6A-6R illustrate exemplary determination of the optimal measurement/scattering angle θ between the detector and the optical axis, for various model parameter ranges for various aerosols for measuring the $2^{nd}$ (surface area) and $3^{rd}$ (mass) moments of the aerosols according to an embodiment of the present invention;

FIG. 7 illustrates a multi-angle instrument consisting of an arbitrary number of angularly spaced detectors, according to another embodiment of the present invention;

FIG. 8 illustrates the interior of an exemplary MPASS SAME-R flight sensor, according to an embodiment of the present invention;

FIG. 9 illustrates an exemplary MPASS flight package for ISS SAME-R, according to an embodiment of the present invention;

FIG. 10A illustrates a laboratory apparatus for MPASS calibration and performance evaluation and validation of the computational model, according to an embodiment of the present invention;

FIG. 10B illustrates a laboratory apparatus for MPASS calibration configuration for calibration with a polydisperse aerosol, according to an embodiment of the present invention;

FIG. 10C illustrates a laboratory apparatus for MPASS calibration configuration for calibration with a monodisperse aerosol, according to an embodiment of the present invention; and FIGS. 11A and 11B illustrate exemplary MPASS computational model data vs. experimental data for total mass (FIG. 11B) and surface area (FIG. 11A), according to an embodiment of the present invention.

DETAILED DESCRIPTION

Aspects of the invention are more specifically set forth in the accompanying description with reference to the appended figures. FIG. 1 is a general block diagram of a system including one or more multi-parameter particle scattering sensors for detecting and analyzing ensembles of particles according to an embodiment of the present invention. The system 50 illustrated in FIG. 1 includes the following components: an illumination unit 201 which illuminates an area 110 in which particles may be present; one or more multi-parameter particle scattering sensors $\mathbf{215}_1, \ldots, \mathbf{215}_i$; a position adjustment unit 103; one or more input units $\mathbf{113}_1, \ldots, \mathbf{113}_i$; one or more data units $\mathbf{119}_1, \ldots, \mathbf{119}_i$; a processor 140; an input unit 123; a data unit 129; a display 157; a user input unit 134; an output unit 154; and a printing unit 150. Operation of the system 50 in FIG. 1 will become apparent from the following discussion.

The illumination unit 201 sends radiation such as, for example, light, to area 110 in which particles may be present. The illumination unit 201 may include any type of device that produces radiation. Examples include lasers, lamp arrangements, LEDs, fiber optic arrangements, etc., and the radiation may be any type of radiation.

The particles in area 110 may be airborne, or otherwise present in a low gravity environment, void/space, enclosed spaces, fluid, etc. The particles may naturally exist in the environment or may have been generated by any processes that produce distributions of particles in the air or in other type of environment such as a low gravity environment, severe conditions environment, void/space, enclosed spaces, water, etc. Exemplary processes include fires, industrial processes, electrical events, food processing operations, environmental processes that produce airborne particle distributions, etc. Fires, for example, produce aerosol particulates, mills produce airborne flour particles, coal mines produce coal dust, industrial facilities produce dust from various chemicals, etc.

The one or more sensors $215_1, \ldots, 215_i$ receive light scattered by the distribution of particles in area 110 and provide integrated information about the distribution of particles, in a manner discussed in detail below. Such information may include, for example, total particle mass, total particle volume, total particle surface area, value for any higher moment for the particles distribution such as the fourth moment which is proportional to the total projected area of the material sedimenting from a stationary fluid, the fifth moment which is proportional to the mass flux of material for this same case, etc.

The position adjustment unit 103 may move one or more of the sensors/detectors $215_1, \ldots, 215_i$ so that their position and/or receiving angle with respect to the particle area 110 and the optical axis of the illumination unit 201 change. Input units $113_1, \ldots, 113_i$ may be used to input to sensors $215_1, \ldots, 215_i$, before the measurement, or during a measurement in real-time, information about the distribution of particles in area 110, or other information pertinent to measurement of light scattered from the ensemble of particles. Data units $119_1, \ldots, 119_i$ may provide to sensors $215_1, \ldots, 215_i$ previously saved data regarding characteristics of particle distributions such as, for example, median size characteristics for the distribution, standard deviation of the distribution, optical or other type of information regarding the distribution of particles, mathematical model information for the distribution, etc.

In an alternative embodiment, the system 50 can be configured as a collection of multiple fixed detectors $215_1, \ldots, 215_i$ which are arranged at certain angles with respect to the axis of the illumination unit 201. The angles may be determined in accordance with the methods of the present invention. The processor 140 can then be used to select which of these detectors are used to measure a particular type of particles/particle distribution and to bound the resulting measurement uncertainty. For example, the processor 140 may control multiple detectors to measure distributions of particles of different kind, with each kind of particles being measured by one or more fixed dedicated detectors.

In another alternative embodiment, the system 50 includes both moveable detectors and fixed detectors in the detector set $215_1, \ldots, 215_i$. In addition to changing the angular position of one or more moveable detectors among $215_1, \ldots, 215_i$, the system 50 can be configured to include a collection of multiple fixed detectors among $215_1, \ldots, 215_i$. The system 50 can then optimize selection and placement of detectors to measure a particular particle type, and to bound the resulting measurement uncertainty. For example, the processor 140 may control multiple detectors to measure distributions of particles of different kind, with each kind of particles being measured by one or more of the fixed dedicated detectors. Processor 140 may also control movement (such as distance to particle ensemble 110 and/or angle with respect to the axis of the illumination unit 201) for the moveable detectors, to measure multiple characteristics of particle ensemble 110 for multiple detector angles, and to bound the resulting measurement uncertainty.

Figure 7:
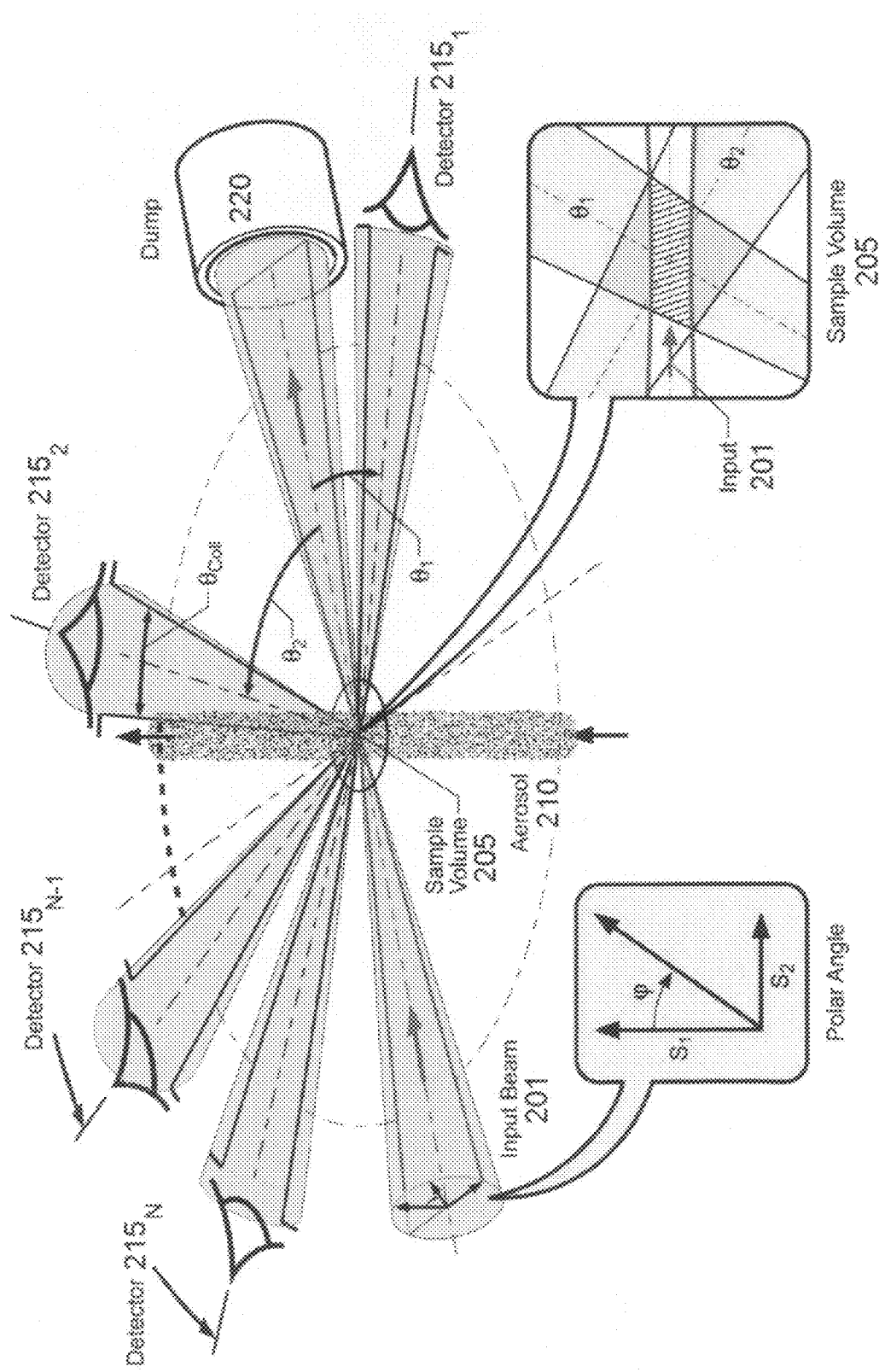

FIG. 7 illustrates an exemplary embodiment including fixed detectors.

Processor 140 communicates with sensors $215_1, \ldots, 215_i$ and may send to the sensors parameters or conditions for the measurements such as angles or distances at which the sensors should be placed. Processor 140 may also input characteristics of the particle distribution or measurement conditions determined based on assumptions regarding the particle distribution, may control and monitor the behavior of the sensors, and may receive information regarding measurement results from the sensors. The processor 140 may be connected to an input unit 123 and data unit 129 that provide, before the measurement, or during a measurement in real-time, information about the particle distribution in area 110, or other information pertinent to measurement of light scattered from the ensemble of particles, previously saved data regarding characteristics of particle distributions such as, for example, median size characteristics for the distribution, standard deviation of the distribution, optical or other type of information regarding the distribution of particles, mathematical model information for the distribution, etc. The processor 140 may then perform one or more of the following: determine details for sensor placement such as angle with respect to the axis of the optical illumination unit; determine optical configuration details for sensors and control sensors accordingly; control sensors to perform measurements to determine spatial/temporal evolution as the distribution of particles ages; control sensors to perform measurements for characterizing the modal properties of particle distribution; control sensors to determine a particle distribution moment and determine uncertainty for measurement of the moment; calculate total scattered power from particles. The processor 140 may monitor control sensors to perform other measurements as well, as described in more detail below.

Although shown in FIG. 1 as one separate unit, the processor 140 may include one or more stand-alone units connected to sensors $215_1, \ldots, 215_i$ and/or may include processing units incorporated into each of sensors $215_1, \ldots, 215_i$. The processor 140 may include one or more (micro)processors, purpose built hardware such as, for example, FPGA, ASIC, etc., software systems and applications, software packages, etc. Software packages that may be part of processor 140 may be recorded on a computer readable medium such as a memory device, RAM, CD/DVD/USB drives, handheld memory device, etc., and/or may be part of a physical device such as one or more (micro)processors or other electrical systems.

A user may view outputs of measurements via display 157, and may input commands to the processor 140 or to the sensors through processor 140 via the user input unit 134. In the embodiment illustrated in FIG. 1, the user input unit 134 includes a keyboard 131 and a mouse 132, but other conventional input devices such as a touch-screen display, handheld unit, etc. could also be used. Bi-directional communication with the sensor, and/or processor, and/or other elements of system 50 may also be accomplished wirelessly. In an exemplary embodiment, processor 140 may be controlled wirelessly by a user and may also communicate wirelessly with one or more sensors among $215_1, \ldots, 215_i$.

Elements of the measurement system 50 may also be controlled automatically.

A printing unit 150 may receive the measurement results and generates a hard copy of the results data. In addition to or as an alternative to generating a hard copy of the measurement results, the results may be returned to the user as a file, e.g., via a portable recording medium or via a network (not shown). The display 157 receives and displays the measurement results. The measurement results may also be sent to output unit 154 which may perform further operations on the measurement results for various purposes. Output unit 154 may be a database including a recording medium for storing and processing results, a module that performs further processing of the data, etc.

Although the various input units, data units and processor components of FIG. 1 are illustrated as discrete elements, such an illustration is for ease of explanation and it should be recognized that certain operations of the various components may be performed by the same physical device, e.g., by one or more microprocessors or devices. The data units shown in FIG. 1 may include a computer readable medium such as a memory device, RAM, CD/DVD/USB drives, handheld memory, etc.

Operation of the sensors $215_1, \ldots, 215_i$ will be next described in the context of aerosol detection and analysis, and in some cases, in the context of fire detection. However, the principles of the current invention apply equally to detection and analysis of aerosols that are not a product of fire. Exemplary aerosols which are not a product of fire are environmental or industrial aerosols. The principles of the current invention also equally apply to detection and analysis of other particle systems, such as, for example, particles suspended in a liquid medium, whose light scattering behavior may be described by the computational model presented in detail below.

Preventing fires in households, industrial settings, and other buildings or terrestrial environments is imperative for ensuring the safety of inhabitants and workers and integrity of equipment. Preventing fires in spacecraft, submarines, vessels, planes, cars or other vehicles, or in remote habitats is always the first line of defense to avoid a fire that compromises the missions, hardware, and crew. If a fire occurs, the objective is to detect the associated fire signatures at the earliest possible time from inception, thus minimizing propagation and collateral damage while providing maximal margin for suppression. If suitable provisions are afforded for fire prevention and mitigation, the hazards can then be considerably diminished by way of early warning fire detection. Knowledge of the particulate and/or gaseous fire signatures as they occur on Earth or under the unique combination of a reduced-gravity environment and materials typical of space flight applications, or in an underground/underwater environment is essential for the design of fire detectors for terrestrial, spacecraft, underwater, underground applications or other types of applications.

Exemplary disclosed embodiments of this application implement sensors for rapid and reliable early warning fire detection which significantly reduce the likelihood of false alarms. The embodiments of the present application are enabled by a detailed understanding of particle ensemble behavior and fire signatures, such as, for example, reduced-gravity fire signatures.

The present application describes a particulate detector. This detector determines various moments of distributions of particles, such as, for example, aerosols. These quantities can be correlated with the specific materials being pyrolyzed, and potentially the spatial/temporal evolution as the aerosol ages.

In one exemplary implementation, the sensor is used to determine various moments of aerosol distributions. A sensor used for analysis of aerosols is also called a Multi-Parameter Aerosol Scattering Sensor (MPASS) in the present application.

The principles of the current invention described with respect to the MPASS apply equally to sensors used for analysis of other ensembles of particles (besides aerosols) whose light scattering behavior may be described by the computational model presented in detail below.

The development of the MPASS initiated with the construction of a robust, first-principles optical scattering model. The model incorporates all aspects of the particle properties and distribution, as well as the physical aspects of the illumination source and collection geometry. A novel feature of this model involves a weighting function to normalize the various integral moments, providing constant values independent of the underlying modal properties of the aerosol. The result of this normalization process allows parametric behaviors to be investigated and optimized, and bounds the absolute measurement error for a specified optical configuration.

One exemplary sensor determines both the total surface area and mass of an aerosol, corresponding to the second and third moments of the distributions, respectively. A methodology for designing a sensor with the desired response function is described below. Test results that demonstrate the performance of prototype devices are presented in FIGS. 5-6R and 11A-11B.

The sensor of the present invention is a scattering photometer or scattering nephelometer. It measures light that is scattered from an ensemble of particles (as opposed to single particle counting), and provides useful integrated information about this distribution of particles, e.g. total mass, total volume, total surface area, etc. These integrated properties (e.g. total mass, total volume, total surface area) are referred to as the moments of the particle distribution. The present invention further includes a computational model developed to design and optimize the family of optical scattering sensors of the invention, and the development/embodiment of a working sensor of the invention that proceeds on this basis.

In an exemplary embodiment, a single sensor of the present invention is capable of fully characterizing the modal properties of a given particulate aerosol. Features such as the angular or wavelength dependence of the scattering signature may also be exploited to extract compositional information via the particle refractive index. Detection time may be decreased (by way of increased sensitivity, for example), while eliminating false triggers. This may be implemented using the characterization of the various fire signatures and their spatial/temporal evolution, as well as the properties of the associated nuisance background aerosols.

The design challenge for a scattering photometer is that, generally, a user does not have a detailed a priori knowledge of the aerosol being measured, i.e. the particle size distribution and physical properties of the particles themselves. The present application designs and optimizes a sensor such that the sensor is able to provide the most accurate measure of the desired integrated moments given a range of particle and distribution properties.

Computational Model

The kernel of the model for designing and optimizing the family of optical scattering sensors of the invention is a calculation of how individual particles scatter light. The general formalism is based on Mie scattering, which provides a method for calculating the scattering from spherical particles. The formalism can also be generalized to non-spherical particles using T-matrix theory. The kernel handles all particle properties, such as their size, shape, and refractive index.

The model can also accommodate an arbitrary polarization state for the incident beam. It also assumes, in one exemplary embodiment, independent, single scattering by the particles. The independent scattering assumption is a good one, as the particles typically exhibit uncorrelated motion. The single scattering assumption is also a good one, as the regime in which particulate sensors are typically operated satisfies this assumption.

Mathematical models for various distributions of particles are used in the construction of an integral that calculates how an ensemble of particles scatters light. Exemplary mathematical models for distributions of particles, known as the particle size distribution, include Gaussian, lognormal, Rosin-Rammler, or other distributions. It has been shown that the majority of aerosols encountered adhere closely to these distributions. For illustration, the Rosin-Rammler distribution is applicable to more coarsely dispersed dusts and sprays. The power function distribution is often applied to characterize atmospheric aerosols, whereas a Gaussian distribution has been shown to well characterize relatively monodisperse aerosols. A given particle size distribution is typically characterized by its average value (mean) and its standard deviation about its average value (i.e. its width). In the exemplary model implemented by the present invention, the particle size distribution is considered to be log-normal, characterized by its count mean diameter (CMD) and geometric standard deviation ($\sigma_g$).

One of the novel features of the model is that the distribution is weighted, or normalized to provide a constant value of a particular moment. For example, in the context of one exemplary embodiment, one can have a family of particle distributions that differ in the width of the distribution (e.g., $\sigma_g$), where the peak occurs (e.g., CMD), etc., but all these distributions have the same total mass (or other moment). The scattering from this family of lognormal (or other) distributions is then calculated, where, for example, the median diameter, standard deviation, and particle properties vary throughout some range, but every distribution has the same amount of mass (or surface area, or other integrated moment).

The method implemented by the model and the sensor of the invention solve a straightforward, practical problem. In using such a sensor, the essential problem statement is, "I don't know the exact distribution of the particles in the aerosol around me, or the precise properties of these particles. I might know that the median diameter and standard deviation of the distribution lie within some range, and similarly for the particle refractive index. However, I would like this sensor to report the total mass concentration (or other moment) of this aerosol as accurately as possible."

Once normalization is performed and the family of integrated, constant-moment scattering functions is generated, a sensor is designed, evaluated, and optimized on this basis. For example, in one exemplary embodiment, if some range for each of the distribution properties (e.g., median, width, etc.) is specified, and some range for the particle properties (e.g. refractive index, shape, etc.) is specified, the model can then be used to optimize the optical configuration. Given these ranges, the model can output, for example, that the minimum uncertainty for the measurement of mass concentration (or other moment) is obtained by using excitation wavelength "A," taking an aperture of angular subtense "B," and locating it at angle "C" relative to the optical axis.

In addition to optimizing the optical configuration, the model calculates the total scattered power, which is important in designing and building an actual device. The model also calculates the uncertainty in the resulting measurement. For example, if the device was optimized for a specified set of ranges in distribution and particle properties, the model is able to calculate the resulting uncertainty in the measurement of total mass (or other moment property). Specifically, the model can tell how accurate the sensor actually is in practice. The model is generalized, in the sense that it will incorporate any mathematical definition for uncertainty. The results presented in the included figures use the common definition for the standard deviation of a distribution. This is statistically valid in this case, due to the large number of aerosol properties and ranges being considered.

The model may also incorporate specialized transforms and integration methods to calculate the scattered power for arbitrarily large angular collection apertures placed at arbitrary locations, and to do so with reasonable run-times on modest computational platforms.

As mentioned above, the mathematical optical scattering model is structured such that it is normalized to a fixed moment integral, or mathematical combinations of moment integrals. This result is then used to optimize the design and performance of a sensor, for example to measure specific moment integrals or combinations of moment integrals. This result may also be applied to specify ranges in physical parameters (e.g., illumination wavelength, collection aperture, collection angle, polarization state in exemplary embodiments) to construct a sensor that is optimized to measure specific moment integrals or combinations of moment integrals. This result is also used to calculate or bound the uncertainty of the measurement provided by the sensor. Specialized transforms and integration methods are used to afford the calculation for arbitrarily large angular collection apertures placed at arbitrary locations, and to do so with reasonable run-times on modest computational platforms.

Figure 2A:
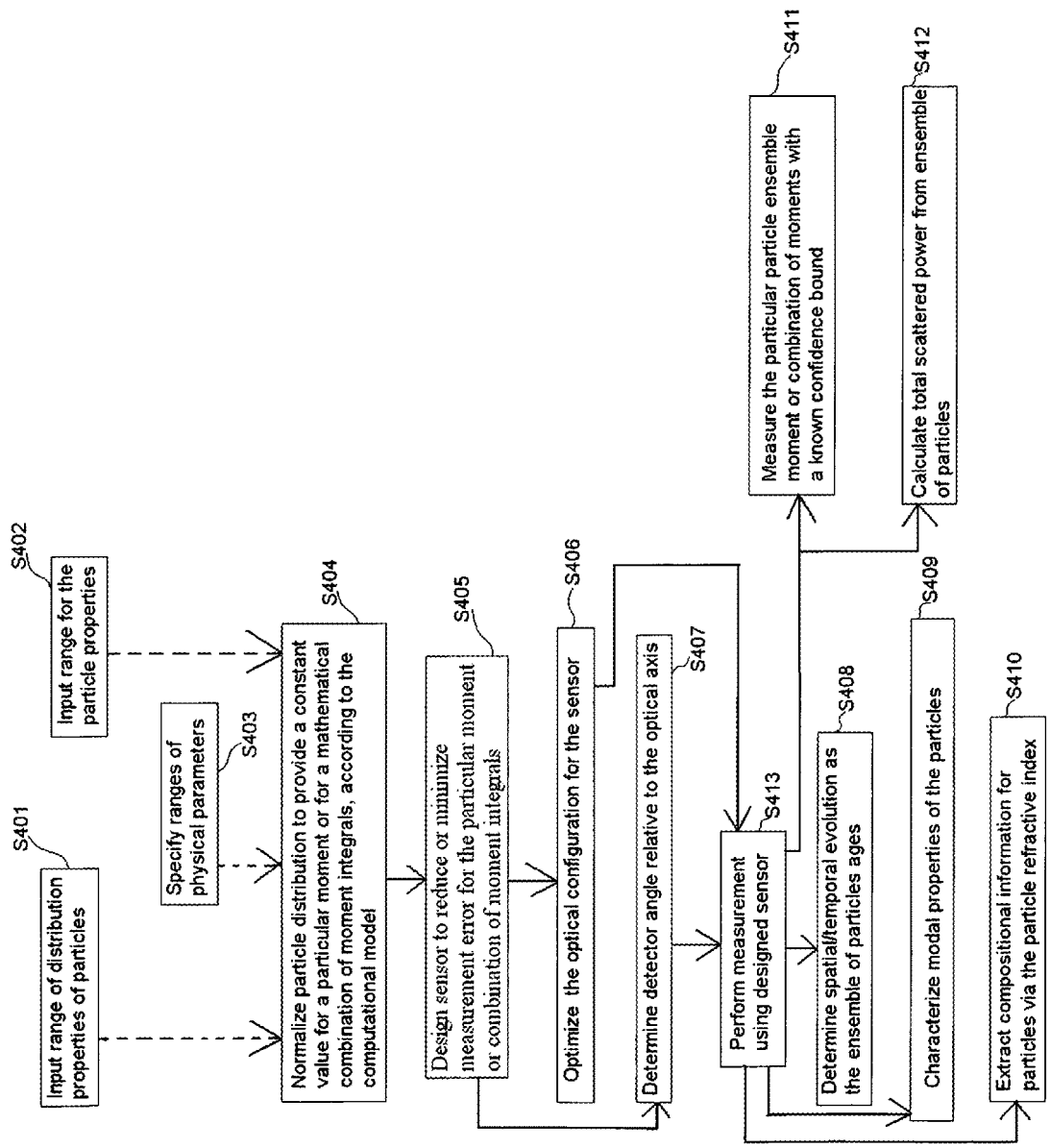

FIG. 2A is a flow diagram illustrating the design and operation of a sensor for providing accurate particle measurement for a distribution of particles for fire detection, environmental monitoring and other applications, according to a first embodiment of the present invention. As shown in FIG. 2A, a range of distribution properties of particles is first input (S401). Exemplary distribution properties are median size, width of distribution, etc. A range for the particle properties may additionally, or alternatively, be input (S402). Exemplary particle properties may be the refractive index, shape, etc. Ranges of physical parameters may additionally, or alternatively, be specified (S403). Exemplary physical parameters include illumination wavelength for radiation incident on the particles, collection aperture for the sensor, collection angle for the sensor, polarization state of radiation.

The particle distribution is then normalized to provide a constant value for a particular moment or for a mathematical combination of moment integrals, according to the computational model described in the present invention (S404). A sensor is then designed to reduce or minimize measurement error for the particular moment or combination of moment integrals (S405). The design of the sensor may include optimizing the optical configuration for the sensor (S406) and/or determining the detector angle relative to the optical axis (S407), or determining other sensor parameters that help reduce the moment measurement error, as indicated by the model.

Once the sensor is designed, a measurement is performed (S413). Based on the measurement, the spatial/temporal evolution as the distribution of particles ages may be determined (S408), the modal properties of the particulate distribution may be characterized (S409), compositional information for particles may be extracted via the particle refractive index (S410), the particular particle distribution moment or combination of moments may be measured with a known confidence bound (S411), and the total scattered power from distribution of particles may be calculated (S412).

While the methods of the present invention and the operation of various sensors is next described in the context of aerosol detection and analysis (and in some cases, in the context of fire detection), the principles of the current invention apply equally to detection and analysis of aerosols that are not a product of fire. Exemplary aerosols which are not a product of fire are environmental or industrial aerosols. Methods and apparatuses/sensors of the current invention also apply equally to detection and analysis of other particle systems which are not aerosols, such as, for example, particles suspended in a liquid medium, whose light scattering behavior may be described by the computational model presented in detail below.

FIG. 2B is a flow diagram illustrating the design and operation of a sensor for determining an aerosol moment with minimum measurement uncertainty, according to a second embodiment of the present invention. As shown in the method of FIG. 2B, a parameter range for an aerosol distribution is input (S431). An aerosol moment to be measured is selected (S432), and the computational model is used to determine the angle with respect to an input beam for a detector to minimize the error of measurement of the selected moment (S433). After the angle has been determined, the detector is arranged at the determined angle with respect to an input beam (S434) and the input beam is sent into the aerosol distribution (S435) and the aerosol moment and the uncertainty in measurement of the aerosol moment are output (S436).

FIG. 2C is a flow diagram illustrating the design and operation of a sensor for optimizing an aerosol moment measurement or determining measurement uncertainty bounds, according to a third embodiment of the present invention. One or more ranges for particle properties for an aerosol is/are specified (S450), and either a range for a desired uncertainty of measurement of an aerosol moment by the detector is specified or a range for a detection angle for detecting the aerosol with the detector is specified (S452). Using the computational model, at least one of the following is then determined: a range for uncertainty of measurement of the aerosol moment by the detector, a range for an optimized detection angle for detecting the aerosol with the detector within a range of minimum uncertainty, and a range for an optical design parameter of the detector to optimize the moment measurement (S454).

The methods shown in the above figures represent just some of the methods for detector design and aerosol detection that are afforded by the computational model disclosed in the present application. Another method includes selecting an aerosol class to be detected, by selecting ranges for properties of the aerosol to be detected, and determining a placement angle (i.e., detection angle) or a range for the placement angle for the detector to detect a moment of aerosols in that class within a predetermined detection error range. The method may be applied for detection of multiple moments, such as, for example, for detection of the $0^{th}$, $1^{st}$, $2^{nd}$ and $3^{rd}$ moment distributions of the aerosol. For a broad anticipated range of aerosol parameters generally describing the aerosol, the method provides the ability to select detector angles (i.e., angles of detector with respect to optical axis of the illumination unit that illuminates the aerosol distribution) within a certain percent of an optimum angle (e.g., an angle producing the most accurate measurement) for measurement of any aerosol moment average, and also output confidence bounds for the measurement of the aerosol moment average. For example, the detector can measure properties of various aerosols at a substantially optimal detection angle, i.e., a detection angle within an angular range of an optimal angle, where the angular range provides a known uncertainty in the detector measurement, the known uncertainty being within a selected confidence bound.

For example, for a given range of detection angles, and/or parameters for the detector (e.g., optical parameters for the detector optics, etc.) the method and detector of the present application will provide a measurement of any aerosol moment together with a confidence bound for that measurement.

The method of the present application indicates which range of detection angles may provide particularly accurate measurements for a certain type of aerosol, and also, which range of detection angles may provide particularly accurate measurements for a certain aerosol moment (e.g., volume, particulate surface area, etc.) or weighted average of multiple moments. The detector of the present application can be optimized to accurately detect any aerosol and any moment or moment combination, without knowing in advance the specific aerosol to be detected, and without having to recalibrate the detector to the specific aerosol to be measured. The detection angle of the detector can thus be adjusted to create an improved measurement response for a desired confidence bound for an aerosol moment and for an anticipated range of aerosol distribution properties. The anticipated range of aerosol distribution properties may be a broad range, thus only generally characterizing the aerosol to be measured, i.e., without knowledge of the specific substance contained in the aerosol.

Exemplary Implementation of Computational Model

Sensor design and optimization is based on a first-principles optical scattering model.

An exemplary implementation of the model is presented below. While the model is described in the context of aerosol detection and analysis, where a laser source sends incident radiation onto the aerosol distribution, the computational model described herein is equally applicable to detection and analysis of a distribution of aerosols irradiated by a light source of one or more wavelengths, wherein the laser source may be a source other than a laser. The computational model described herein is also equally applicable to detection and analysis of any distribution of particles whose light scattering behavior may be described by the computational model, wherein the distribution of particles receives incident radiation from a laser or other radiation source that emits radiation of one or more wavelengths.

In essence, the model represents the scattering from a single particle, integrated over the particle size distribution (PSD) of the aerosol, and normalized by a particular integrated moment of the PSD. As described above, in its most general form, the model incorporates all aspects of the optical properties of the particulates, the modal properties of the overall aerosol distribution, the attributes of the incident light (including polarization), and the detection geometry. The exemplary implementation described below will be limited to unpolarized light that is scattered by spherical particles. In this case, the model takes the form:

Forward Model:

The scattered power by the ensemble of aerosols at angle $\theta$ (which is an angle between the incident laser light and the direction of detection by the sensor) is given by $$P_{det}(\theta) = NGS(\theta)P_{in},$$

where
N=number concentration $$G = \frac{\lambda^2 L (\Delta\theta)^2}{2\pi^2} = \text{geometrical factor}$$

$$S(\theta) = \int_0^\infty da\, P(a) \left[ \frac{1}{2} |S_1(\theta, a, n, \lambda)|^2 + \frac{1}{2} |S_2(\theta, a, n, \lambda)|^2 \right] = \text{scattering function}$$

$P_{in}$=incident laser power.

Also, $\lambda$=wavelength, n=index of refraction, L=sample volume length, $\Delta\theta$=detector angular subtense, a=particle radius, and P(a)=particle size distribution function.

The polarization dependent Mie scattering functions $S_{1,2}$ used in the calculations were, in an exemplary embodiment, Matlab implementations of functional forms derived by Bohren, C. F., and Huffman, D. in "Absorption and Scattering of Light by Small Particles", John Wiley, New York, 1983, Chapter 4, the entire contents of this publication being hereby incorporated by reference. They convey the dependence of the scattered field on particle composition (refractive index), size and wavelength. The subscripts 1,2 on the Mie scattering functions refer to the direction of polarization, either perpendicular or parallel to the scattering plane. In the exemplary model (unpolarized), the scattered power is an average of the two. The integral over the particle size distribution was computed numerically in Matlab using the adaptive Simpson quadrature routine with the default error tolerance of $10^{-6}$.

The scattered power can be normalized by any integral moment of the particle size distribution. In the exemplary model, normalization by the second and third moments (i.e. surface area and volume, respectively) is illustrated.

Normalization of the Scattered Power by Volume Concentration or Surface Area Concentration:

$$N = \frac{\text{\# of particles}}{\text{sample volume}} = V_{conc} \cdot \frac{1}{\text{avg. volume of single particle}}$$

were $V_{conc} = \frac{\text{total volume of particles}}{\text{sample volume}}$ i.e. $N = V_{conc} \cdot \frac{1}{\frac{4\pi}{3}\langle a^3 \rangle}$ Alternatively, $$N = \frac{\text{\# of particles}}{\text{surface area}} = A_{conc} \cdot \frac{1}{\text{avg. surface area of single particle}}$$

were $A_{conc} = \frac{\text{total surface area of particles}}{\text{sample volume}}$ i.e. $N = A_{conc} \cdot \frac{1}{4\pi\langle a^2 \rangle}$ Therefore, the scattered power normalized by either the volume concentration or surface area concentration:

$$\frac{P_{det}(\theta)}{V_{conc}} = \frac{1}{\frac{4\pi}{3}\langle a^3 \rangle} \cdot GS(\theta)P_{in}$$

$$\frac{P_{det}(\theta)}{A_{conc}} = \frac{1}{4\pi\langle a^2 \rangle} \cdot GS(\theta)P_{in}$$

Normalizing the scattered power in this way is equivalent to normalizing the particle size distribution (PSD) by the corresponding integral moment, as discussed above.

Inversion Procedure for Sensor Design and Optimization

With the normalized expressions for the scattered power, an inversion procedure can be performed for calculating a particular moment of the particle size distribution from the scattered power. In the exemplary model, this is performed for the volume concentration and the surface area concentration.

Inverse Method (i.e. Determination of Volume Concentration or Surface Area Concentration from MPASS Measurements):

Let us define:

MPASS$_V(\theta)$=MPASS volume channel (output in volts)

MPASS$_A(\theta)$=MPASS surface area channel (output in volts)

It should be noted that the MPASS channels output may also be in other units besides volts.

These quantities are the measurement voltages for the volume and surface area channels, respectively. The volume concentration is then given by $$\overline{V_{conc}} = \text{MPASS}_V(\theta_V) \cdot C_{V1} \cdot C_{V2}(\theta_V),$$

where $C_{V1}$ is a system constant, converting from electrical power (for example volts) to optical power (for example watts), and $C_{V2}$ converts from optical power to aerosol concentration.

$C_{V1}$ is determined by direct measurement using a reference aerosol(s). It is fixed once the hardware configuration and moment measurement (in this case, volume) are specified. A useful feature of the overall method described in the present application is the ability to establish the value of constant using any reference aerosol for which any integrated moment quantity has been suitably characterized, and then use the sensor calibrated as such, to measure an aerosol different from the reference aerosol, without recalibrating the sensor to the different aerosol.

$C_{V2}(\theta_V)$, on the other hand, is a conversion factor, which depends on the set of candidate aerosols. It is given by $$C_{V2}(\theta_V) = \frac{1}{M} \cdot \left[ \frac{1}{\left(\frac{P_1(\theta_V)}{V}\right)_{model}} + \frac{1}{\left(\frac{P_2(\theta_V)}{V}\right)_{model}} + \ldots + \frac{1}{\left(\frac{P_M(\theta_V)}{V}\right)_{model}} \right]$$

where $\left(\frac{P_i(\theta_V)}{V}\right)_{model}$ for $i = 1, \ldots$, $M$ = model prediction for $i^{th}$ aerosol distribution In other words, M is the number of aerosol distributions, and $(P_i(\theta_V)/V)_{model}$ is the scattered power normalized by volume for one distribution (distribution i, where i is between 1 and M).

As an example, one such aerosol distribution i may be a Gaussian distribution characterized by a certain count median diameter of aerosol size distribution and geometric standard deviation of aerosol size distribution, another aerosol distribution j may be another Gaussian distribution characterized by another set of count median diameter of aerosol size distribution and geometric standard deviation of aerosol size distribution, etc. There are M aerosol distributions defined by M pairs of (count median diameter—CMD, geometric standard deviation—$\sigma_g$) of aerosol size distribution, the pairs being obtained by iterating through a range R1 of count median diameter and a range R2 of geometric standard deviation (i.e., each (count median diameter, geometric standard deviation) pair is obtained by selecting a value of count median diameter from the range R1 and a value for the geometric standard deviation from the range R2). Ranges R1 and R2 represent information about the aerosol. Larger ranges R1 and R2 correspond to less information about the aerosol, while smaller ranges correspond to more information about the aerosol.

$C_{V2}(\theta_V)$ converts from optical power to volume concentration (in this case), and is averaged over the candidate aerosols.

Likewise, the surface area concentration is given by $$\overline{A_{conc}} = \text{MPASS}_A(\theta_A) \cdot C_{A1} \cdot C_{A2}(\theta_A)$$

where
$C_{A1}$=system constant (in watts/volt)

$$C_{A2}(\theta_A) = \frac{1}{M} \cdot \left[ \frac{1}{\left(\frac{P_1(\theta_A)}{A}\right)_{model}} + \frac{1}{\left(\frac{P_2(\theta_A)}{A}\right)_{model}} + \ldots + \frac{1}{\left(\frac{P_M(\theta_A)}{A}\right)_{model}} \right]$$

and $$\left(\frac{P_i(\theta_A)}{A}\right)_{model} \text{ for } i = 1, \ldots,$$

$M$ = model prediction for $i^{th}$ aerosol distribution

The procedure for determining the volume concentration principally involves determination of $C_{V2}$. To begin, one must determine the optimal angle, $\theta_V$, for the measurement. This is done by utilizing any and all a priori information about the possible aerosol distributions. Then, one calculates the relative error in the calculation of $C_{V2}(\theta_V)$ as a function of $\theta_V$. This quantity is defined as relative error (volume) =

$$\frac{\text{standard deviation}\left[\frac{1}{\left(\frac{P_i(\theta_V)}{V}\right)_{model}}\right]}{\text{mean}\left[\frac{1}{\left(\frac{P_i(\theta_V)}{V}\right)_{model}}\right]} = \frac{\Delta\left[\frac{1}{\left(\frac{P_i(\theta_V)}{V}\right)_{model}}\right]}{C_{V2}(\theta_V)}$$

The optimal value of $\theta_V$ is the one for which the relative error is a minimum. Minimizing the relative error in this way ensures that the conversion from optical power to volume concentration is as independent of the modal parameters of the aerosol distribution as possible. The procedure for the surface area is the same. Clearly, the better one is able to constrain the modal parameters of the aerosol distributions to which the MPASS is possibly exposed (the smaller M), the better the estimates. For example, for a single distribution, the error is zero. In the exemplary discussion of ranges R1 and R2 above, a single distribution would correspond to a range R1 which is collapsed to just one value, and a range R2 which is also collapsed to just one value, that is, the count median diameter and geometric standard deviation for the aerosol distribution are fully known, which is the case if the aerosol to be measured is a known type of particles.

As explained above, $C_1$ (e.g., $C_{V1}$ when the moment is volume, $C_{A1}$ when the moment is surface area, etc.) is a system calibration constant, and does not depend on the aerosol to be measured. $C_2$ (e.g., $C_{V2}(\theta_V)$ when the measured moment is aerosol volume, $C_{A2}(\theta_A)$ when the measured moment is aerosol surface area) depends on the set of candidate aerosols to be measured, and converts from optical power to value of aerosol moment.

Using the measurement of volume (the $3^{rd}$ integrated moment) as an exemplary implementation, the interplay between sensor calibration and measurement of aerosols is explained in more detail below. The details presented below apply to the measurement of any moment quantity.

Figure 10A:
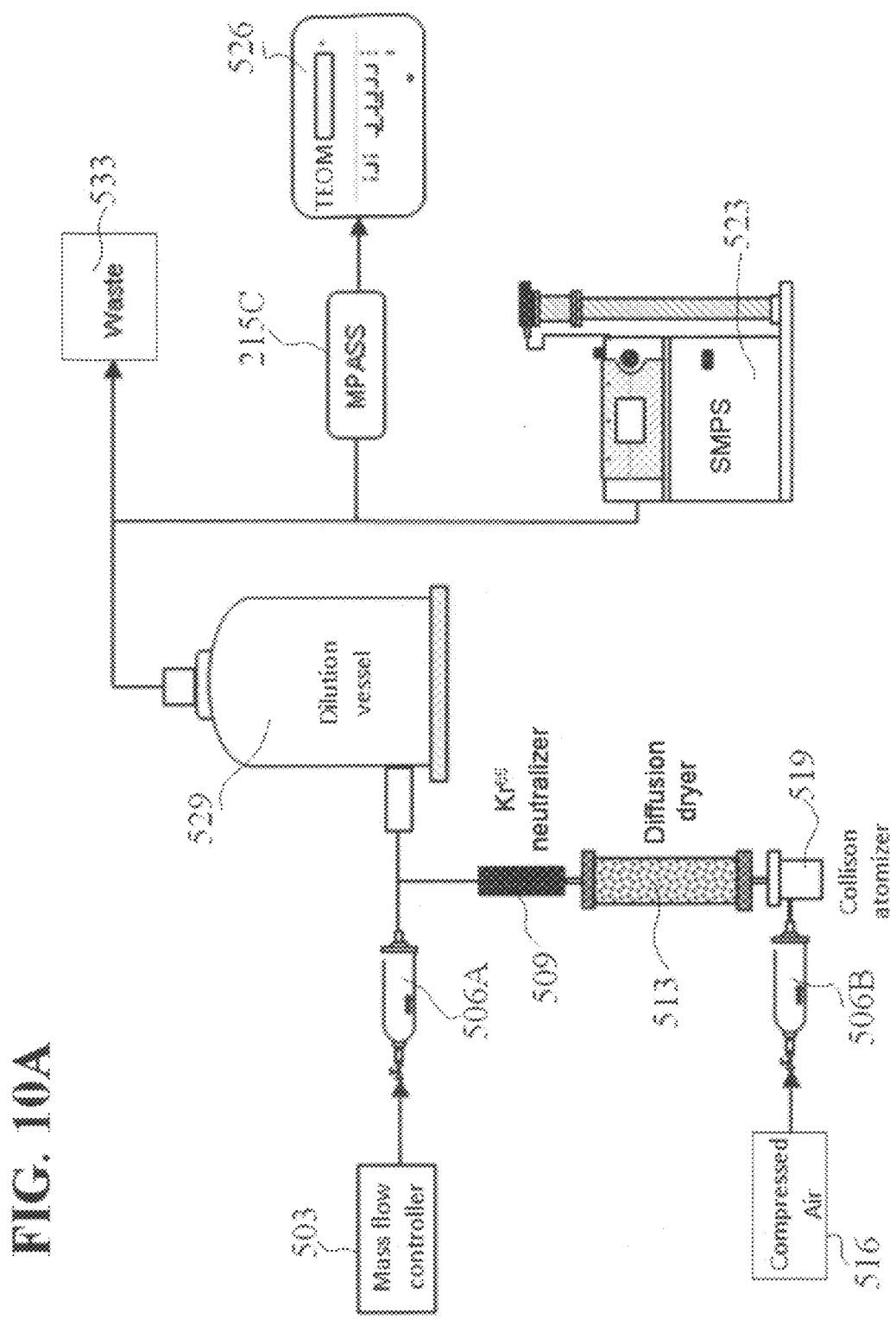
Figure 10B:
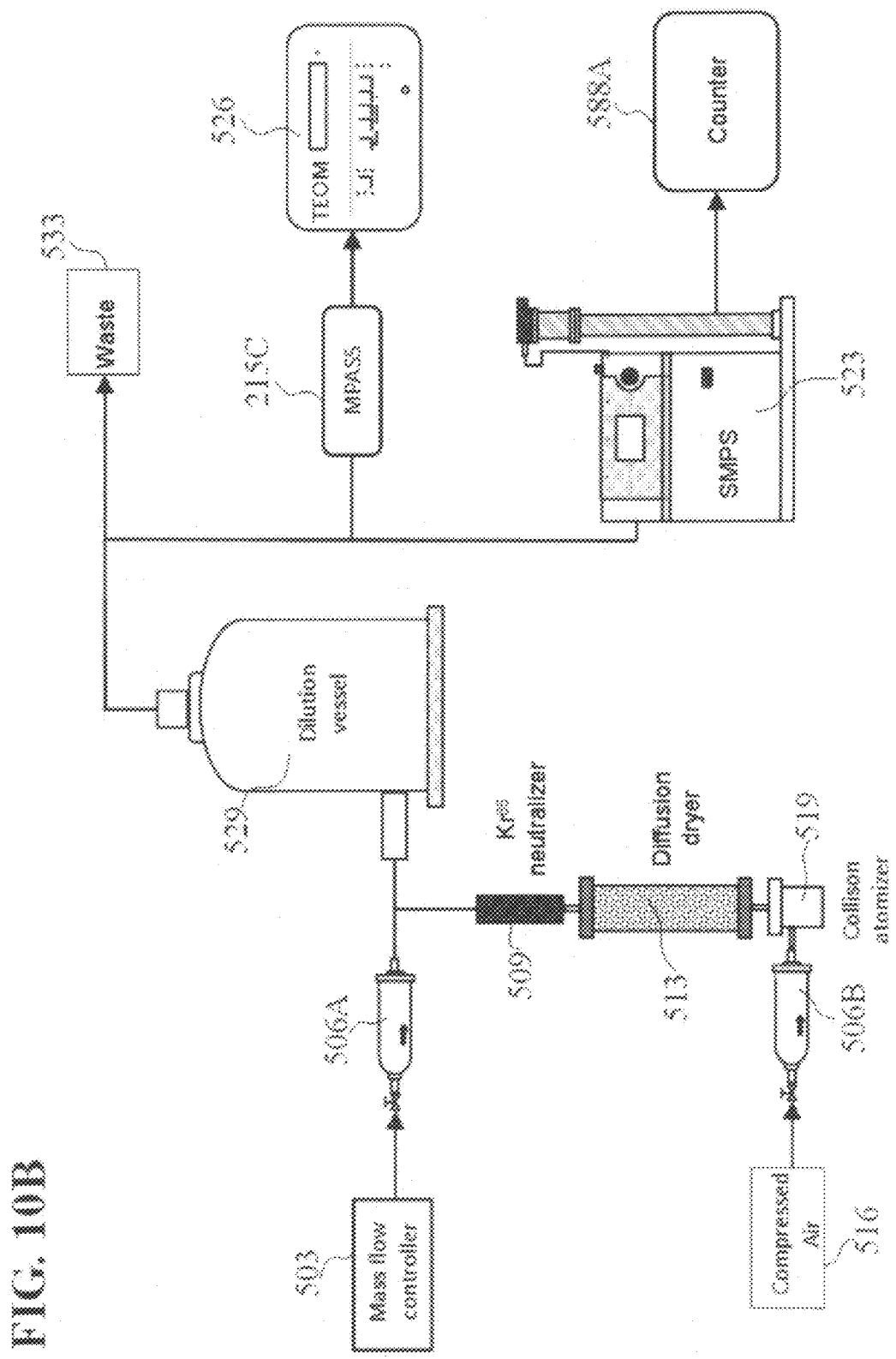
Figure 10C:
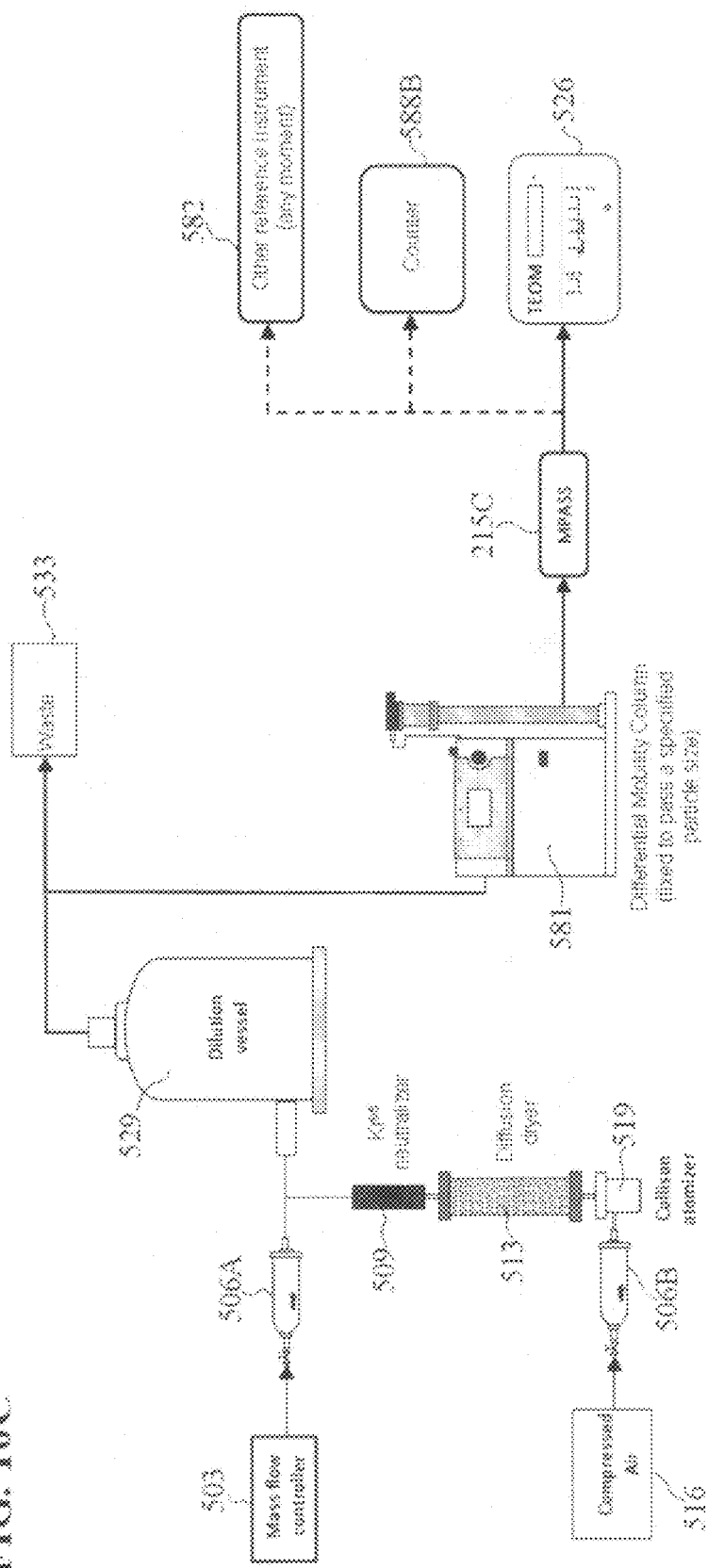

The constant $C_1$ characterizes the optical collection and voltage conversion efficiency of each detector. It yields the optical power [in watts] received for a given measured signal (detector voltage). $C_1$ is an intrinsic property of the hardware. Because each detector (as well as the optics that precede it and the electronic preamplifier that follows it) differs, each is individually calibrated. This calibration is done using a reference aerosol. In the method presented in the present application, any reference aerosol can be used for this purpose, as long as it is well characterized. Once $C_1$ is determined for each detector, the hardware itself is completely characterized. If a given detector system (see, for example, the system shown in FIG. 7) has, for example, five detectors at fixed angles, all five detectors can be calibrated simultaneously by exposure to the same reference aerosol. Constant(s) $C_1$ can then be saved in each detector's processor, whereby the saved data for a detector includes calibration constant(s) $C_1$ which will be later used to measure various moments and combinations of moments with that detector. If a given detector system has, on the other hand, a moveable detector (i.e., one that can be moved to different detection angles $\theta$), the detector can be calibrated by exposure to the reference aerosol. The detector may be calibrated for various detection angles. As explained above, $C_1$ is a property of the hardware only, which incorporates, for example, the strength of the laser and its focusing, the collection efficiency of a given detector and any losses in its optics, as well as the electrical conversion of the preamplifier associated with this detector. These intrinsic characteristics of the hardware may or may not vary as the angular placement of the detector changes, and the calibration constant(s) $C_1$ may be determined accordingly. To perform the calibration, any reference instrument may be used, regardless of the arbitrary integrated moment that reference instrument measures. If, for example, a monodisperse reference aerosol is used for calibration (see FIG. 10C) to measure the $0^{th}$ moment or other moment, calibration constant $C_1$ may be determined by decoupling the properties of the monodisperse reference aerosol from the results of the reference measurement, since the monodisperse reference aerosol is well characterized, i.e., its particle size, refractive index, count, surface area, volume, etc., are known. If a polydisperse reference aerosol is used for calibration (see FIG. 10B), the distribution parameters of the polydisperse reference aerosol are used to decouple the properties of the polydisperse reference aerosol from the results of the reference measurement, and obtain constant $C_1$.

Thus, any reference aerosol (polydisperse or monodisperse, for example) can be used for calibration, as long as it is well characterized, i.e., as long as its properties are known, since the calibration experimentally determines the sensor responsivity, and $C_1$ is obtained after decoupling $C_2$ which is known for a well characterized reference aerosol.

Constant(s) $C_1$ (e.g., $C_{V1}$, $C_{A1}$, etc.) then be saved in the detector's processor, for later use to measure various aerosols with the detector, at various angles.

The responsivity of the sensor describes the end-to-end relationship between the aerosol being measured, and the signal (in volts) that is produced. Again, using the $3^{rd}$ moment as an example, the responsivity provides the following result: "If I observe a signal output of "Y" volts, then my sensor was exposed to an aerosol with a volume concentration of "X" $\mu m^3/m^3$." The responsivity is given by the product of $C_1 \times C_2$.

The novel and advantageous feature of the method and detector of the present application is the separation of $C_1$ and $C_2$. $C_1$ is obtained by calibration, and is a function of the hardware only. $C_2$ is predicted by the underlying analytical model presented herein. This provides extensibility, i.e., ability to accurately measure various aerosols with the detector without recalibrating the detector to the various aerosols. This extensibility of the detector is unique relative to the present state-of-the-art.

Consider the following example. A sensor has been calibrated using aerosol "A". We now wish to know how the responsivity will change when the sensor is exposed to aerosol "B". Under the prior art, the only way to determine this is to re calibrate the sensor using aerosol "B". In contrast, with the development of the present application, we can predict on-the-fly (with no need for additional calibration) how this sensor will respond to the aerosol "B". All that may need to be specified are its modal parameters and refractive index. If these parameters are not known exactly, but are known to lie within some range(s) (i.e., we have only imperfect information about aerosol "B" that places its properties within some broad ranges, for example), the uncertainty in the resulting measurement of "B" with the sensor can be bounded.

Figure 6A:
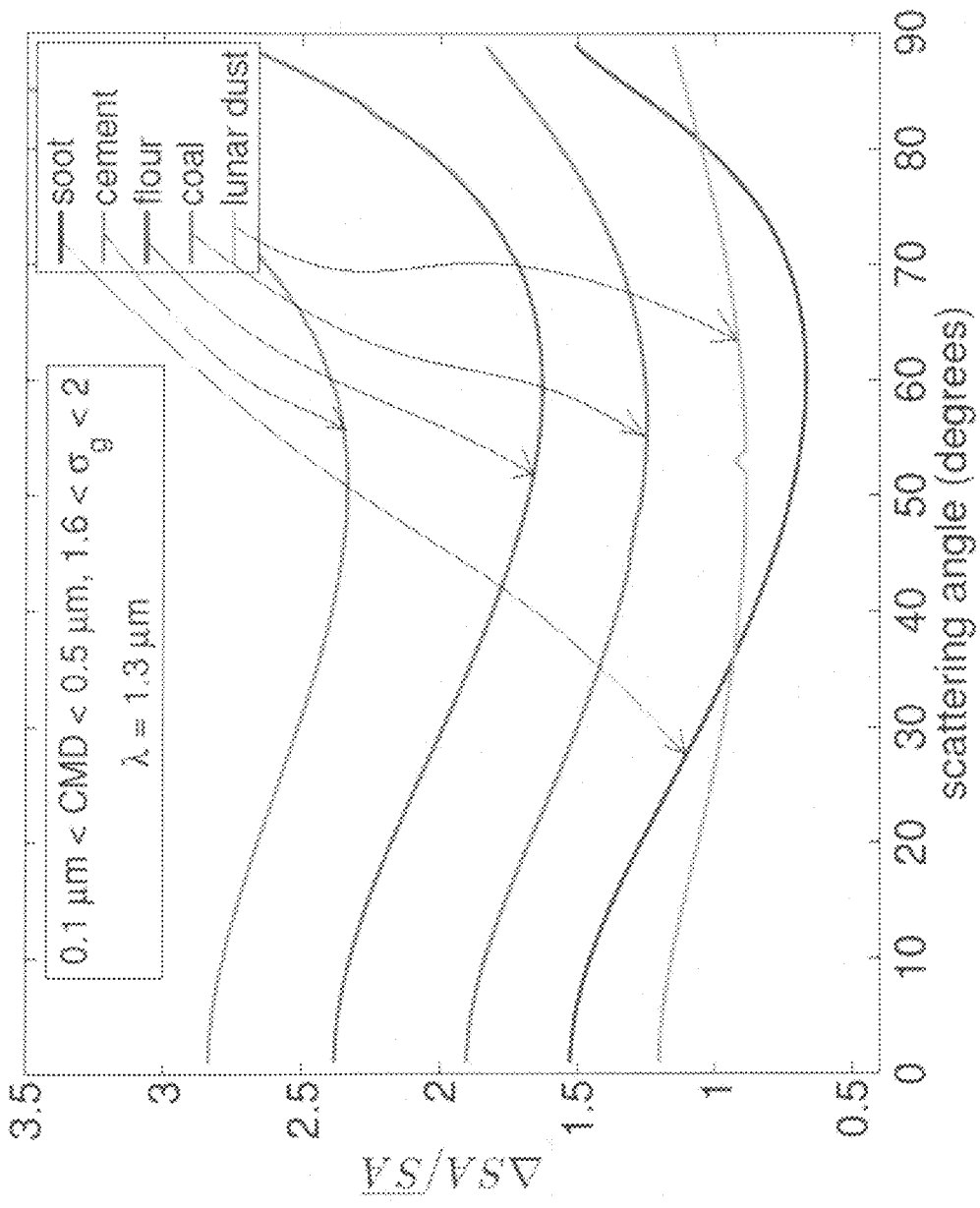
Figure 6B:
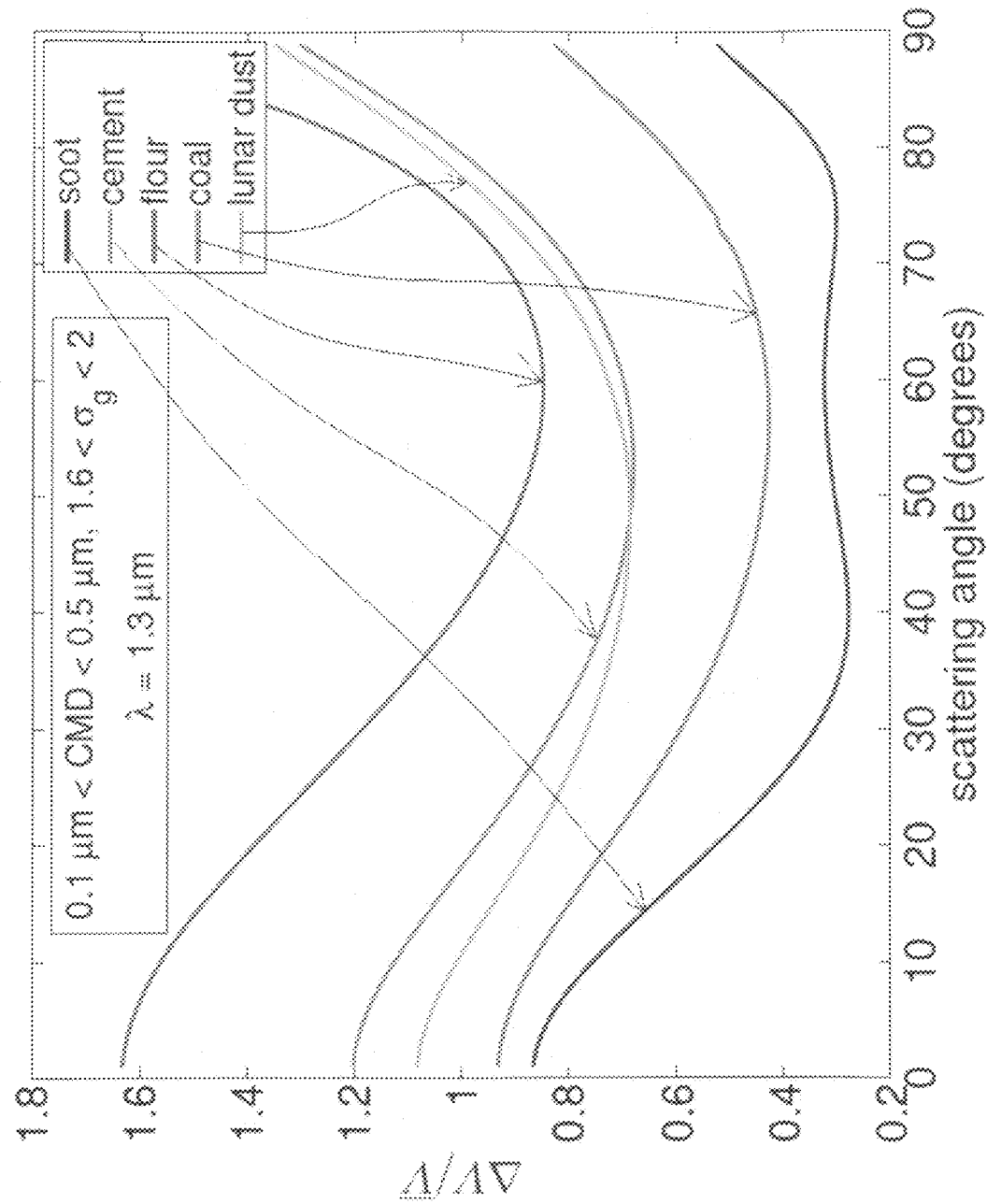
Figure 6C:
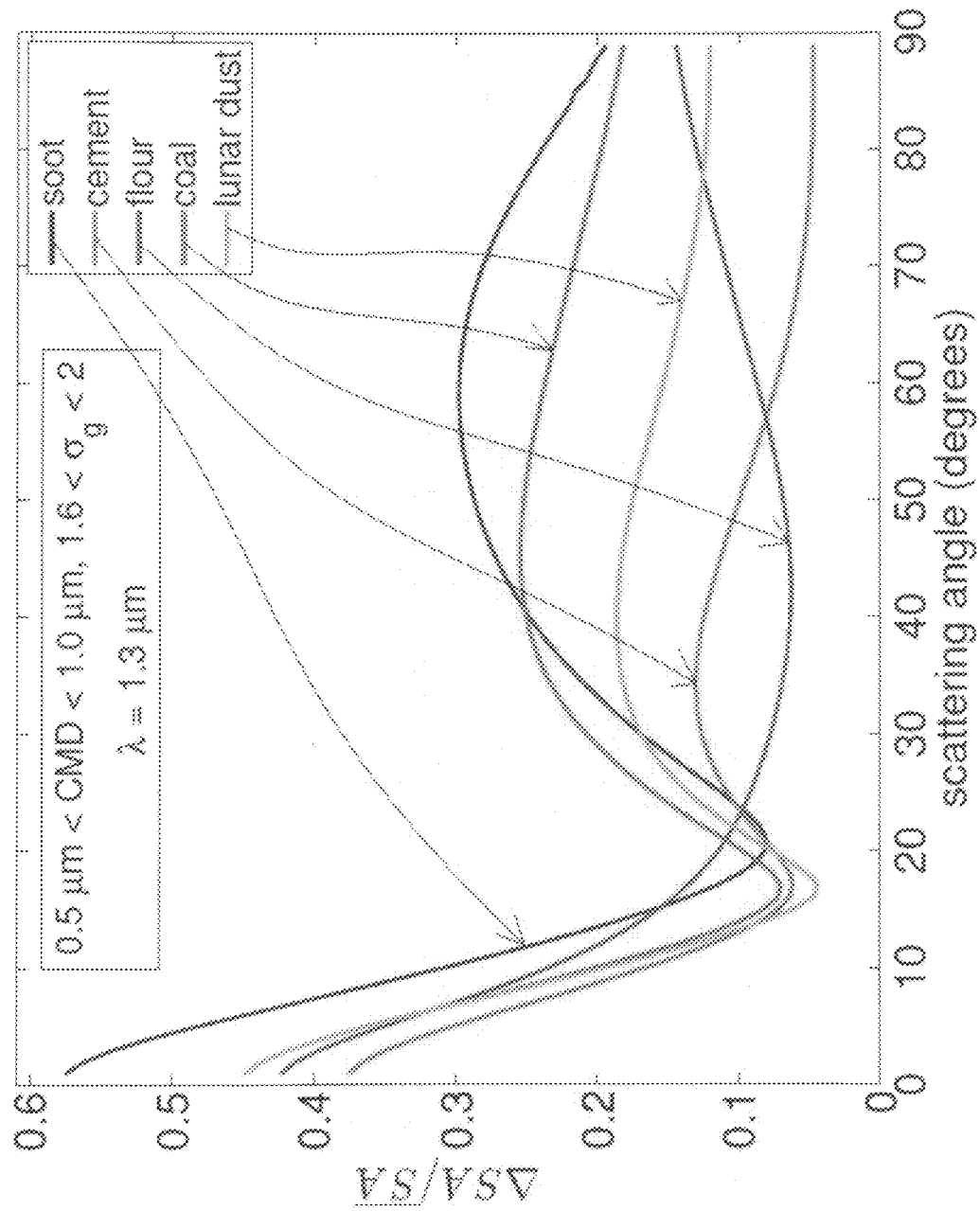
Figure 6D:
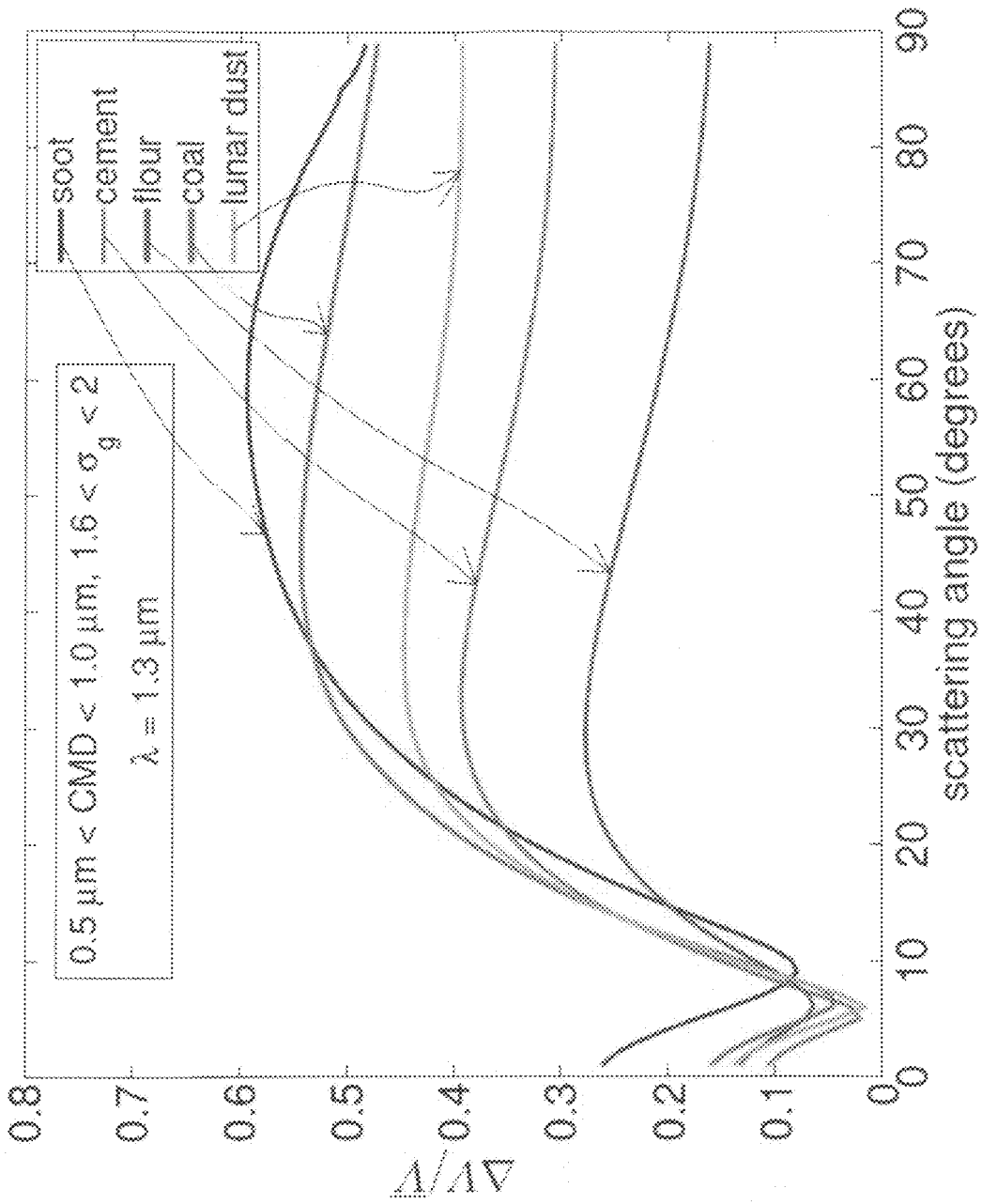
Figure 6E:
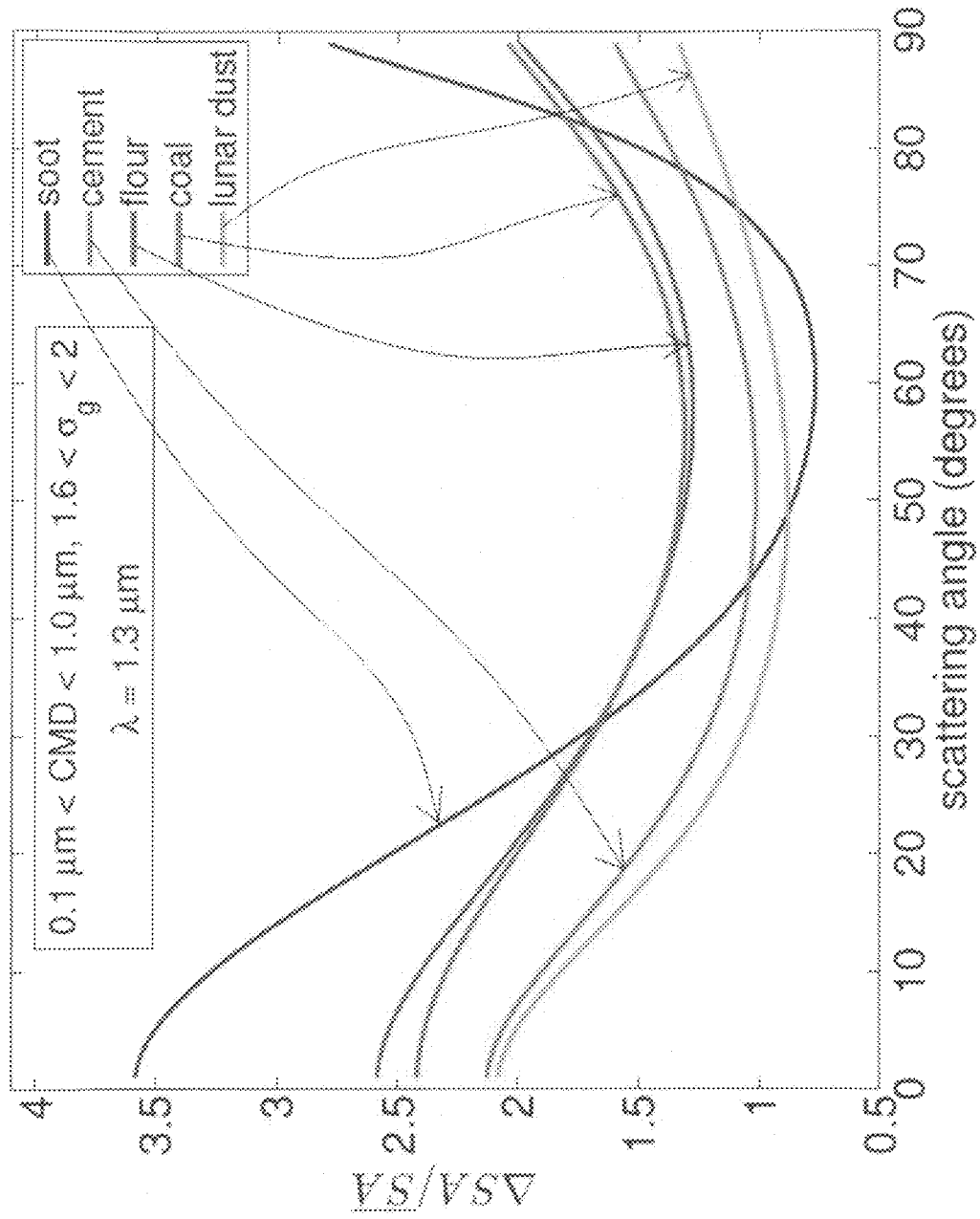
Figure 6F:
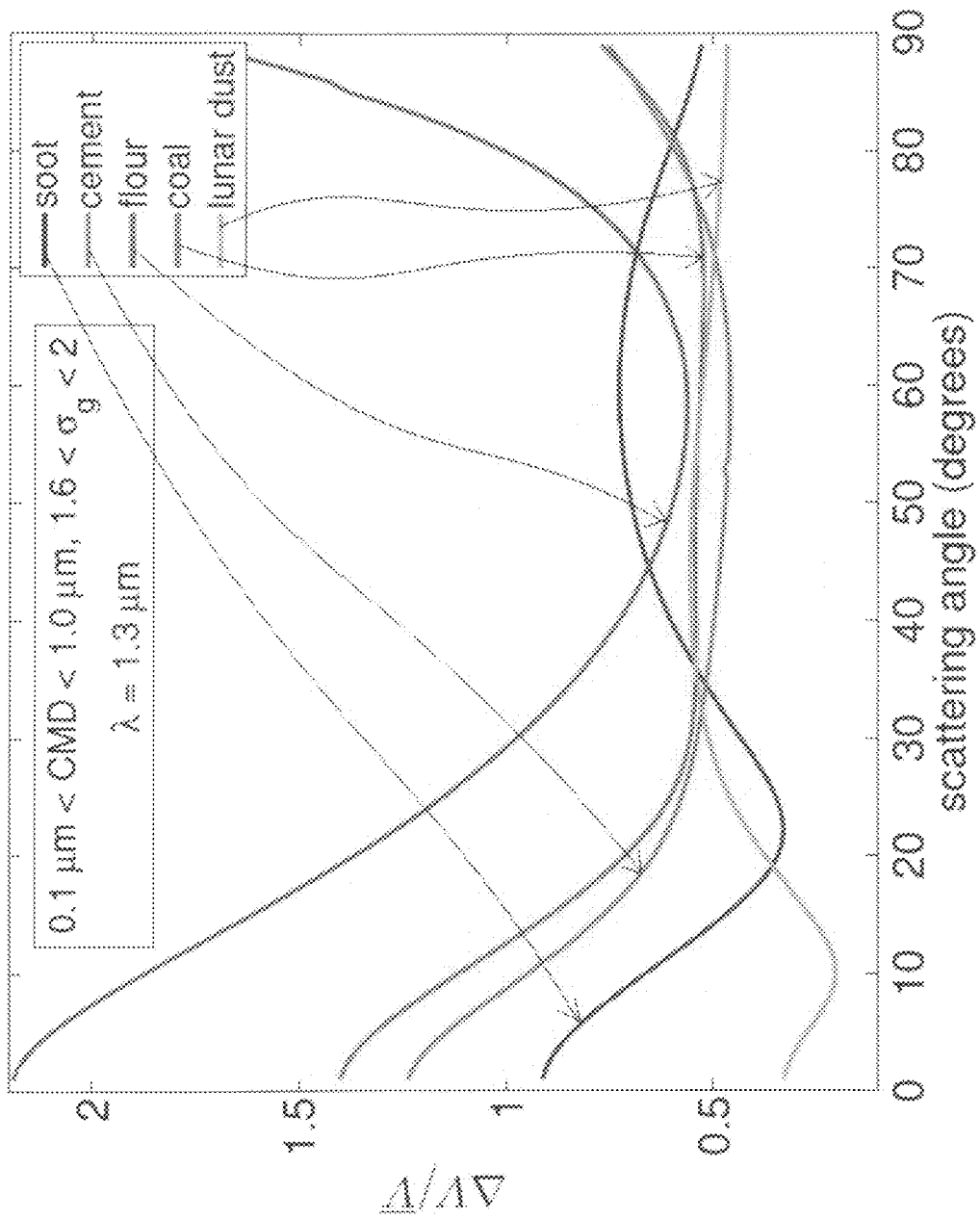
Figure 6G:
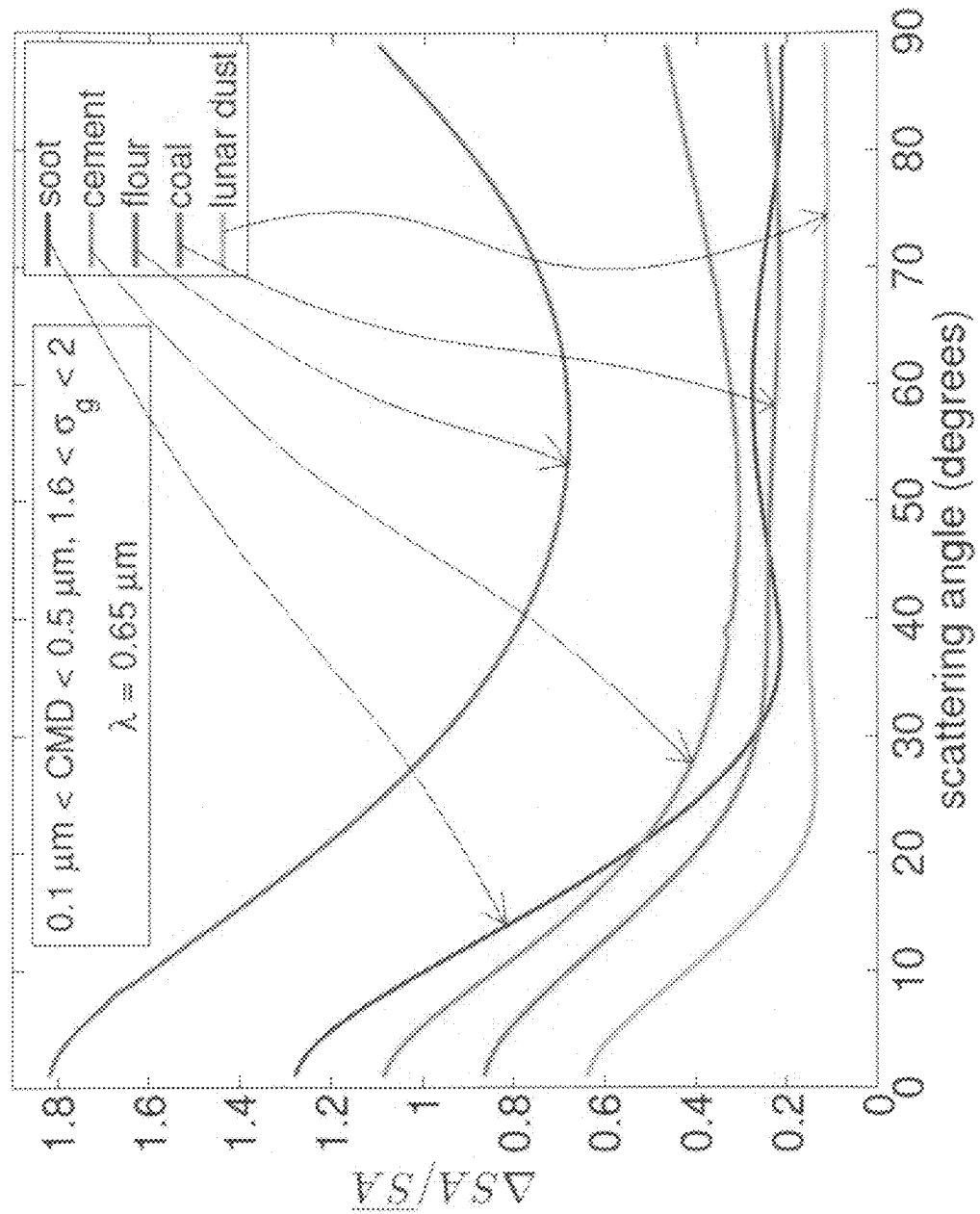
Figure 6H:
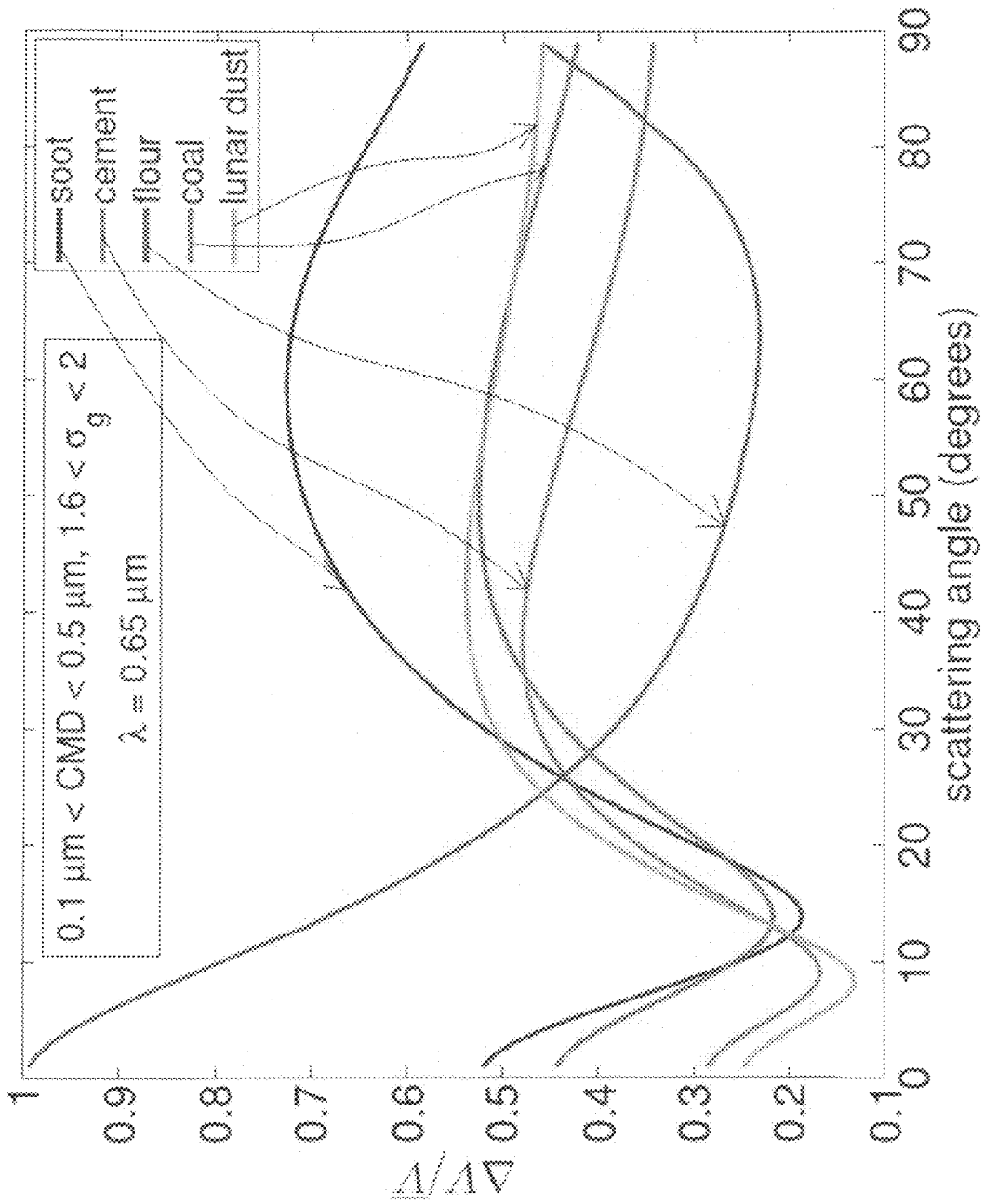
Figure 6I:
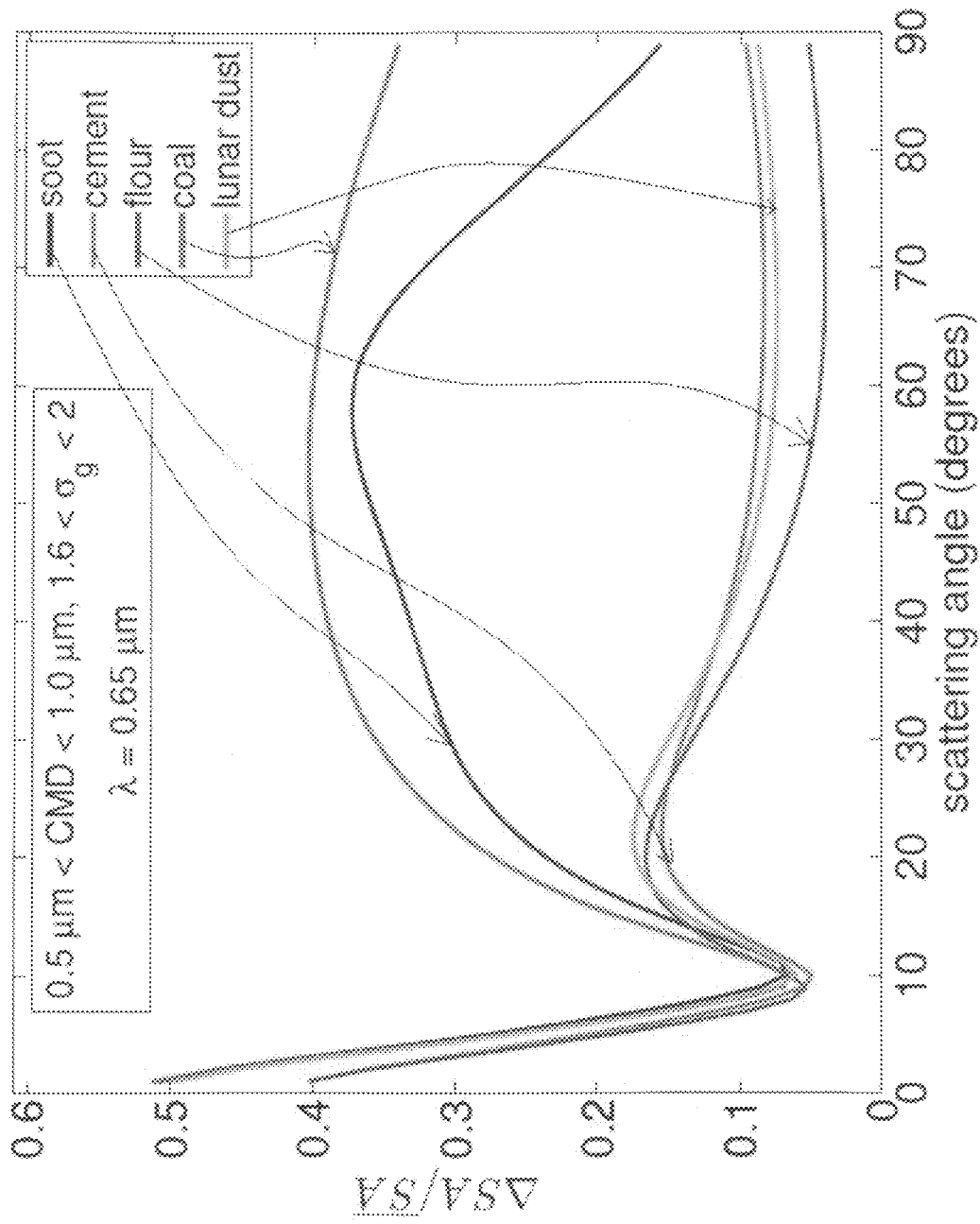
Figure 6J:
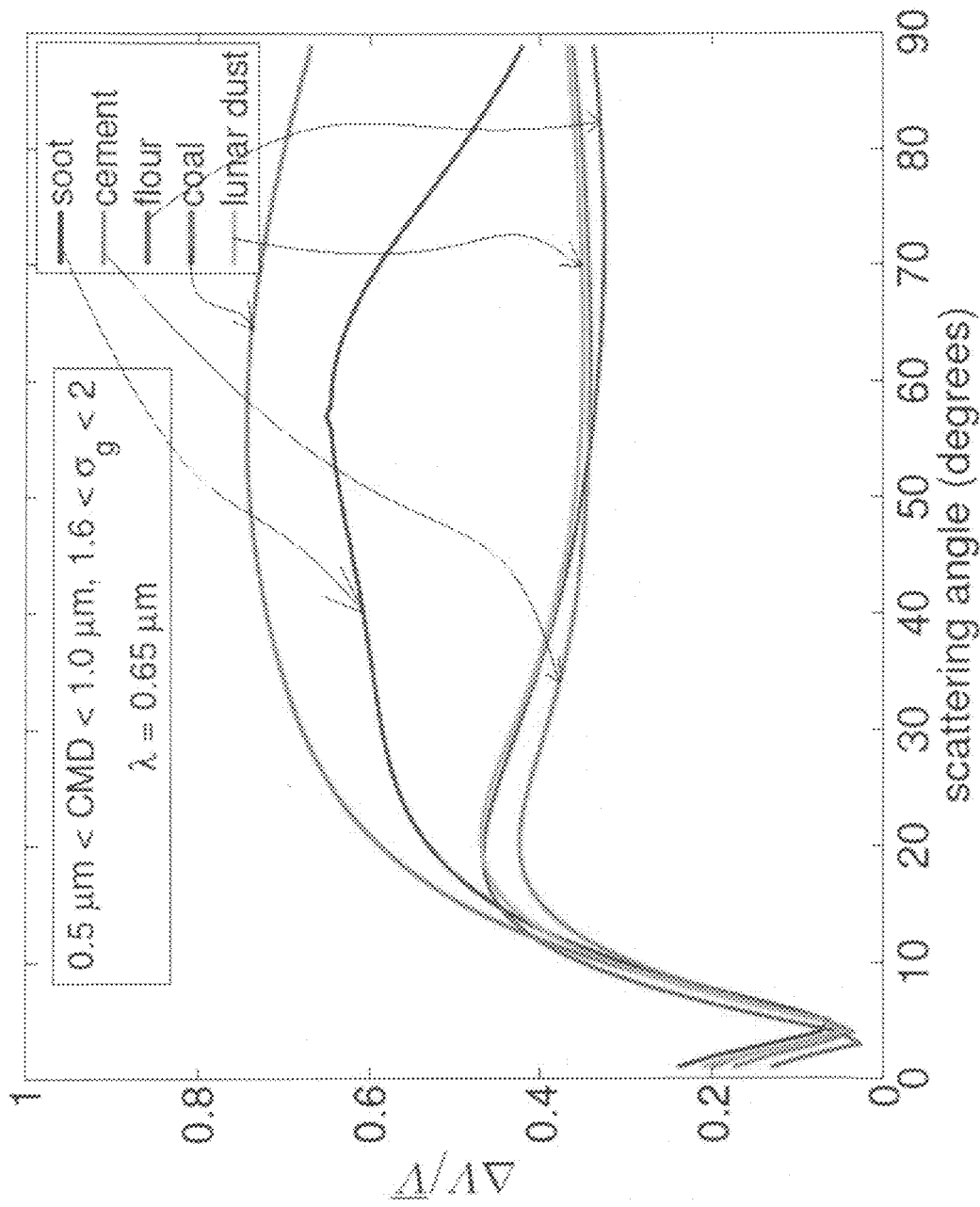
Figure 6K:
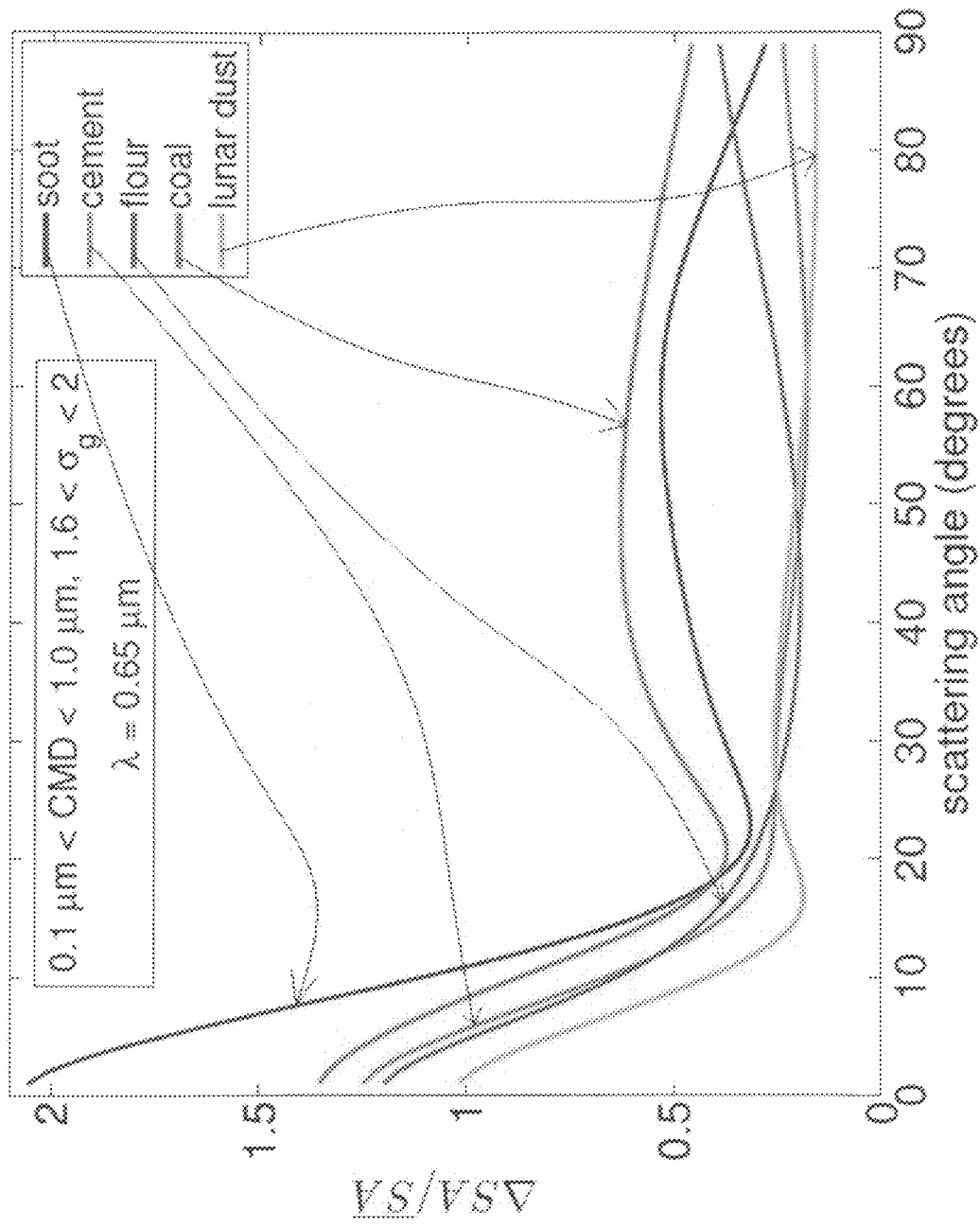
Figure 6M:
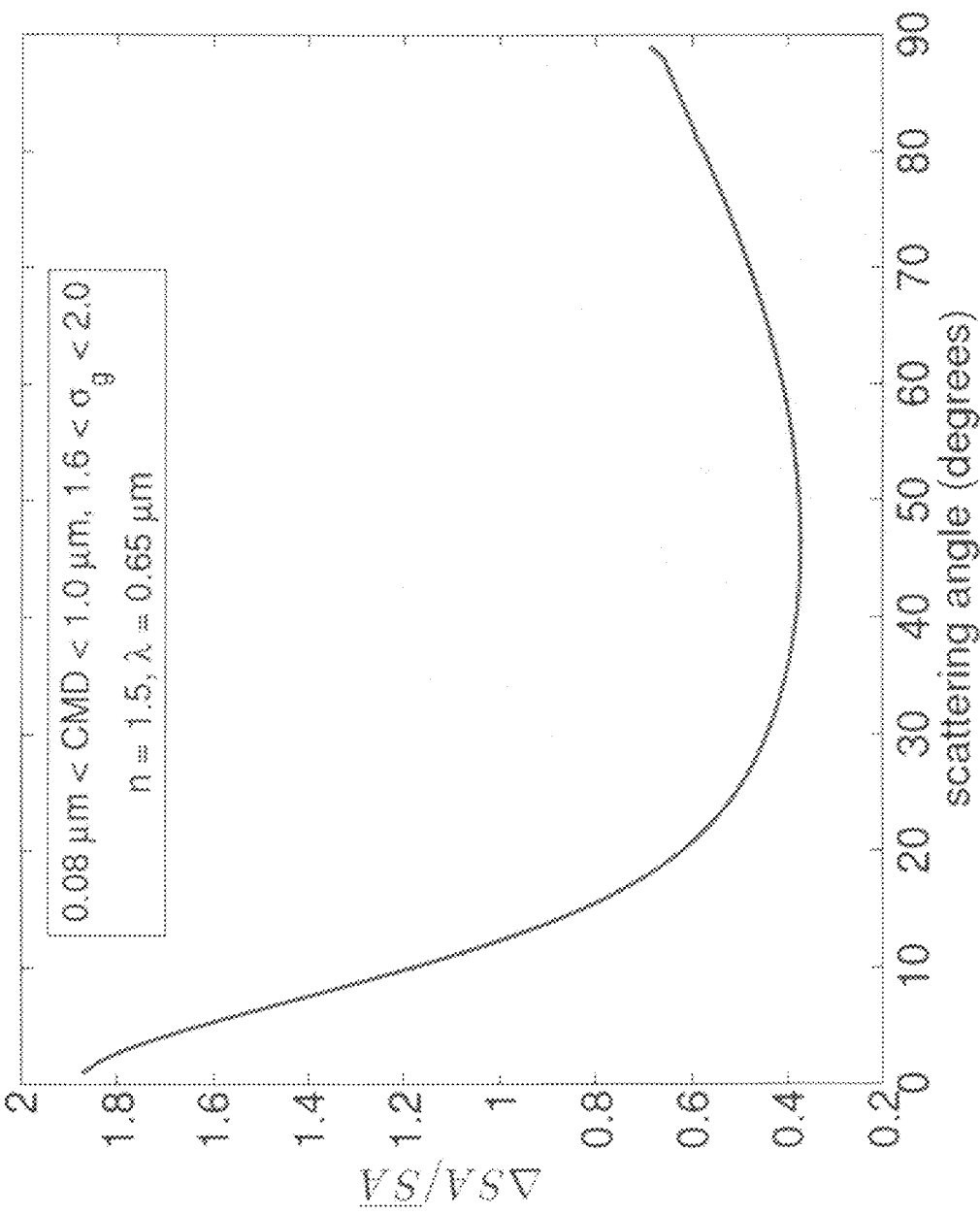
Figure 6N:
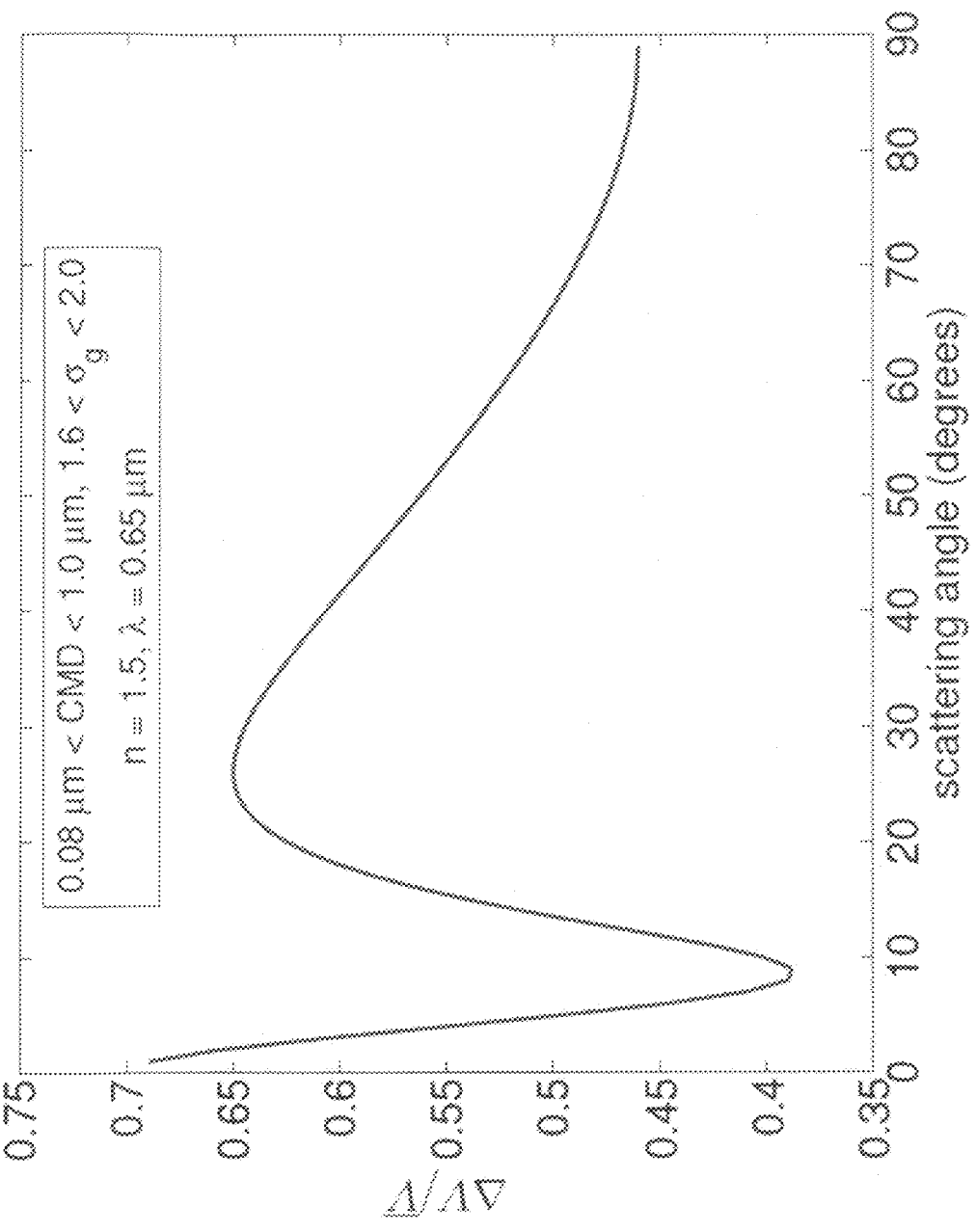
Figure 60:
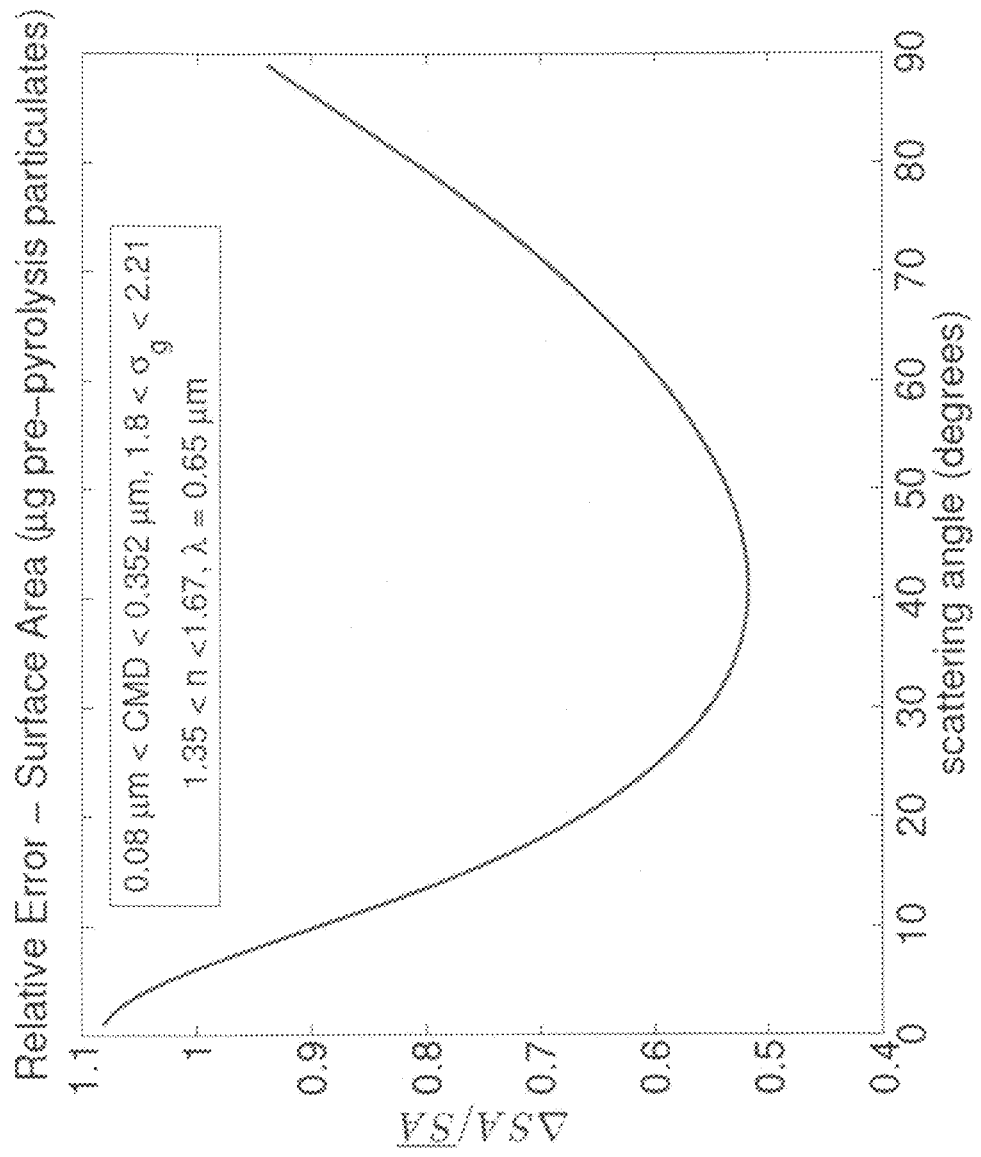
Figure 6P:
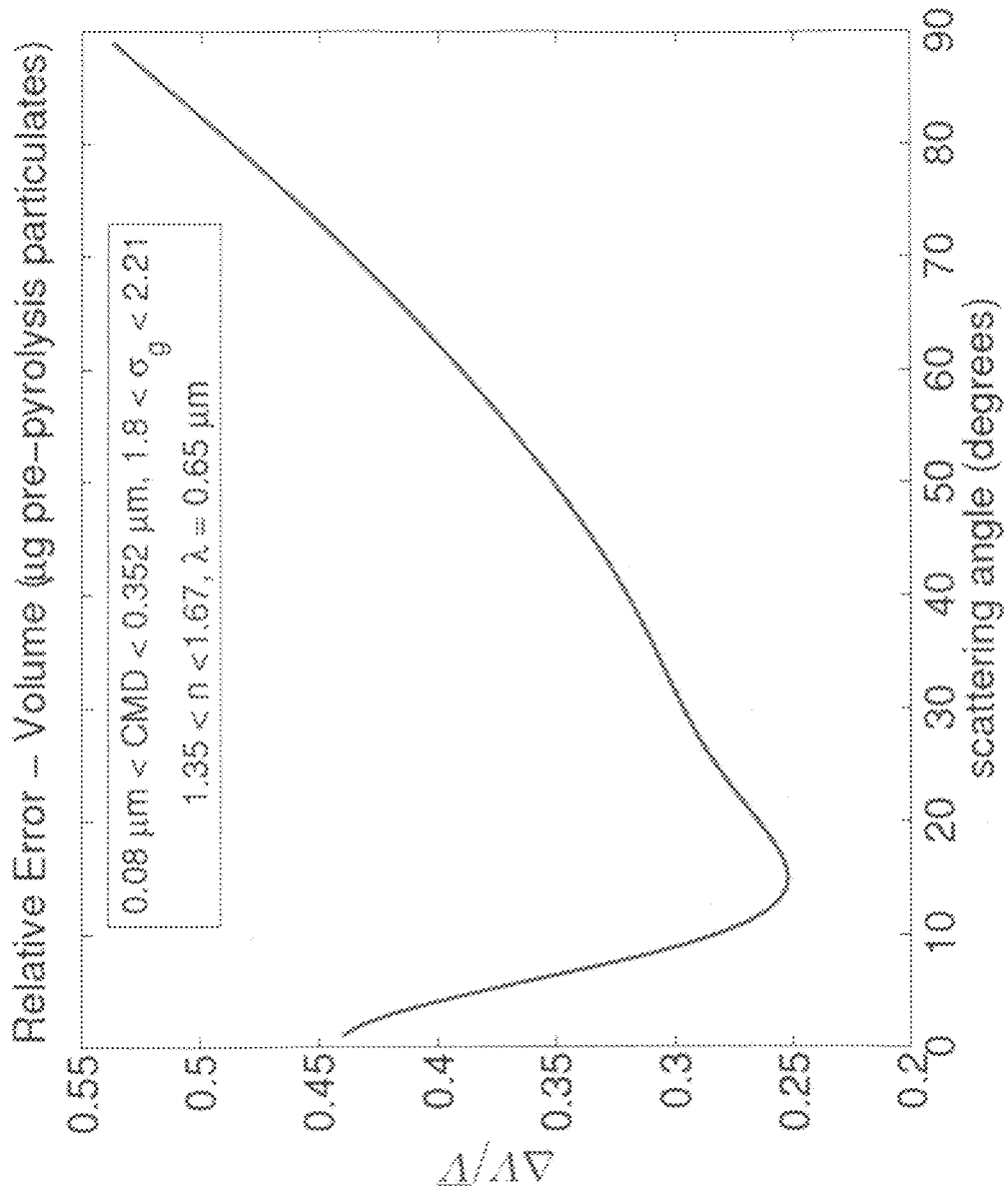
Figure 6Q:
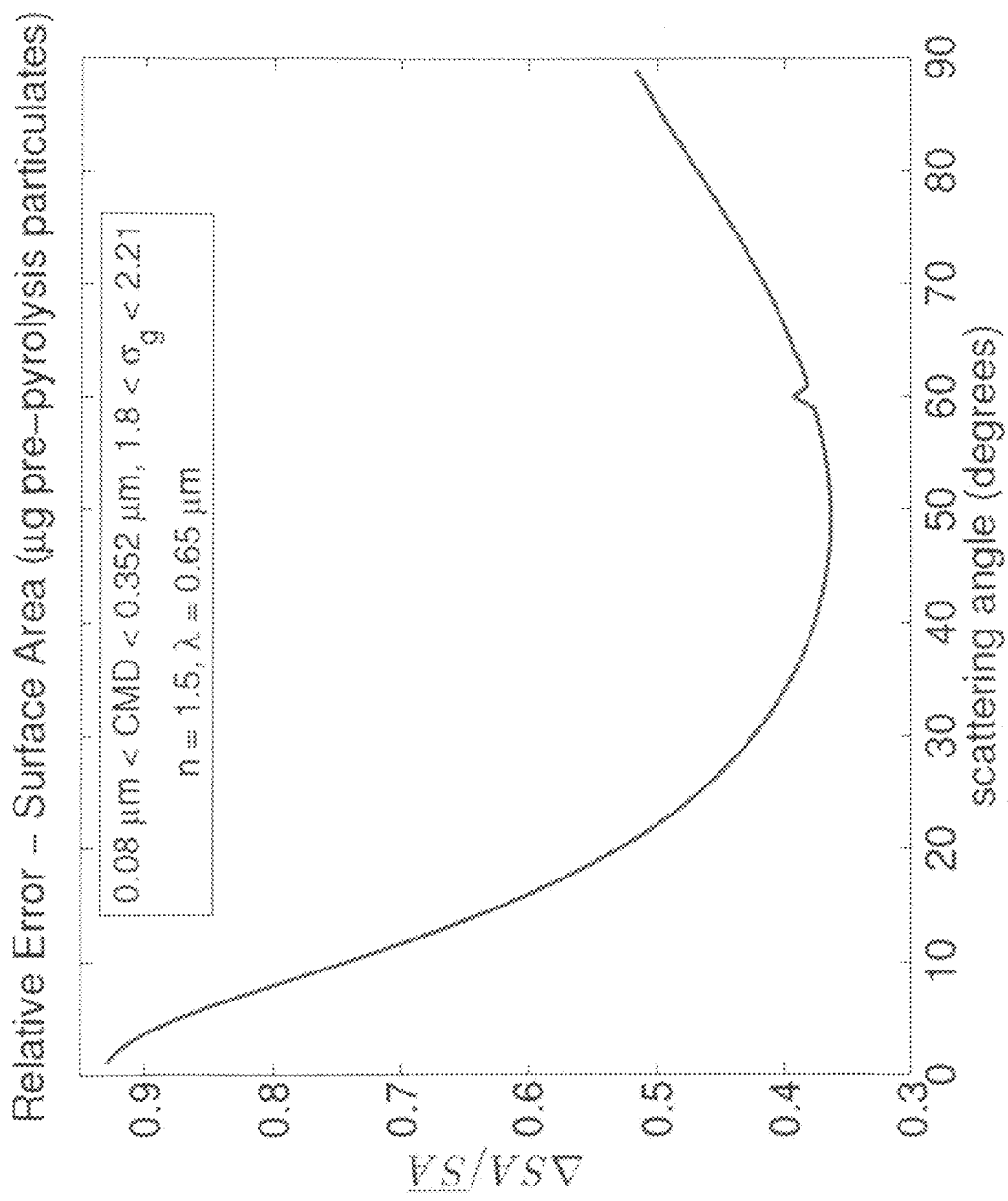
Figure 6R:
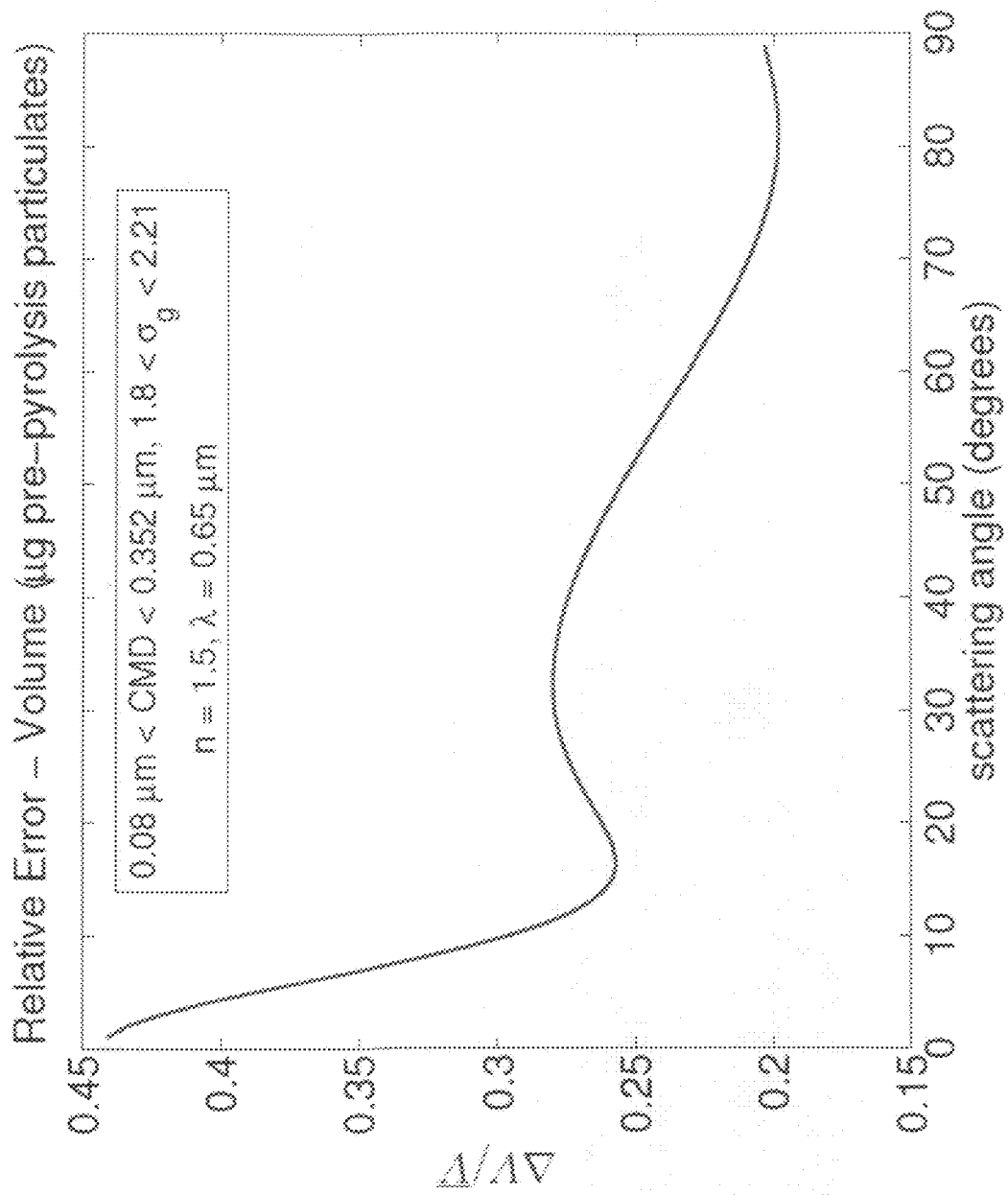

FIGS. 6A-6R present examples of the determination of the optimal measurement angles for volume and surface area. For an exemplary prescribed a priori distribution information, the modal parameter ranges were uniformly sampled for a total of M=100 combinations of CMD and $\sigma_g$.

As indicated above, the computational model provides both the mechanism for determining the optimal detector(s) for a the measurement of a particular integrated moment of the aerosol, as well as the normalization constant, $C_{V2}(\theta_V)$ in the case of volume, or $C_{A2}(\theta_A)$ in the case of surface area, for ensuring the minimum uncertainty in its determination.

Sensor Development

The previously described computational model has been used to develop and demonstrate working sensor prototypes. The method is generalized, and can be used to design and optimize sensors and instruments of arbitrary size and complexity. In an exemplary embodiment, miniature sensors were developed. Such miniature sensors may be, for example, personal monitors and field-deployable embedded applications. Such applications seek to minimize sensor mass, volume, power consumption, cost, etc., and maximize ruggedness, autonomy of operation, operational lifetime, etc., so as to enable deployment of the sensor in harsh or confined field applications, and as distributed sensor networks or as an integrated microsensor package and allow for numerous previously inaccessible applications.

Since Mie scattering is an elastic process (the scattered light is the same wavelength as the incident light), a significant challenge in designing a compact sensor is the management of stray light. Background flare, reflections, or scattering decrease both the sensitivity and dynamic range of the sensor.

In an exemplary embodiment, a monochromatic source for illumination is used, which may be useful because the physical properties (e.g. refractive index) of the particles are wavelength-dependent. In one exemplary embodiment, the monochromatic source for illumination is a laser. Laser sources can also be focused precisely, wherein the resulting quality of focus significantly reduces stray light in the system.

For optimizing size, power consumption, cost, ruggedness, etc., semiconductor diode lasers may be used, in an exemplary embodiment. The downside of semiconductor diode lasers is their poor spatial beam quality, i.e. they focus poorly. This situation is remediated by launching or coupling the laser into a single-mode optical fiber. The beam emerging from a single-mode fiber is spatially pure (approaching perfect), and can therefore be focused with exceptional precision. A minimum length of fiber is required to achieve this beam quality, and this length is contained within the compact enclosure desired for the complete sensor package.

The placement and angular specification of detectors may be optimized on the basis of the first-principles computational model described above, which optimizes the integrated moment responses for a predetermined range of particle and distribution properties. The suppression of stray light is afforded by the use of precision focusing of the incident beam. The quality of focus is achieved via modal conditioning of the input beam. In one embodiment, this is accomplished by coupling the incident light through a suitable length of single-mode optical fiber, as described above. Stray light is further suppressed through the use of matched spatial apertures preceding the detectors (i.e. confocal detection). In this embodiment, these apertures are physically realized in the form of the entrance facet of optical receiving fibers. The detectors are recessed from the sample volume in suitable cavities. When operated in an active sample acquisition mode, the resulting streamlines prevent the particles from contaminating any optical surfaces.

The placement of the detector, or multiple detectors, is optimized by the computational model. In an exemplary embodiment, a typical range encountered in practice for aerosol distributions and particle properties were used. The resulting two detectors in this exemplary embodiment were designed to minimize the resulting uncertainty in the measurement of total mass (the $3^{rd}$ integrated moment) and total surface area (the $2^{nd}$ integrated moment). The former moment remains as the predominant standard for respiratory exposure and early warning fire detection, whereas the latter moment is rapidly superseding mass insofar as human health effects. A third quantity is also obtained, the Sauter Diameter, which is the ratio of the $3^{rd}$ to $2^{nd}$ moments.

In this exemplary embodiment, these apertures are physically embodied as the entrance face of an optical fiber. The appropriate choice of fiber thereby specifies the lateral dimensions of the optical sample volume and the F-number (or Numerical Aperture (NA)) of the collection optics.

The use of optical fibers also provides flexibility in the physical location of the detectors themselves, further facilitating the resulting compactness and ruggedness of the total package. This feature is also valuable in the placement of cooled detectors, should they be utilized.

The transmitting and receiving optics are located around a cavity, through which the aerosol sample passes. The aerosol may be actively sampled (i.e. using a pump), or can enter the cavity passively. The optics themselves are located behind secondary cavities. In the case of active sampling, these cavities are designed such that the resulting velocity streamlines prevent the particles from reaching the optical surfaces. Specifically, when operated in this fashion, the device only needs to be cleaned infrequently.

The sensor also includes an embedded processor/controller. This device enables the laser controller, reads the detector signals, performs algebraic manipulations to subtract residual background, and scale the detector outputs relative to predetermined calibration constants (i.e. to read in true units of mass and surface area). It also formats the data for serial and/or parallel communication.

The sensor may be equipped with a wireless transmitter to allow remote data transfer and commanding.

Figure 3:
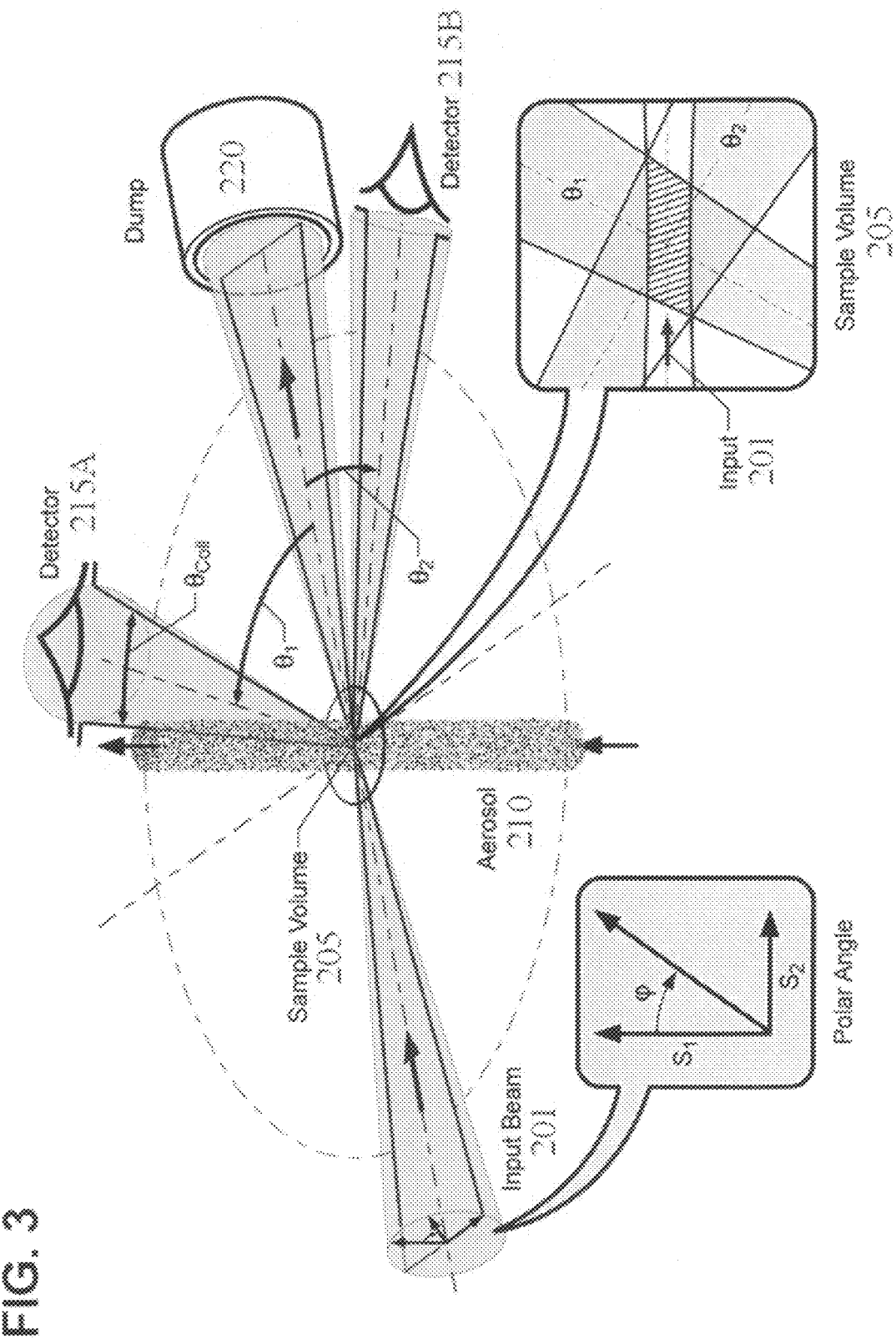

A schematic diagram of an exemplary MPASS sensor and the optical geometry used in the model is shown in FIG. 3. One or more detectors 215A, 215B are oriented in the horizontal plane at angles $\theta_i$ relative to the optical axis. Alternatively or additionally, a detector 215A may be sequentially oriented in the horizontal plane at multiple angles $\theta_i$ relative to the optical axis. For the present purposes, the particles in an aerosol 210 are assumed to be spherical. However, any particle shape can be analyzed by the detector of the present invention, using the disclosed computational model.

As will be described below, the model can be used to optimize the values of $\theta_i$ to achieve the desired sensor performance. The right-hand inset in FIG. 3 shows the spatial relationship of the input beam 201 and the detection volumes 205. The detection volumes 205 are purposefully chosen to be larger than focal volume of the input beam, providing tolerance in the resulting optical alignment. This allows the sensor 215 to be fabricated using relatively modest machining tolerances, and eliminates drift due to mechanical shock or changes in temperature. The collection optics for detector 215 are specified to be near paraxial, so that variations in scattering angle within the detection volume can be neglected.

This model described above can then be utilized to design an optical scattering sensor, and evaluate its performance for a given application. For the present purpose, we consider the example of a sensor intended to measure total aerosolized mass. From a historical perspective, this particular requirement served as the initiation point for the development of this model, since smoke detection and alarm thresholds have traditionally been expressed in terms of mass loading. Once again, the measurement of mass corresponds to measurement of the third moment of the particle size distribution. Given existing data from a range of combustion generated aerosols, the CMD incorporates all values between 0.08 and 0.352 micrometers, and $\sigma_g$ ranges from 1.8 to 2.21. The refractive index likewise ranges from 1.35 to 1.67. In the exact sense, the third moment obtained from optical scattering conforms to total aerosolized volume, and requires knowledge of material density to derive total mass.

Figure 4A:
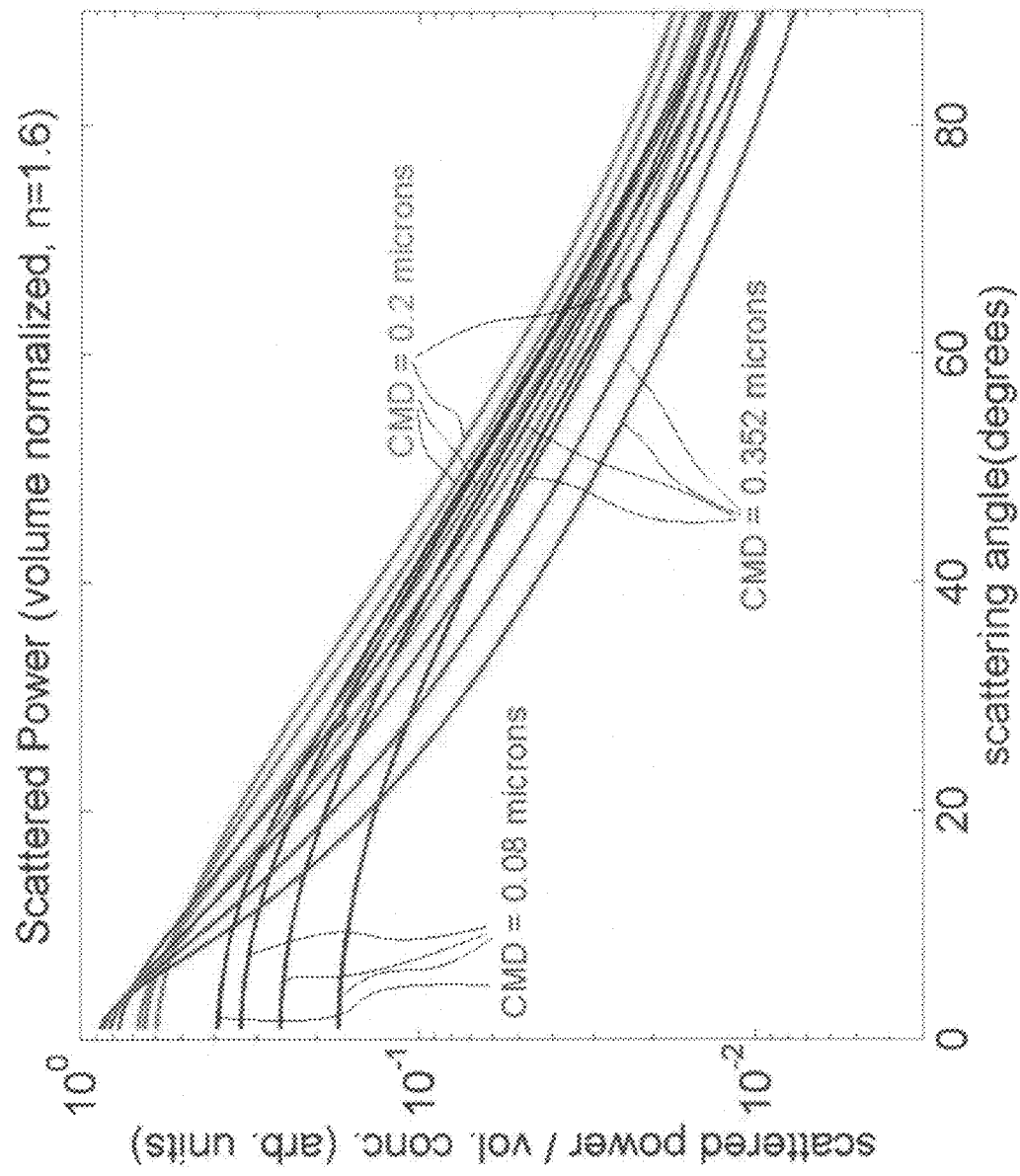
Figure 4B:
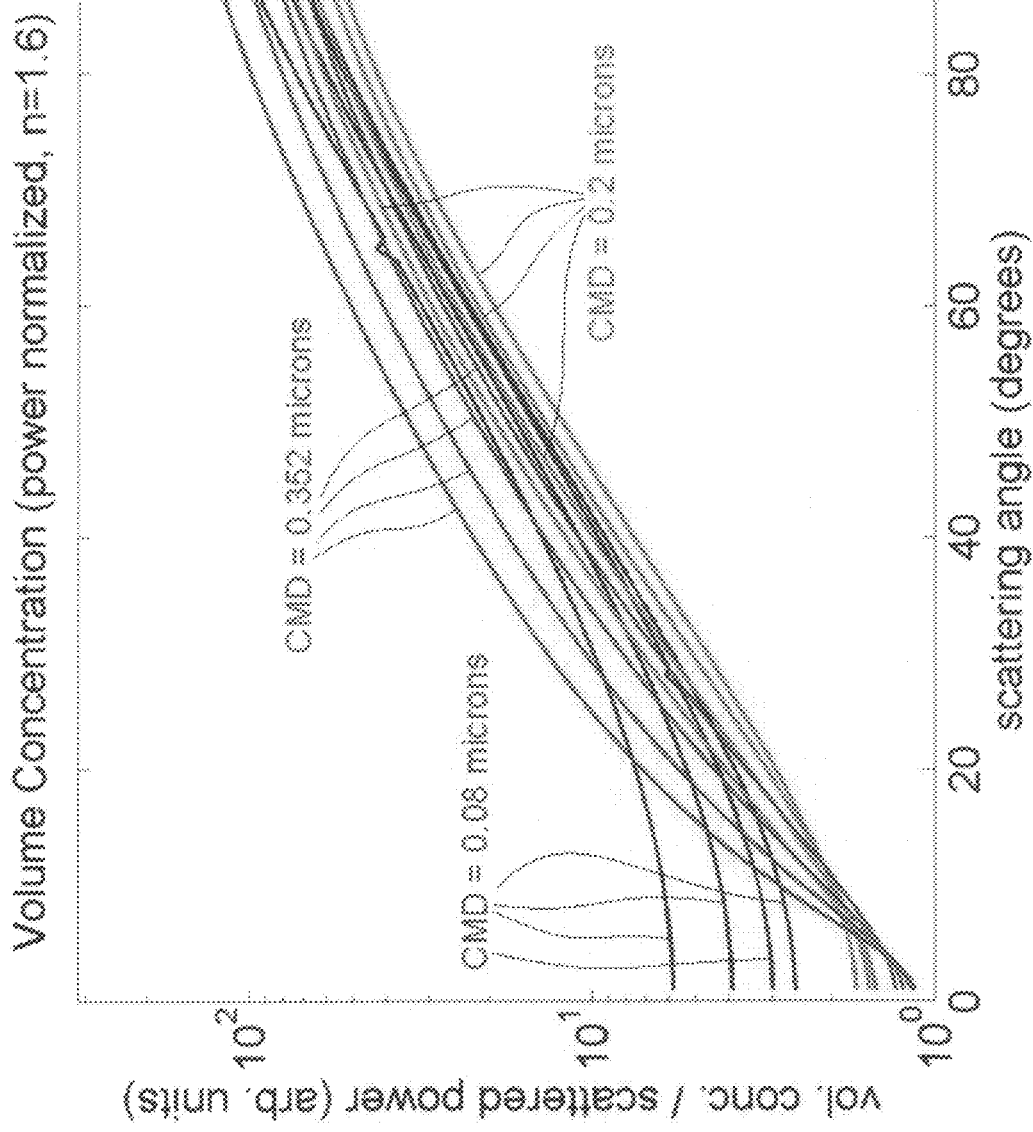
Figure 5:
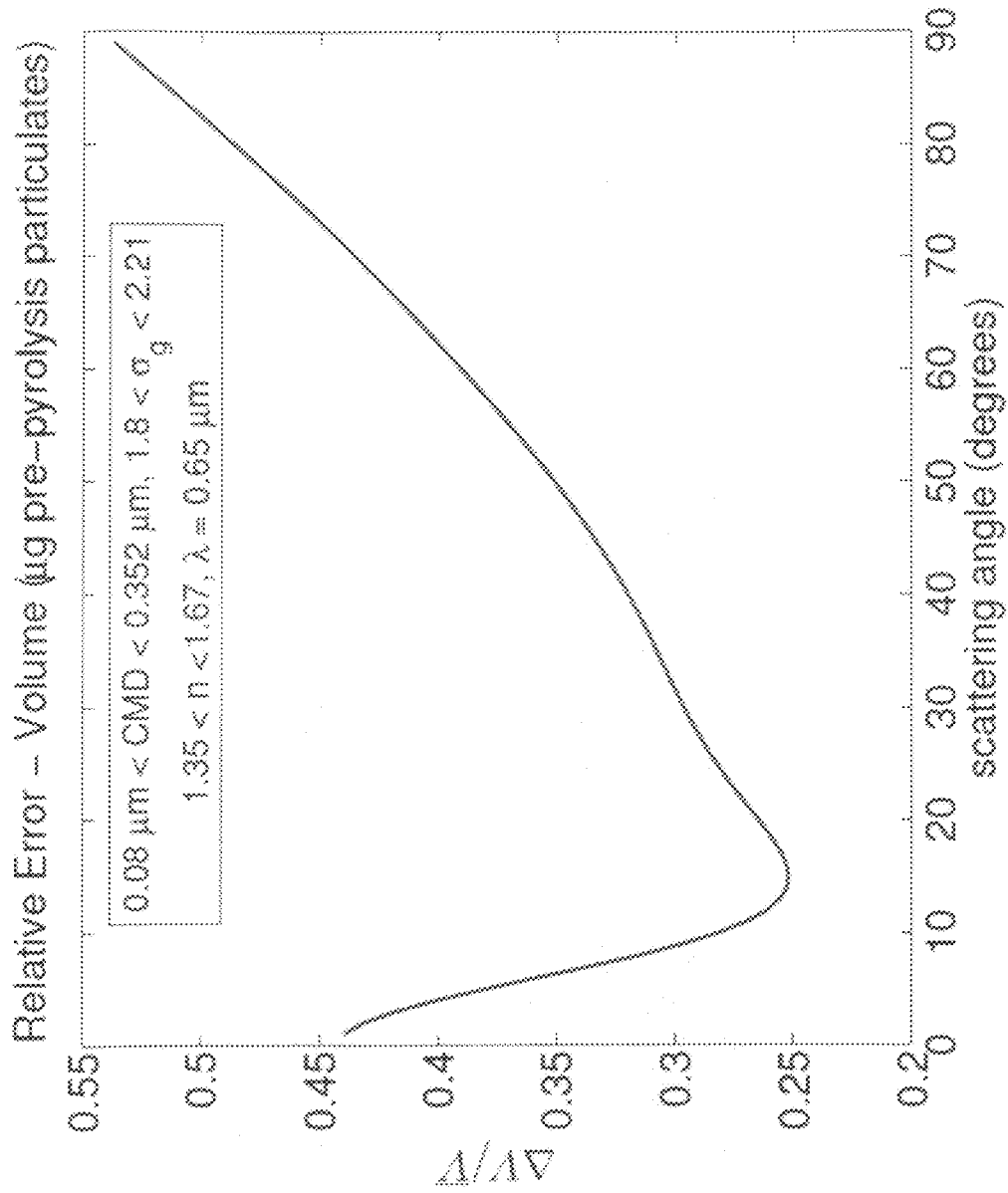

A representative "spaghetti plot" for this case is shown in FIG. 4A. It displays discrete families of curves for the scattered power vs. angle, for fixed volume concentration, as CMD and $\sigma_g$ vary over prescribed ranges. The index of refraction in this case is n=1.6. Each family depicts discrete values of $\sigma_g$ corresponding to a single value of CMD. The wavelength was specified to correspond to a generic solid-state laser diode (650 nanometers), and the collection aperture is 4.5 degrees, full angle. As an alternative to FIG. 4A, which reflects the physics of the aerosol scattering (i.e. the scattered power as a function of angle), one can plot the inverse of the same data (FIG. 4B), which is the volume concentration vs. angle, for fixed scattered power. It is the relative dispersion of this quantity that we wish to minimize so as to insure that volume estimates (or any other integrated moment) are as independent of the modal parameters as possible.

One measure of this relative dispersion, $\Delta V_{conc}/\overline{V_{conc}}$, is plotted in FIG. 5, for the pre-pyrolysis aerosol modal parameter ranges and optical properties given above. It is defined by $$\frac{\Delta V_{conc}}{\overline{V_{conc}}} = \frac{\Delta\left[\frac{1}{\left(\frac{P_i(\theta_V)}{V}\right)_{model}}\right]}{C_{V2}(\theta_V)}$$

As seen, the resulting curve demonstrates a clearly identifiable minimum value in total relative error of 25%, occurring at a collection angle of roughly 14 degrees from the forward direction (relative to the incident light). In practice, the sensor is calibrated to the midpoint of the parametric curves shown in FIG. 4B, such that the maximum error in any given measurement corresponds to roughly 13%. This magnitude of error might seem excessive at first, but must be viewed in light of the problem statement expressed by the associated modal values. In reality, the ranges of variation for both CMD and $\sigma_g$ capture what might be expected from virtually any possible pyrolysis aerosol. Thus, given essentially no a priori knowledge whatsoever about the aerosol being encountered, a single, fixed angle scattering measurement yields an absolute measurement error for the total aerosolized volume of less than 15%. The model can also be used to study other parametric relationships, such as the dependency on wavelength, collection aperture, sums or ratios of multiple detector outputs, etc.

It can also be seen in FIG. 5 that the minimum achievable relative error for this range in modal parameters is essentially half of that afforded by traditional scattering photometers that detect at an angle of 90°. The type of information conveyed in this figure is also informative relative to the current "go/no go" mass-based fire detection alarm criterion, and the single-point monodisperse aerosols used for the associated calibration. In this case, the ability of a given sensor to measure a particular aerosol parameter can now be quantitatively assessed. As will be discussed later, this process can be applied to other moment integrals (or mathematical combinations of moment integrals), then used to optimize the accuracy in the measurement of the resulting quantity, and bound the associated error.

Associating $\Delta V_{conc}/\overline{V_{conc}}$ as a means for quantifying the resulting error is not a unique representation, and other error metrics can be used to quantifying the measurement error. The motivation here stems from an attempt to capture the considerable volume of data produced by the calculation underlying FIG. 4B. Only a limited number of values of CMD and $\sigma_g$ are shown for clarity, and for simplicity, only one value of refractive index is used in this case. When attempting to convey the accuracy under actual practice conditions, the complete range for each successive parameter is typically quite large. As such, the total matrix of angular scattering curves will number several thousand in all. The set of values for all such curves (and their inverses) at a specified scattering angle in itself comprises a distribution, and the use of the relative deviation as an expression for the spread of this distribution is presented as a useful measure. It does not necessarily provide a worst-case indication of the possible measurement error under all conditions, but provides an effective description of the anticipated performance overall.

FIGS. 6A-6R illustrate the determination of the optimal measurement/scattering angle θ (between the detector and the optical axis, see FIG. 3) for various model parameter ranges (i.e. a priori distribution information) for various aerosols of practical interest (e.g., soot, cement, flour, coal, lunar dust) for measuring the $2^{nd}$ (surface area) and $3^{rd}$ (mass) moments of the aerosols with a minimum measurement error. The a priori distribution information is represented by CMD ranges and $\sigma_g$ ranges (shown on each graph) which broadly characterize the aerosol. The wavelength of the input laser beam that illuminates the aerosol is also shown on each graph. Specific refractive indices were used for the different aerosols.

For the prescribed a priori distribution information, the modal parameter ranges were uniformly sampled for a total of M=100 combinations of CMD and standard deviation of aerosol size distribution $\sigma_g$. The procedure for determining the optimal angle is as follows. Considering that the main discriminator between materials is the index of refraction, first, an index of refraction corresponding to a given material (as an example, n=1.7+0.1*i, which corresponds to coal) and a laser wavelength are chosen. Then, the instrument response (volume or surface area) is calculated as a function of detection angle, for that index of refraction and particles whose mean diameter (CMD) and standard deviation (sigma) fall in some range. As an example, ranges of 0.1 micron to 0.5 micron for CMD and 1.8 to 2.2 for sigma were considered. Next, the relative error in the estimate of the volume (or surface area) was calculated. This error is the standard deviation in the instrument response (for volume) divided by the mean instrument response (for volume). Finally, the detection angle for which this error is minimum is selected. In this way, the optimal detection angle can be calculated for a given material (index of refraction) for a range of particle sizes.

This procedure was performed for six different materials (soot, cement, coal, flour, nominal pyrolysis products, and lunar dust) and two wavelengths (0.65 microns and 1.3 microns). Sigma was taken to lie in the range 1.6 to 2 or 1.8 to 2.2. Multiple ranges for CMD were considered, such as 0.08<CMD<0.352, 0.1<CMD<0.5, 0.5<CMD<1, and 0.1<CMD<1. The parameter space of sigma and CMD was randomly sampled 240 times, i.e. the instrument response was calculated 240 times with CMD and sigma taken from the prescribed ranges.

In general, the optimal angle will be different for different materials (as determined by the indices of refraction), as well as for the same material and wavelength, but different size ranges, although it tends to converge as larger particle sizes are included.

The following graphs are shown in FIGS. 6A-6R:

FIG. 6A: measurement error versus angle, and optimal angle providing minimal error in measurement, for measurement of aerosol surface area for a set of broad CMD ranges and $\sigma_g$ ranges (set 1); typical modal parameters and optical properties of certain soot, cement, flour, coal and lunar dust aerosols lie within these ranges; FIG. 6B: measurement error versus angle, and optimal angle providing minimal error in measurement, for measurement of aerosol volume for the same set of broad CMD ranges and $\sigma_g$ ranges; the wavelength of the input laser beam that illuminates the aerosol is 1.3 µm;

FIG. 6C: measurement error versus angle, and optimal angle providing minimal error in measurement, for measurement of aerosol surface area for another set of broad CMD ranges and $\sigma_g$ ranges (set 2); typical modal parameters and optical properties of certain soot, cement, flour, coal and lunar dust aerosols lie within these ranges; FIG. 6D: measurement error versus angle, and optimal angle providing minimal error in measurement, for measurement of aerosol volume for the same set of broad CMD ranges and $\sigma_g$ ranges; the wavelength of the input laser beam that illuminates the aerosol is 1.3 µm;

FIG. 6E: measurement error versus angle, and optimal angle providing minimal error in measurement, for measurement of aerosol surface area for another set of broad CMD ranges and $\sigma_g$ ranges (set 3, which includes set 1 and set 2); typical modal parameters and optical properties of certain soot, cement, flour, coal and lunar dust aerosols lie within these ranges; FIG. 6F: measurement error versus angle, and optimal angle providing minimal error in measurement, for measurement of aerosol volume for the same set of broad CMD ranges and $\sigma_g$ ranges; the wavelength of the input laser beam that illuminates the aerosol is 1.3 µm;

FIG. 6G: measurement error versus angle, and optimal angle providing minimal error in measurement, for measurement of aerosol surface area for a set of broad CMD ranges and $\sigma_g$ ranges (set 1); typical modal parameters and optical properties of certain soot, cement, flour, coal and lunar dust aerosols lie within these ranges; FIG. 6H: measurement error versus angle, and optimal angle providing minimal error in measurement, for measurement of aerosol volume for the same set of broad CMD ranges and $\sigma_g$ ranges; the wavelength of the input laser beam that illuminates the aerosol is 0.65 µm;

FIG. 6I: measurement error versus angle, and optimal angle providing minimal error in measurement, for measurement of aerosol surface area for another set of broad CMD ranges and $\sigma_g$ ranges (set 2); typical modal parameters and optical properties of certain soot, cement, flour, coal and lunar dust aerosols lie within these ranges; FIG. 6J: measurement error versus angle, and optimal angle providing minimal error in measurement, for measurement of aerosol volume for the same set of broad CMD ranges and $\sigma_g$ ranges; the wavelength of the input laser beam that illuminates the aerosol is 0.65 µm;

FIG. 6K: measurement error versus angle, and optimal angle providing minimal error in measurement, for measurement of aerosol surface area for another set of broad CMD ranges and $\sigma_g$ ranges (set 3, which includes set 1 and set 2); typical modal parameters and optical properties of certain soot, cement, flour, coal and lunar dust aerosols lie within these ranges; FIG. 6L: measurement error versus angle, and optimal angle providing minimal error in measurement, for measurement of aerosol volume for the same set of broad CMD ranges and $\sigma_g$ ranges; the wavelength of the input laser beam that illuminates the aerosol is 0.65 µm;

FIG. 6M: measurement error versus angle, and optimal angle providing minimal error in measurement, for measurement of aerosol surface area for another set of broad CMD ranges and $\sigma_g$ ranges (set 4, which is larger than set 3) together with a fixed aerosol particle refractive index (1.5) which generally describes or approximates many aerosols; FIG. 6N: measurement error versus angle, and optimal angle providing minimal error in measurement, for measurement of aerosol volume for the same set of broad CMD ranges and $\sigma_g$ ranges and for the same refractive index; the wavelength of the input laser beam that illuminates the aerosol is 0.65 µm;

FIG. 6O: measurement error versus angle, and optimal angle providing minimal error in measurement, for measurement of aerosol surface area for a set of parameters that describe aerosol distribution studied during the Smoke Aerosol Measurement Experiment (SAME) experiment under reduced gravity (described in more detail in the section titled Motivation for Sensor Development below); FIG. 6P: measurement error versus angle, and optimal angle providing minimal error in measurement, for measurement of aerosol volume for the same set of aerosol parameters; the wavelength of the input laser beam that illuminates the aerosol is 0.65 µm;

FIG. 6Q: measurement error versus angle, and optimal angle providing minimal error in measurement, for measurement of aerosol surface area for a set of parameters that describe aerosol distribution studied during the Smoke Aerosol Measurement Experiment (SAME) experiment under reduced gravity, with refractive index of aerosol fixed to 1.5; FIG. 6R: measurement error versus angle, and optimal angle providing minimal error in measurement, for measurement of aerosol volume for the same set of aerosol parameters; the wavelength of the input laser beam that illuminates the aerosol is 0.65 μm.

As the above exemplary figures show, the method presented herein allows for 1) optimizing the accuracy of a sensor, and 2) bounding the error in the measurement accuracy. The relationship between the desired measurement (e.g. total mass or the $3^{rd}$ moment, total surface area or the $2^{nd}$ moment, etc.), and the properties of the aerosol being measured (e.g., the peak and width of the size distribution, as well as the refractive index of the particles) allows for determining an optimal angle for measurement by the sensor (and the value of the error at this optimal angle), as well as the error in measurement when the angle of the sensor is within a certain range around the optimal angle. The figures show that the accuracy of a sensor measurement depends on the broad range of parameters that were used to describe the aerosols and to obtain a measurement angle for the sensor. If the composition, and hence physical parameters, for an aerosol are known with higher precision the sensor angle can be optimized to obtain a very precise measurement of the aerosol moment. In either case, the measurement error is much smaller than any measurement error of conventional fire detectors or similarly existing dust or particle photometers. That is, even if only limited knowledge is available about an aerosol (i.e., broad CMG and $\sigma_g$ ranges), measurement conditions, such as sensor angle, can be determined for which a rather accurate sensor moment can be obtained. The measurement error is obtained as well.

Take for example FIG. 6J. By providing the broad CMG and $\sigma_g$ ranges, an angle of about 5 degrees is determined to be the optimal angle for measuring aerosol volume, for which it is also determined that the error in measurement will be about 0.06. It can also be determined that if a measurement angle of 10 degrees is used, the error in measurement will be about 0.33. Thus, if the sensor, arranged at 5 degrees would measure a volume of 5 mg of aerosol (as an example), then it is known that the actual aerosol mass is within 5 mg±0.06*5 mg. However, if a sensor arranged at 10 degrees would measure a volume of 5 mg of aerosol, then the actual aerosol mass is within 5 mg±0.33*5 mg.

Thus, if ranges for the aerosol properties, such as the peak and width of the size distribution ranges, as well as the refractive index range for the particles, are specified a priori, then it is possible to calculate an optimal wavelength and detection angle to minimize the error in measuring a particular moment of interest. An associated measurement accuracy may also be calculated, so that, if a sensor is built using this wavelength and detection angle, then the maximum error (or probable error, etc., depending on how the error is mathematically defined) will be "X," as long as the aerosols of interest fall within this range of properties.

One exemplary method for measuring aerosols is to generate aerosol-specific data such as a list of optimal angles associated with specific aerosols of interest. This set of data, which may be structured as a database, list, etc. and included on a computer readable medium associated with the MPASS sensor, allows to build a sensor to accurately measure any moment for any type of aerosol by using predetermined detection angles which may be specific to each moment. In an exemplary embodiment, a database may include predetermined detection angles for measuring the $1^{st}$, $2^{nd}$, and $3^{rd}$ moments for a set of aerosols.

A database including predetermined detection angles for certain aerosols can be generated using information regarding aerosol properties (such as distribution and/or optical properties). Some information regarding aerosol properties can be found in journal papers that studied certain aerosols. Information regarding aerosol properties may also be determined as needed, by studying certain aerosols to generate such data.

Another way to obtain a list of detection angles for measuring certain aerosols is to note that there are some aerosol properties that generally do not vary as much as other properties. For example, the aerosol refractive index is generally well known for many aerosols, and it also does not vary much across the same aerosol class. Thus, the refractive index or refractive index ranges are set as a first parameter that describes each material (e.g. coal, lead, beryllium, wood dust, fire signatures, etc.) that may form aerosols through pyrolysis. The optimal detection angles may then be calculated for an exhaustive set of possible aerosol size distributions. In an exemplary embodiment, the Count Median Diameters (CMD) for an exhaustive set of possible aerosol size distributions may include ranges from 0.1-0.5 microns, from 0.5-1.0 microns, from 1.0-5.0 microns, and standard deviations may include ranged between 1.6-2.0, from 2.0-2.2, etc. In this manner, any possible aerosol distribution for all (or at least most) materials of interest may be taken into consideration to obtain detection angles for measuring those aerosols.

Sensor Calibration

By way of the computational model, the output of the sensor for a desired integrated moment can be made to correspond to any set of aerosol properties, or ranges in these aerosol properties. This only requires that the end-to-end efficiency of each of the detectors has been characterized using a reference aerosol. This aerosol may be monodisperse or polydisperse. In both cases, the total concentration and refractive index should be known independently, and for the latter, any two additional modal parameters should also be known. This information is sufficient to calculate the constant $C_1$, which has the dimension of watt/volt. In the preceding discussion concerning the exemplary measurement of volume and surface area, this constant was designated as $C_{V1}$ and $C_{A1}$, respectively. $C_1$ then characterizes the optical source strength, the efficiency of the transmitting and receiving optics, the sensitivity of the detector, and the electronic gain of any additional preamplifiers or amplifiers.

Once $C_1$ has been determined, the computational model is utilized to scale the sensor output to correspond to any integrated moment of interest for any aerosol of interest. The required inputs to the model consist of the probability density function for the aerosol size distribution, and the refractive index of the material. If the inputs are specified in the form of ranges of any or all of these parameters, the computational model can also be used to calculate confidence bounds for any measured integrated moment.

This feature represents an advancement relative to the current state-of-the art, described in more detail below. At present, the sensor response corresponding to a specified moment must be obtained via direct calibration using the particular aerosol of interest. This calibration cannot be extended to any other aerosol, wherein any of the modal properties and/or refractive index differ from the original test aerosol.

The existing state-of-the-art for calibrating scattering photometers involves the use of a reference aerosol. This is most commonly performed using ISO Standard 12103-1 Arizona Test Dust. Since to date the measured quantity of interest is the aerosolized mass concentration, the photometer output is then compared with that of a direct reading mass analyzer (e.g. Tapered Element Oscillating Microbalance, Beta Analyzer, or Gravimetric Analysis).

The shortfall of this method is that it is not extensible. Adjusting the photometer to respond to other materials requires that the instrument be recalibrated using said material. However, the situation is more difficult in actual practice.

This arises because the photometer response is not only a function of the refractive index of the material, it is also a function of the modal parameters of the aerosol size distribution. Stated more precisely, suppose the instrument is calibrated to measure the mass concentration of Material "A," wherein the size distribution of the test aerosol has a Count Median Diameter (CMD) of "B," and a Geometric Standard Deviation (GSD) of "C". Then, even if the instrument is used to measure the same material, the calibration will be invalid if the CMD and the GSD of the aerosol of interest are different.

Unless the instrument geometry and its response function are based on a first-principles fundamental, underlying model, it is impossible to either predict or adjust the calibration when either the aerosolized material or its modal parameters are varied. Further, lacking this underpinning, it is impossible to bound the measurement uncertainty of the instrument if these quantities are known to exist only within specified ranges.

An instrument whose design is derived from an underlying physical model offers an additional fundamental advantage. Specifically, the reading for any desired moment quantity can be determined once the end-to-end instrument response function has been determined by direct calibration. In this case, this can be accomplished using aerosols of monodisperse reference particles. Such materials are readily obtained, where both the size and refractive index are known with great precision. The modal parameters of a monodisperse aerosol are nugatory; i.e. one only need to measure either the number concentration, or any other moment concentration to fully characterize the aerosol.

This same approach offers considerable advantages when calibration the optical efficiency of the sensor hardware itself. Specifically, it is experimentally challenging to create a polydisperse reference aerosol with constant modal properties; e.g. CMD and $\sigma_g$. In this case, the calibration can be performed using a monodisperse reference aerosol. Any moment can be utilized (e.g. count, surface area, volume, mass), depending on the reference instrumentation available.

Embodiment Including Multiple Detectors

The capability provided by the computational model can also be used to optimize the measurement accuracy of a multi-detector sensor relative to a specific aerosol. This optimization process can be performed a priori, or on-the-fly during a measurement sequence.

In one embodiment of the present application, a sensor may be configured as an array of multiple detectors. This is in contrast to constructing a sensor with detector(s) at a fixed angle(s) that has been optimized for a specific application. A user elects to apply this device for a given application; i.e. they input the material or materials they are interested in, any pre-knowledge they might have about the anticipated size distribution parameters (or default values if such pre-knowledge is lacking), and the moment quantities to be measured.

Given these input assumptions, an algorithm based on the computational model would then select the optimal set of angular detectors to measure the desired moments for this specific case. Again, the model would also output the associated confidence bounds that flow from this combination of material/aerosol parameters and detection angles.

To implement a Multi-Angle optimization procedure, an initial estimate of the modal properties and refractive index of the aerosol of interest is made. This information can be input by the user, or default values can be assumed. These parameters can be specified exactly, or as ranges for any or all parameters.

The computational model is then employed to calculate the optimal detection angle(s) that minimize the relative error for the measurement of the desired moment(s) properties for this specific aerosol or range or aerosol properties. An algorithm then selects from among the multi-angle detectors that are available in the particular sensor embodiment at hand, and enables that detector(s) most closely matching the optimally computed detection angle. The model then establishes the calibration for this combination of angle and moment as described in the Calibration Section above. When ranges are specified for one or more aerosol parameters, the model can then calculate a confidence bound for the measurement of the desired moment(s).

This process can also be implemented on-the-fly. In this case, several moment quantities are used to calculate a best estimate to the modal properties of the aerosol being measured. This can be done numerically, or for the case where the size distribution can be approximated by a lognormal distribution, computed exactly using the Hatch-Choate relationships. The process of optimizing the detection angle(s) is then performed iteratively, using the sequence described above.

FIG. 7 illustrates a generic, multi-angle instrument consisting of an arbitrary number of angularly spaced detectors. The multi-angle instrument illustrated in FIG. 7 includes N detectors $215_1, 215_2, \ldots, 215_N$ arranged at N angles $\theta_1, \theta_2, \ldots, \theta_N$ with respect to the optical axis of input beam 201, for measuring one or more moments for one or more aerosol types included in aerosol 210.

In an exemplary embodiment, the number of detectors is on the order of 6-10.

Hardware Implementation for an Exemplary Embodiment of the Sensor

The task of developing sensors for spacecraft and other field applications promotes an end-state package with the expected "hardened" attributes, i.e. minimal mass, volume and power consumption, high reliability, stability, inherent lifetime, etc. This in turn drives the use of solid-state optical sources and detectors, rugged structural assemblies, and an inherently robust design insofar as tolerance to thermal conditions, mechanical vibration, and shock.

Based on these considerations, and employing the modeling capability described above, a flight-qualified device was constructed for inclusion the ISS reflight experiment SAME-R (described in more detail in the section titled Motivation for Sensor Development below). A photograph of the interior of the sensor is shown in FIG. 8, in which: item 710 is a controller and analog electronics assembly, item 720 is a laser diode driver, items 730 are Solid-state detector/preamplifiers, item 740 is an integrated optics block and item 750 is a laser diode source.

In constructing a compact sensor that relies on elastic scattering, the most challenging consideration involves stray light rejection. This involves proper conditioning, focusing, and baffling of the incident beam, as well as the use of spatially matched receivers. Some details of these features in the MPASS are described in a publication by Hunter, G. W., Greenberg, P. S., Xu, J. C., Ward, B., Makel, D., Dutta, P., and Liu, C. C., "Miniaturized Sensor Systems for Early Fire Detection in Spacecraft," International Conference on Environmental Systems, Savannah, GA, 2009, the entire contents of which are hereby incorporated by reference. The sensor package itself includes an embedded CPU/controller, which performs signal averaging, background subtraction, and asynchronous data communication. As configured, each digital data point represents a 100 point linearly-weighted average, providing an effect bandwidth of ≈1 Hz. for each channel. This module also provides for analog amplification to appropriately scale the signals from the detector preamplifiers. The individual channel gains are set such that the Noise-Equivalent-Power (NEP) of the detectors is equal to the least significant bit of the input analog/digital (A/D) converter. This balances sensitivity and dynamic range, while avoiding extraneous noise bits, or false resolution. For the flight unit, a redundant analog output was added to take advantage of the parallel options for downlinking the separate analog and digital data streams. Since the analog output is only sampled once per second, the embedded electronics module included a 5-pole, low pass Butterworth filter for each channel, with a corresponding 6 dB cutoff at 100 Hz. The flight package was subject to the standard array of qualification testing, including thermal cycling, off-gassing, three-axis vibration, and a 100 hour burn-in. No drift in background levels or responsivity was observed at the conclusion of these tests.

Figure 8:
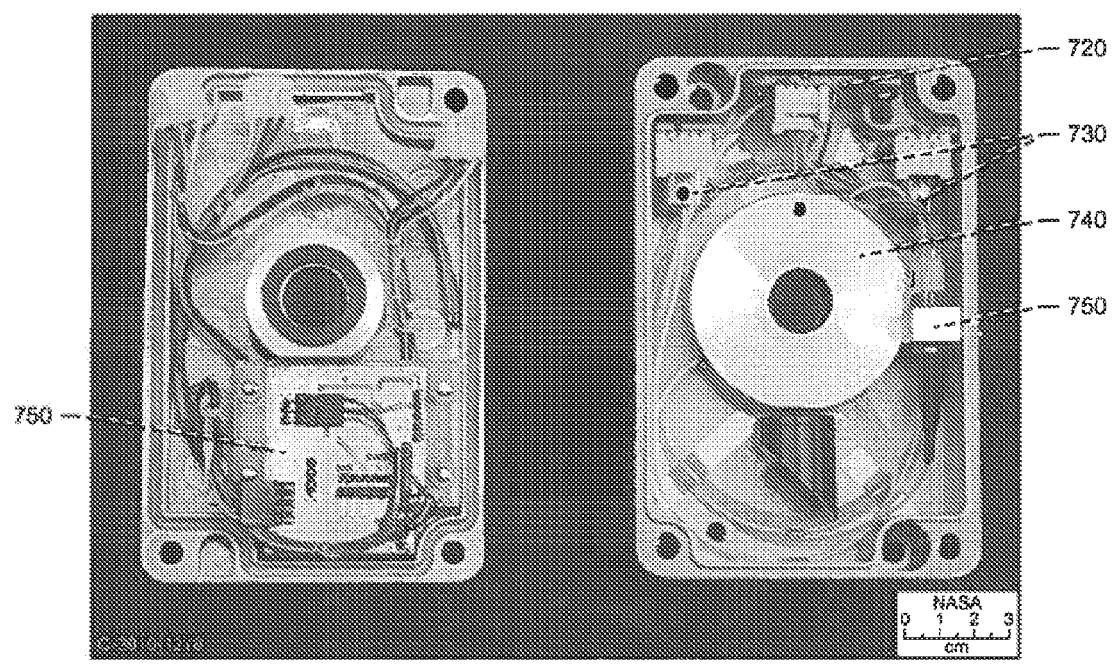
Figure 9:
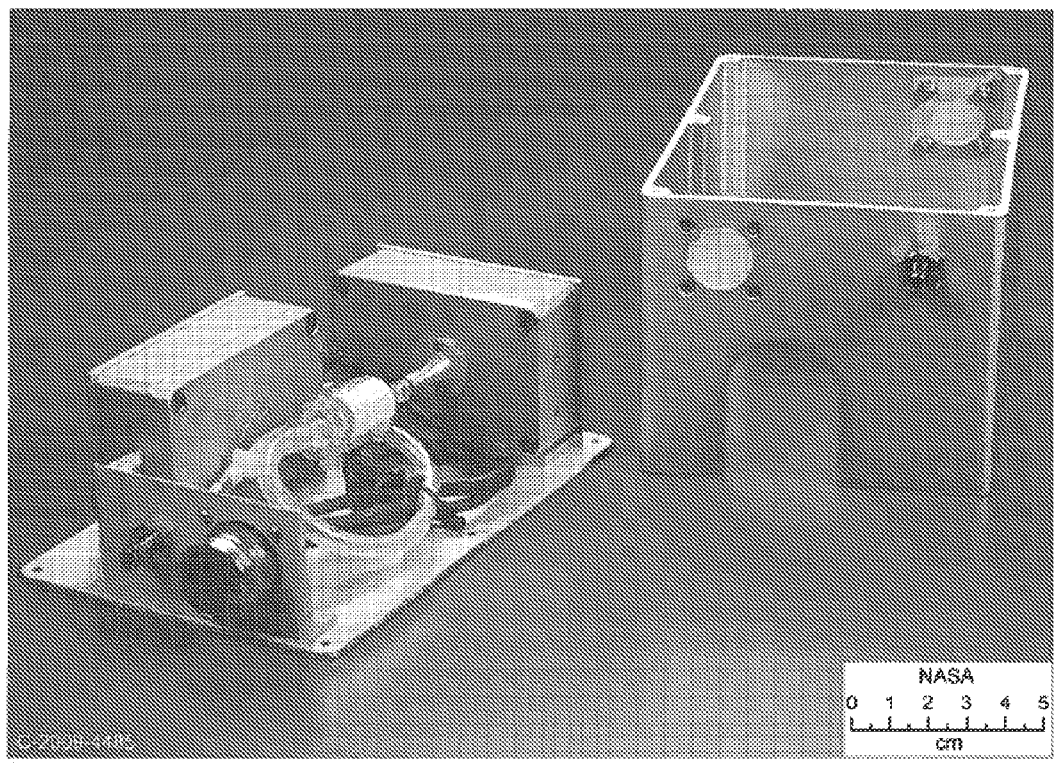

FIG. 9 illustrates a complete flight package, as delivered, and including the exemplary aerosol detection sensor of FIG. 8. In addition to the scattering sensor itself, the package includes a power conditioning and voltage conversion module, fluidic connections to match those used in the SAME hardware configuration, and suitably rated mounting hardware and enclosure.

Testing and Results of an Exemplary MPASS Sensor

An exemplary MPASS sensor may quantify and optimize the measurement of total aerosolized mass which provides one type of fire alarm trigger levels. Another exemplary MPASS also includes the measurement of total surface area, i.e. the $2^{nd}$ integrated moment distribution, which is of interest for post-fire clean up and in issues relating to human respiratory exposure. The total surface area strongly correlates with health effects and particulate exposure. A publication by Driscoll, K. E, "Role of inflammation in the development of rat lung tumors in response to chronic particle exposure" Inhal. Toxicol., 8 (suppl.), 139-153, 1996, the entire contents of which are hereby incorporated by reference, describes the correlation between total surface area and health effects. The inclusion of this additional measurement, in combination with the quantitative determination of mass, merged well with the moment method approach employed by SAME, and the overall interest in early-warning detection of the FPDS Project. The reflight opportunity presented by SAME-R therefore offered an opportunity to test the MPASS relative to actual reduced-gravity fire signatures, while adding the simultaneous opportunity to bolster SAME's moment method calculations with a tighter bound on the $3^{rd}$ moment, and the addition of the $2^{nd}$.

A sensor according to the present invention was constructed and tested in the laboratory in response to an ensemble of aerosols. The specific sensor was optimized to characterize both the $2^{nd}$ (total surface area) and $3^{rd}$ (total volume) integral moments. The resulting data demonstrated good agreement with the modeling results, establishing confidence in the model as both a design tool, and for characterizing the measurement accuracy of any particular optical configuration.

A laboratory apparatus was constructed to validate the underlying model, as well as to calibrate the optical conversion constants contained within $C_i(\lambda, \phi)$, using the exemplary MPASS designed and fabricated for $2^{nd}$ and $3^{rd}$ moment characterization. A general schematic diagram of this laboratory apparatus is illustrated in FIG. 10A. A description of the validation procedure and calibration is presented below.

The design approach for a particulate sensor described in the present application offers unique features insofar as calibration. Specifically, the calibration formalism separates the instrumental response into two parts. The first part characterizes the hardware itself, by way of parameter $C_1$ (such as $C_{V1}$ and $C_{A1}$, previously mentioned).

The second part then employs the first-principles scattering model to characterize the response of a given sensor unit to a specific aerosol or range of aerosols, by way of $C_2(\theta)$ (such $C_{V2}(\theta_V)$ and $C_{A2}(\theta_A)$, as previously mentioned). As such, a given sensor can be calibrated in a variety of ways. For example, using a polydisperse aerosol, the response to an integrated moment can be measured, as in FIGS. 10B and 10C, where FIG. 10B illustrates a configuration for calibration with a polydisperse aerosol, whereby the concentration of the reference aerosol can be measured with a counter 588A. However, the sensor response can also be determined using a monodisperse aerosol. FIG. 10C illustrates a configuration for calibration with a monodisperse aerosol, in which a differential mobility column 581 fixed to pass a specified particle size is used. This eliminates the variability associated with repeatedly generating a polydisperse aerosol. The concentration of the monodisperse reference aerosol can be measured in a number of ways; e.g. with a counter 588B, with a TEOM 526, by way of total mass, with another reference instrument 582 for measuring any moment, etc. Using a polysdisperse reference aerosol further complicates the calibration procedures, as the associated size distribution should be completely characterized.

The core of the calibration apparatus is a pressure driven-Collison atomizer 519. The other elements shown in FIG. 10A are: a mass flow controller 503, HEPA filters 506A and 506B, a dilution vessel 529, a diffusion dryer 513, a $Kr^{85}$ isotope ionization neutralizer 509, a MPASS sensor 215C, a Tapered Element Oscillating Microbalance (TEOM) 526 described in more detail below, a waste unit 533, and a Scanning Mobility Particle Spectrometer (SMPS) 523.

The pressure driven-Collison atomizer 519 was used to aerosolize a variety of materials from liquid phase suspension, and is useful for producing stable and repeatable aerosol distributions. A total of six materials were utilized in all, including solid salts (both NaCl and KCl), methylene blue, and oleic acid. In line with the assumptions used in the model, the resulting distributions conformed well to lognormal form, displaying $\chi^2$ goodness of fits ranging from 0.986-0.997. When comparing with the model, literature values were used for both refractive index and density. It is important to note that these values were imported directly, and were not derived on the basis of a best fit to the model.

The atomizer 519 output is then passed through the diffusion dryer 513 to remove the liquid phase carrier, and then through the $Kr^{85}$ isotope ionization neutralizer 509 to remove residual charge. This eliminates subsequent electrostatic particle losses in both the delivery tubing and measurement instruments. The aerosols are then diluted with filtered air as needed in a mixing vessel to produce overall concentrations compatible with the MPASS sensor 215C and the other laboratory reference instruments.

Two separate instruments were required to provide reference values for the $2^{nd}$ and $3^{rd}$ integral moments. The latter was provided by the Tapered Element Oscillating Microbalance (TEOM) 526, which is a direct-reading instrument for the measurement of mass. A TEOM is described in Baron, P.

A., and Willeke, K., *Aerosol Measurement*, John Wiley, New York, 2001, pp. 395-398, the entire contents of which are hereby incorporated by reference. Again, since the MPASS 215C measures integrated volume concentration, literature values are used to convert this quantity to the total mass reported by the TEOM. The MPASS 215C is placed directly in line with the TEOM 526, such that both instruments sample the aerosol identically.

Figure 11A:
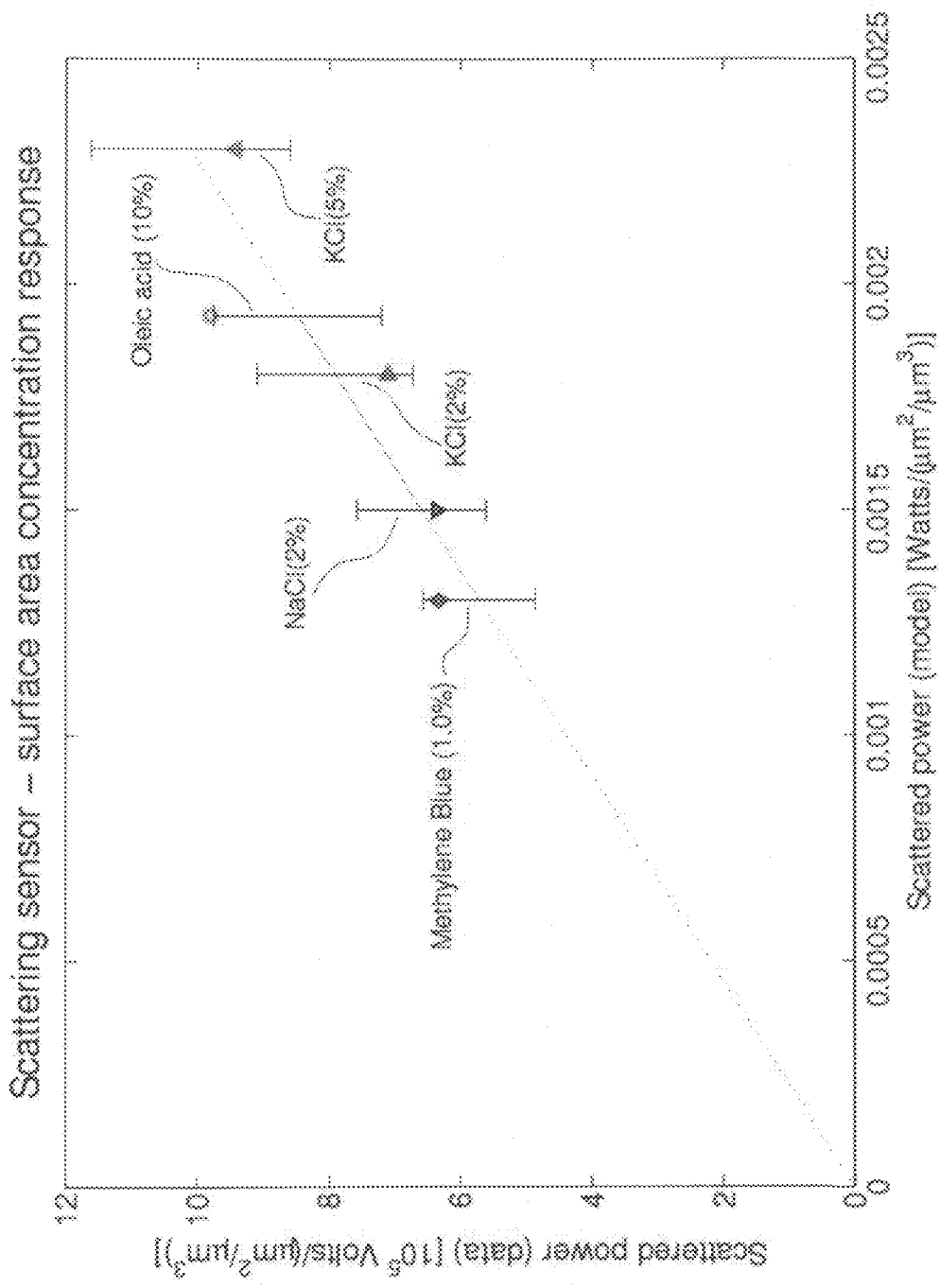
Figure 11B:
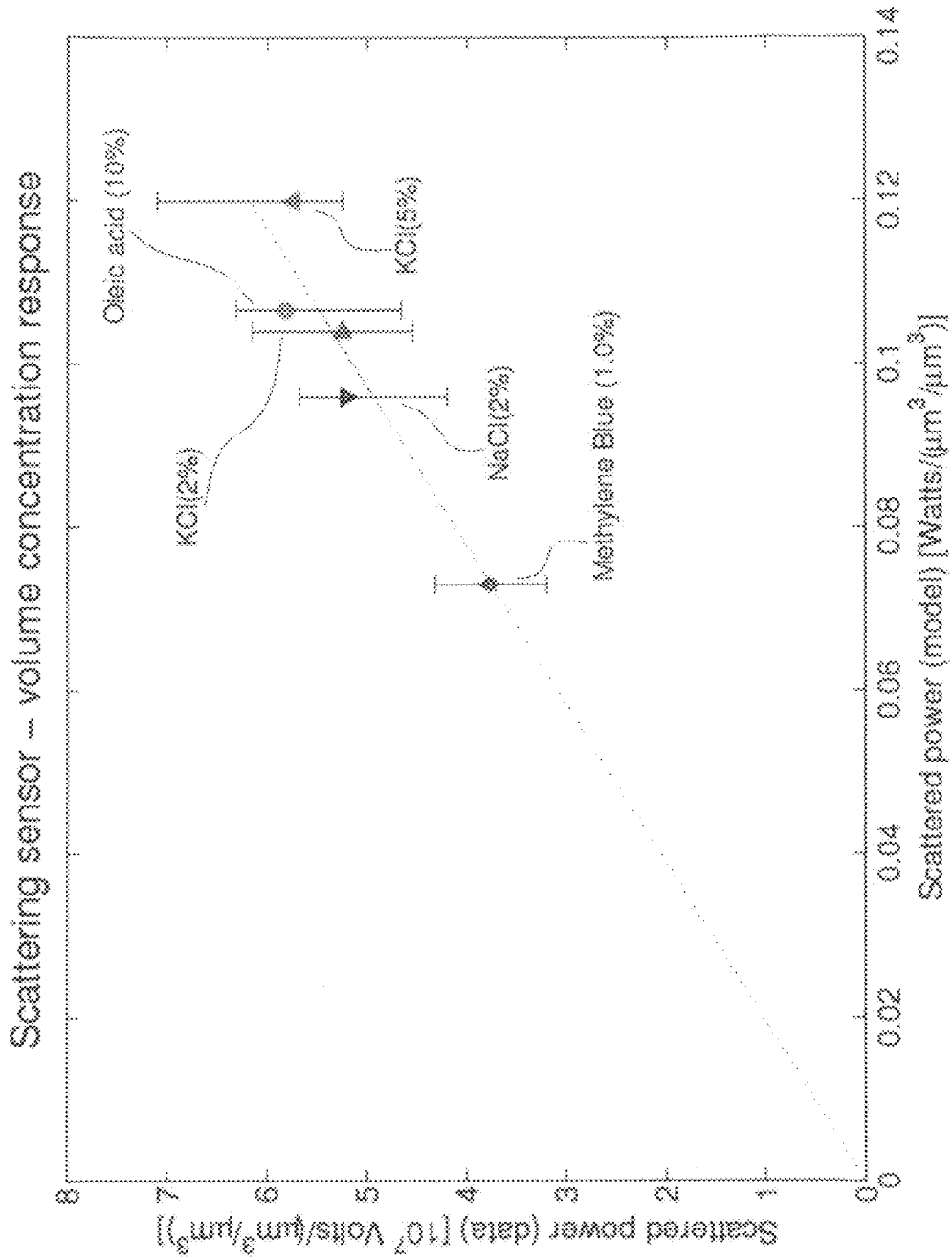

Providing a reference value for total surface area is more complex, since no accurate instruments are presently available for this purpose. Although a somewhat complex alternative, this quantity was derived from the measurement of the complete particle size distribution, as determined using the Scanning Mobility Particle Spectrometer (SMPS) 523. An SMPS is described in Baron, P. A., and Willeke, K., *Aerosol Measurement*, John Wiley, New York, 2001, pp. 547-565, the entire contents of which are hereby incorporated by reference. The SMPS 523 directly measures the number concentration as a function of particle size, wherein the corresponding surface area can be calculated. To compensate for losses occurring in the SMPS, the mass concentration is calculated first, and normalized to the value provided directly by the TEOM 526. The resulting normalization constant is then applied to the value for total surface area calculated from the SMPS size spectrum. The results of this experimental study are shown in FIGS. 11A and 11B. Specifically, for each of the five test aerosols, the absolute optical power scattered into the detectors is compared to that predicted by the model.

The error bars include the inherent fluctuations in the aerosol generator itself, as well as the cascaded error of the associated reference instruments. Since the drift of the MPASS 215C over the duration of each test aerosol is less than the least significant bit reported from the A/D, it is considered exact. Although the data in FIGS. 11A and 11B provide the optical conversion efficiency needed to calibrate the system constants $C_1$, the more significant feature is the observed agreement between the data and the model for the total ensemble of aerosols. The measured data is well within the predicted error bounds, and therefore provides a confident basis for validating the ability of the model to accurately predict the response of a given sensor geometry to an aerosol of specified modal parameters. As such, the model can be used to optimize a sensor for other direct or derived quantities, or to demonstrate its response to a given aerosol or class of aerosols. The close agreement seen in FIGS. 11A and 11B also establishes confidence in the ability of the computational model to correctly predict the sensor response to values of both CMD and GSD that may be difficult to generate as reference aerosols in the laboratory.

A few examples are offered to illustrate the utility afforded by the validated model. Consider FIG. 6H. The CMD is allowed o range from 0.1-0.5 µm, and $\sigma_g$ from 1.6-2.0. The wavelength is fixed at 0.65 µm, and the respective plots illustrate the variation in relative error as a function of scattering angle for the refractive indices of the materials shown. The resulting minima in measurement error are relatively closely bunched in the vicinity of eight to fourteen degrees. The exception is soot, resulting physically from the imaginary component of the refractive index. In contrast, now consider FIG. 6J. With all other factors held constant, the range in CMD is extended to an upper bound of 1.0 µm. The resulting minima are now more tightly grouped [including soot], and the corresponding angular location shifts forward to approximately five degrees off forward.

Consider now FIG. 6N. The CMD is allowed to range from 0.08-1.0 µm, and $\sigma_g$ from 1.6-2.0. The wavelength is specified again at 0.65 µm, but in this example the value of refractive index is fixed at 1.5. A distinct and advantageous minimum in measurement error is observed at approximately nine degrees off forward. A secondary minimum is observed at ninety degrees, but is nearly fifty percent larger than observed for the former location. In FIG. 6P, the range in CMD is altered to provide an upper bound of 0.352 µm. $\sigma_g$ now ranges from 1.8-2.21, and the refractive index is now permitted to range from 1.35-1.67. The angular location for minimizing relative error shifts to roughly fifteen degrees, and is reduced by approximately sixteen percent. In this example, however, no secondary minimum occurs, and the relative error at ninety degrees is exceptionally poor.

The above demonstrates the value of the model as a design tool, and for bounding the associated error for a given sensor configuration.

Motivation for Sensor Development

Experiments that resulted in design and development of sensors according to the present invention include experiments conducted on the International Space Station (ISS) which resulted in design and development of a unique two-moment smoke particulate detector.

Ongoing efforts have been conducted under NASA's Fire Detection, Prevention, and Suppression (FPDS) Project to address features relating to fire safety, such as spacecraft fire safety, and develop advanced sensor technologies. The relatively recent CSD and SAME flight experiments have provided useful data for this purpose, and these results have been utilized to guide efforts aimed at providing sensors with improved performance. These activities range from the evaluation of materials, fundamentals of ignition and flame spread, reliable early warning detection, and methods for suppression. Numerous features of this project arise from the unique physical aspects of combustion occurring under conditions of reduced gravity.

Descriptions of existing provisions for spacecraft systems are provided in more detail in papers by Friedman and Urban (Friedman, R., "Fire Safety Practices and Needs in Human-Crew Spacecraft," Journal of Applied Fire Science, Vol. 2, 1992, pp. 243-259; and Urban, D. L., Griffin D., Ruff, G. A., Cleary, T., Yang, J., Mulholland, G., Yuan, Z. G., Detection of Smoke from Microgravity Fires", 2005 International Conference on Environmental Systems, Rome Italy, Paper #2005-01-2930 July 2005, SAE Transactions, pp 375-384), the entire contents of which are hereby incorporated by reference. Specifications pertaining to the fire detection requirements for the Space Shuttle and International Space Station (ISS) are provided in a publication by Steisslinger, et al. (Steisslinger, H. R., D. M. Hoy, J. A. McLin and E. C. Thomas., "Comparison Testing of the Space Shuttle Orbiter and Space Station Freedom Smoke Detectors," SAE Paper 932291, 1993), the entire contents of which are hereby incorporated by reference. In the context of the development presented here, these requirements are relatively sparse in the level of technical detail. For example, the Shuttle detector was designed to alarm at a concentration of 2 mg/m$^3$, as tested in response to a monodisperse sample of one micrometer particles. Alternately, the same detector could also alarm in response to an observed rise in concentration of 0.022 mg/m$^3$/s for 20 seconds. The ISS detection system was specified to alarm at a corresponding obscuration of 1%/ft, where this quantity was measured using an Underwriters Laboratory (UL) smoke box and a white light extinction meter. In practice, a monodosperse aerosol of 0.5 micrometer polystyrene (PSL) beads was employed as a transfer standard, first being calibrated against the smoke box/white light meter, then used to adjust the alarm setpoints for the ISS detectors themselves. In terms of the more recent understanding of both fire detection systems and reduced gravity combustion science, it is notable that these requirements are not reflective of possible differences in the fire signatures themselves, the placement and number of detectors, and the spatial and/or temporal evolution of the particulate aerosols as they are transported.

To place these requirements in perspective, it is acknowledged that quantitative data on reduced gravity fire signatures has emerged relatively recently. In terms of prepyrolysis products, i.e. the recondensed polymer fragments associated with early warning signatures, there are now two principle data sets. The first resulted from the Comparative Soot Diagnostics experiment described in a paper by Urban et al. (Urban, David L.; Griffin, DeVon W.; Gard, Melissa Y., "Comparative Soot Diagnostics: Preliminary Results," Fourth International Microgravity Combustion Workshop, pp. 205-210, 1997), the entire contents of which are hereby incorporated by reference, conducted on the Space Shuttle. The pyrolized samples consisted of a number of materials utilized in spacecraft applications, and included by intent those commonly associated with electrical systems. The results suggested that these aerosols could produce liquid smoke particles larger than 1 micrometer in diameter, while the solid carbonaceous particles associated with the later stages of flaming combustion remained in the sub-micrometer range. The CSD experiment did not include sufficient instrumentation to afford a more complete characterization of the resulting size distributions, such that the resulting data remained insufficient to serve as a guide for detector design.

The subsequent Smoke Aerosol Measurement Experiment (SAME) was initiated to more fully characterize the aerosol distributions associated with reduced gravity, early warning (i.e. prepyrolysis) fire signatures. SAME was conducted on the ISS in 2007 during Expedition 15 (described by Urban, D. L. Ruff, G. A., Mulholland, G. W., Cleary, T. G., Yang, J. C., Yuan, Z. G., "Measurement of Smoke Particle Size under Low-Gravity Conditions," 2008 International Conference on Environmental Systems, Chicago, Ill., Paper 2008-01-2089, the entire contents of which are hereby incorporated by reference), and contained three separate instruments designed to measure the $0^{th}$, $1^{st}$, and $3^{rd}$ moment distributions. If the resulting aerosols are reasonably approximated by a lognormal distribution, these three moments can be algebraically combined to calculate the Count Median Diameter (CMD), $\sigma_g$, the Geometric Standard Deviation (GSD), and the total aerosol concentration, as described in Cleary, T. G., D W. Weinert, and G. W. Mulholland, "Moment Method for Obtaining Particle Size Measures of Test Smokes", Natl. Inst. Stand. Technol., NISTIR 7050, 2003, the entire contents of which are hereby incorporated by reference. Given these three quantities, other moment averages of the distribution can be subsequently derived. SAME contained the additional capability to age the aerosols, affording the opportunity to emulate the increased transit time from source to detector that occurs under reduced-gravity conditions, as explained by Brooker, J. E., Urban, D. L., Ruff, G. A., "ISS Destiny Laboratory Smoke Detection Model", 7ICES-113,2007 International Conference on Environmental Systems, Chicago, Ill., 2007, the entire contents of which are hereby incorporated by reference.

The SAME test matrix comprised 30 materials in all, including six samples of five different material: Teflon®, Kapton®, silicon rubber, cellulose (lamp wick), and dibutyl phthalate. The resulting data yielded a number of useful outcomes relating to the refinement of detectors for spacecraft applications. While not offered as an exhaustive analysis, the most salient features are noted here. Irrespective of the physical differences affecting combustion under reduced-gravity conditions, the materials of lampwick and silicone produced pyrolysis aerosols not markedly different from those associated with terrestrial early warning fire signatures. However, when subject to the prescribed 720 second aging period, the CMDs increased significantly. The Teflon samples produced somewhat smaller particles, exhibited similar evolution with aging, but again, did not produce particle sizes that differed significantly from those observed terrestrially. This particular result appears somewhat inconsistent with the larger particle sizes that were qualitatively observed in the earlier CSD experiment,[4] an aspect being revisited in further detail in the upcoming reflight of SAME (designated as SAME-R). In contrast, the CMDs of the Kapton aerosols were relatively small, roughly a third compared to the nominal value for terrestrial signatures, which is on the order of 190 nanometers (see Bukowski, R. W. and Mulholland, G. W., "Smoke Detector Design and Smoke Properties," NBS Technical Note 973, U.S. Department of Commerce/National Bureau of Standards, 1978, the entire contents of which are hereby incorporated by reference). Even when subject to aging, the SAME CMD remained roughly 20% smaller than this value.

This data from SAME presents important implications insofar as to the responsivity of conventional smoke detectors. In the broadest terms, such detectors are based on two primary technologies: ionization and optical scattering. The former are generally viewed as most appropriate for the relatively smaller carbonaceous particles produced in flaming combustion, whereas the latter are viewed as more suitable for the condensed pre-pyrolysis aerosols associated with early warning signatures (see Bukowski et al., described above). Notably, the results from SAME present an interesting detection challenge, in that the palette of possible signatures occurs in both size regimes. As illustrated in FIGS. 3 and 4 in the publication Comparative Soot Diagnostics: Preliminary Results" by Urban, David L.; Griffin, DeVon W. and Gard, Melissa Y. described above, the associated response from both types of conventional detectors becomes problematic. An ionization-based device responds poorly (i.e. poor sensitivity) to aerosols with relatively larger CMDs, whereas the situation is reversed for a typical scattering device, i.e. poor sensitivity to smaller CMDs.

This situation can be framed more precisely. In terms of fundamental detector performance, achieving suitable cross-sensitivity (i.e. detecting larger particles with an ionization detector, or detecting smaller particles with a scattering based device) is not the critical issue. The more correct problem statement is that by constructing an optical detector so as to achieve adequate cross-sensitivity, the same detector becomes overly sensitive in its traditional size range (typically >200-300 nm). Given no other information about the signature itself (e.g. absolute concentration, precise modal properties, gas-phase chemistry, particle composition, etc.), this leads to the problematic situation of experiencing a high probability of false alarms. While this outcome is arguably not critically incapacitating in residential fire detection, and some industrial applications, in remote habitats such as aircraft, spacecraft, submarines, etc. where egress and mitigation becomes a complex issue, this is an enormously important consideration.

In the literal sense, this feature encapsulates the motivation for pursuing the development of advanced technologies for early warning fire detection presented in the present application. The reliable and prompt identification of evolving fire hazards requires sensors of adequate sensitivity, while simultaneously including provisions to exclude false events with high probability. In principal, the combination of a more thorough understanding of reduced-gravity combustion signatures and more sophisticated detectors suitable for network deployment will provide the ability to determine both the location, origin, and evolution of fire-related events. While the inclusion of additional sensors, e.g. those capable of quantifying gas-phase composition, may prove to be an important component, the approach here is to maximize the information available from the particulate aerosol. The detector development described in the present application utilizes optical scattering, due to the richness of information available from particle-light interactions.

The MPASS device described in the present application represents the present state-of-the-art in NASA's development path. Predicated on the depth of information available via optical scattering, the MPASS has been designed to characterize integral moment properties of aerosol distributions. As originally prescribed, it was developed to optimize the measurement of total aerosolized mass for the typical modal properties associated with early warning fire signatures. This parameter space includes those signatures observed in CSD and SAME.

Applications Enabled by the Methods and Sensors Disclosed Herein

The sensors disclosed in the present application characterize properties of aerosols or other ensembles of particulates, such as, for example, various pyrolysis products as well as liquid-phase suspensions, solid phase mineral particles, and other ensembles of particles dispersed in air, void, fluid, etc., using a computational method for designing and optimizing such sensors. Physical features, components, and the arrangement of such components in the sensors can also be optimized using the computational model. The family of sensors described in the present application measure the scattering of light from distributions of particles such as aerosols. The particular arrangement of the sensor, e.g. the wavelength(s) of incident radiation, the number and location of optical detectors, etc. can be derived so as to optimize the sensor response to aerosol properties of practical interest.

The present invention discloses sensors for a variety of applications, and also methods to implement such sensors. The sensors deliver improved accuracy relative to existing instruments, and by virtue of the associated reductions in package size, weight, and power consumption, may be used for a host of previously inaccessible field applications. The sensors also exhibit increased accuracy and dynamic range. A single sensor provides the ability to measure multiple aerosol properties. The sensors can be implemented as stand-alone devices. The sensors are inherently low maintenance and high reliability by design. In addition, the sensors include features that minimize the collection of stray or background light.

The sensors described in the present application provide significantly better measurement accuracy relative to existing instruments, based on the underlying computational modeling that allows the optimization of the sensors for specific applications. The computational model can also configure the optical geometry/configuration of the sensor so as to retrieve specific information about the particle distribution, to optimize the detected signal or the information that is derived concerning the nature of the particles, and to retrieve specific distribution parameters, moment averages, or combinations of these quantities for measured aerosols. The approach is also unique, in that it affords the ability to establish bounds on measurement uncertainty when ranges in the modal and optical properties have been specified. The approach is further unique in its extensibility: the instrument response to changes in these properties or the measurement of other moment quantities can be accurately predicted without the need for direct calibration.

The model also allows for optimization of the illumination and detection geometry of an aerosol detection system including the sensor, to maximize stray light reduction and to optimize the quantification of fundamental aerosol properties. The computational model processes multi-spectral information to retrieve information about specific aerosol properties. The information input into the model or output as an optimization result also includes the number of detectors to be used in one set-up for detection of a certain aerosol, the geometry of the detectors, and wavelength of the illumination sources to be used for generating scattered light by aerosols.

The sensors also enable novel applications by the physical attributes of the resulting configuration. Of particular note is the ability to accurately measure the total surface area of an aerosol. This parameter is of enormous interest from the perspective of respiratory health, and no instruments presently exist for accurate total particles surface area detection and surface area measurements in the field. In combination with the aforementioned physical size of these sensors, this facet is of considerable importance.

Direct applications for the sensors include: environmental monitoring, human health assessment, fire detection, emission/pollutant monitoring, emission characterization, process monitoring and control, as well as any other fields that involve measurements of aerosols' presence and/or aerosols' properties. In a preferred embodiment, the present invention is used for advanced particulate sensors for Early Warning Fire Detection in terrestrial environments (e.g., households, industrial settings, buildings, and ground, water or underground/underwater vehicles), and other environments such as on a spacecraft/plane, etc.

The foregoing description of an implementation of the invention has been presented for purposes of illustration and description. It is not exhaustive and does not limit the invention to the precise form disclosed. Modifications and variations are possible in light of the above teachings or may be acquired from the practicing of the invention.

Although detailed embodiments and implementations of the present invention have been described above, it should be apparent that various modifications are possible without departing from the spirit and scope of the present invention. It is understood that preferred embodiments of the invention have been shown and described above to illustrate possible features of the invention, and numerous modifications could be made to the preferred embodiments. Therefore, the invention is not intended to be limited to the preferred embodiments described above, but rather is intended to be limited only by the claims set out below. Accordingly, the invention encompasses all alternate embodiments that fall literally or equivalently within the scope of these claims.

We claim:

1. A method for measuring modal properties of an ensemble of polydisperse particles, said method comprising:
   providing an ensemble of polydisperse particles;
   selecting a modal property to be measured for the ensemble of polydisperse particles;
   determining the measurement geometry, including illumination wavelength and the angular placement and collection angle of one or more optical detectors, that minimizes the measurement error in the selected modal property;
   determining the conversion factor that relates the measured optical power to the selected modal property;
   placing optical detectors at the determined collection angles and the determined locations;
   illuminating the ensemble of polydisperse particles simultaneously with light;

measuring the light scattered by the ensemble of polydisperse particles with the optical detectors;

converting the output of the optical detectors to electrical signals;

wherein the electrical signals provide a quantitative measure of the modal property.

2. The method of claim 1, where the modal property is selected from the group consisting of the number of particles, the surface area of particles, and the mass of the particles.

3. The method of claim 2, where the step of determining the measurement architecture also determines bounds on the measurement error of the modal parameter.

4. The method of claim 1, where the modal property can be any integrated moment of a particle size distribution of a refractive index.

5. The method of claim 1, where the measurement geometry that minimizes the measurement error of a selected modal property is termed optimal.

6. The method of claim 1, wherein the detection angle is within 10% of the optimally determined angle for measurement of a selected modal property.

7. The method of claim 1, wherein a physical sensor parameter and/or a optimally determined detection angle for the sensor is/are adjusted to bound the measurement uncertainty for a selected modal property within 15% of a minimum measurement uncertainty achievable for an anticipated ranges of properties characterizing the ensemble of polydisperse particles, consisting of:
   (a) the count median diameter or other characteristic size parameter of the ensemble of polydisperse particles of particles,
   (b) the geometric standard deviation or other characteristic width parameter of the ensemble of polydisperse particles,
   (c) the refractive index of the particles,
   (d) the wavelength of the incident radiation.

8. The method of claim 7, wherein the optimal detection angle is different from 90°, and the error bound for the optimal detection angle does not include 90°.

9. The method of claim 7, wherein said particles are aerosols, and said determining step includes:
   specifying a range for one or more aerosols properties (a) and/or (b) and/or(c) and/or (d), and determining at least one of a bound on the measurement uncertainty of at least one selected modal property an optimized detection angle for detecting scattered radiation that minimizes this uncertainty bound.

10. The method of claim 7, wherein said particles are aerosols, and an output corresponding to said at least one selected modal property of the ensemble of polydisperse particles is related to an aerosol described by specific values of (a) and/or (b) and/or (c) and/or (d) and/or specific bounds of values of (a) and/or (b) and/or (c) and/or (d), by a method other than a direct calibration to said aerosol.

11. The method of claim 1, wherein the particles are aerosols, and said method further comprises calibrating a sensor to a reference aerosol, before said sensor receives said radiation scattered by the ensemble of polydisperse particles.

12. The method of claim 11, wherein said calibrating step calibrates an optical collection and electrical conversion efficiency for the sensor using the reference aerosol for which a selected modal property of the ensemble of polydisperse particles has been accurately characterized, wherein said reference aerosol is different from said ensemble of polydisperse particles receiving said radiation, and said method further comprises measuring with the sensor a value for the selected modal property of said ensemble of polydisperse particles, without recalibrating the sensor to said ensemble of polydisperse particles.

13. The method of claim 12 wherein said method further comprises: selecting, before said determining step, said at least one selected modal property of the ensemble of polydisperse particles to be measured.

14. The method of claim 12, further comprising selecting a model distribution function and characteristic parameters describing said distribution function for an ensemble of polydisperse particles, based on a type of said particles.

15. The method of claim 12, said method further comprising:
   adjusting a plurality of detection angles for a plurality of moveable sensors, to measure one or multiple modal properties for the ensemble of polydisperse particles.

16. The method of claim 15, wherein the plurality of detection angles are optimized, based on an a priori knowledge of the anticipated knowledge of the ranges for:
   (a) the count median diameter or other characteristic size parameter of the ensemble of polydisperse particles,
   (b) the geometric standard deviation or other characteristic width parameter of the ensemble of polydisperse particles,
   (c) the refractive index of the particles,
   (d) the wavelength of the incident radiation.

17. The method of claim 1, said method further comprising:
   selecting, from among a plurality of fixed sensors, a sensor arranged at an angle closer to said optimal detection angle than the other of the fixed sensors, and measuring, using said selected sensor, said modal property for the ensemble of polydisperse particles.

* * * * *